(12) United States Patent
Adam et al.

(10) Patent No.: US 7,018,998 B2
(45) Date of Patent: Mar. 28, 2006

(54) GLUTAMATE RECEPTOR ANTAGONISTS

(75) Inventors: Geo Adam, Schopfheim (DE);
Alexander Alanine, Riedisheim (FR);
Erwin Goetschi, Reinach (CH);
Vincent Mutel, Mulhouse (FR);
Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/146,693

(22) Filed: Jun. 7, 2005

(65) Prior Publication Data
US 2005/0234048 A1 Oct. 20, 2005

Related U.S. Application Data

(62) Division of application No. 10/300,449, filed on Nov. 20, 2002, now Pat. No. 6,960,578, which is a division of application No. 09/687,241, filed on Oct. 13, 2000, now Pat. No. 6,509,328.

(30) Foreign Application Priority Data

Oct. 15, 1999 (EP) .................................. 99120519

(51) Int. Cl.
*C07D 243/12* (2006.01)
*C07D 417/04* (2006.01)
*C07D 413/10* (2006.01)
*A61K 31/55* (2006.01)

(52) U.S. Cl. ..................................... 514/221; 540/517
(58) Field of Classification Search ................ 540/517; 514/221
See application file for complete search history.

(56) References Cited

U.S. PATENT DOCUMENTS

| | | | |
|---|---|---|---|
| 5,716,953 A | 2/1998 | Donati et al. | |
| 6,051,712 A | 4/2000 | Binggeli et al. | |
| 6,407,094 B1 * | 6/2002 | Adam et al. | 514/221 |
| 6,544,985 B1 * | 4/2003 | Adam et al. | 514/221 |
| 6,548,495 B1 * | 4/2003 | Adam et al. | 514/221 |
| 6,949,542 B1 * | 9/2005 | Adam et al. | 514/221 |

FOREIGN PATENT DOCUMENTS

| | | |
|---|---|---|
| WO | WO 97/05109 | 2/1997 |
| WO | WO 99/26927 | 6/1999 |
| WO | WO 01/29011 | 4/2001 |
| WO | WO 01/29012 | 4/2001 |

OTHER PUBLICATIONS

Cartmell, et al. Br. J. Pharmacol. 1998, vol. 123(3) pp. 497-504.
Wilson, J., et al., J. Chem. 1983, vol. 36, pp. 2317-2325.
Giroux et al., Tetr. Lett. 1997, vol. 38, pp. 3841-3844.
Ishiyama et al., Tetr. Lett. 1993, vol. 34, pp. 7595-7598.
Kosugi et al., Bull. Chem. Soc. Jpn. 1983, vol. 56, pp. 3855-3856.
Thorand et al., J. Org. Chem. 1998, vol. 63, pp. 8551-8553.
Bellamy et al., Tetr. Lett. 1984, vol. 25 pp. 839-842.
Rathke et al. Synth. Commun. 1985, vol. 15 pp. 1039-1049.
Hagedorn et al., J. Med. Chem. 1987, vol. 30, pp. 1342-1347.
Park, et al., Tetrahedron, 1984, vol. 40, pp. 2985-2988.
Hiromichi et al., Chem. Pharm. Bull. 1983, vol. 31, pp. 1896-1901.
Winkler et al., Tetrahedron Lett., 1998, vol. 39, pp. 2253-2256.
Masayoshi e tal., Journal of Antibiotics, 1978, vol. 31, pp. 1245-1251.
Beny et al., J. Org. Chem. 1982, vol. 47, pp. 2201-2204.
Corey et al., J. Org. Chem. vol. 38, No. 18, p. 3224, 1973.
Brauner-Osborne et al., Ligands for Glutamate Receptor: Design and Therapeutic Prospects, J. Med. Chem. vol. 43, pp. 2609-2645.
CAS Printout for JP62174062, Chem. Abstracts vol. 108: 75434 (1987).
CAS Printout for Solomko et al., Chem. Abstracts vol. 102:132005.
CAS Printout for Solomko et al., Chem. Abstracts vol. 102:6436.
CAS Printout for Bougrin et al., Chem. Abstracts vol. 122:239666.
CAS Printout for Hamdi et al., Chem. Abstracts vol. 121:83303.
CAS Printout for Rao et al., Chem. Abstracts vol. 117:69839.
M. Hanumantha, Rao, et al., Synthesis vol. 5, pp. 446-448 (1992).

* cited by examiner

*Primary Examiner*—Bruck Kifle
(74) *Attorney, Agent, or Firm*—George W. Johnston; Patricia S. Rocha-Tramaloni; Kimberly J. Prior

(57) ABSTRACT

The present invention is a compound of formula

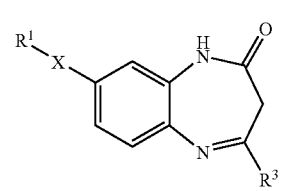

I wherein
X is an ethynediyl group, $R^1$, $R^2$ and $R^3$ are as defined in the specification.

5 Claims, No Drawings

GLUTAMATE RECEPTOR ANTAGONISTS

PRIORITY TO RELATED APPLICATIONS

This application is a Division of Ser. No. 10/300,449, filed Nov. 20, 2002, which is now U.S. Pat. No. 6,960,578, which is a Division of Ser. No. 09/687,241, filed Oct. 13, 2000, which is now U.S. Pat. No. 6,509,328, issued: Jan. 21, 2003.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be subdivided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

SUMMARY OF THE INVENTION

The present invention relates to compounds of the general formula I:

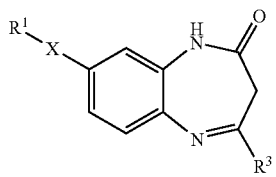

These compounds have been discovered to act as metabotropic glutamate receptor antagonists and accordingly are useful for the treatment of a range of neurological disorders, including psychosis, schizophrenia, Alzheimer's and other cognitive and memory disorders.

Objects of the present invention are compounds of formula I and their pharmaceutically acceptable salts per se and as pharmaceutically active substances, their manufacture, medicaments based on one or more compounds in accordance with the invention and their production, as well as the use of the compounds in accordance with the invention in the control or prevention of neurological disorders, and, respectively, for the production of corresponding medicaments.

DETAILED DESCRIPTION

The present invention relates to compounds of formula I

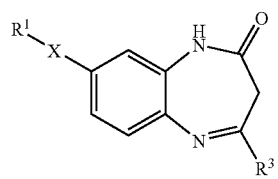

wherein
X is a single bond or an ethynediyl group, wherein,
in case X is a single bond,
in case X is an ethynediyl group,
$R^1$ is hydrogen; lower alkyl, optionally substituted with hydroxy; halo-lower alkyl; lower cycloalkyl, optionally substituted with hydroxy, lower alkyl, halo-lower alkyl, lower alkoxy, halo-lower alkoxy, or halogen; lower cycloalkenyl, optionally substituted with lower alkyl, halo-lower alkyl, lower alkoxy, halo-lower alkoxy, halogen, or oxo; lower alkenyl; phenyl, optionally substituted with halogen, lower alkyl, halo-lower alkyl, lower cycloalkyl, lower alkoxy, halo; 5 or 6 membered heterocyclic ring, optionally substituted with lower alkyl, halogen, oxo, benzyloxy, benzoyl, methanesulfonyl, benzenesulfonyl, acetyl, pivaloyl, tert. butoxycarbonyl, or tert. butylcarbonyl; or benzofuranyl;
$R^3$ is phenyl; pyridine; thiophenyl or thiazolyl, which are optionally substituted with halogen, cyano, nitro, azido, hydroxy, carboxy, morpholine-4-carbonyl, carbamoyl, thiocarbamoyl, N-hydroxycarbamoyl, trimethylsilyl-ethynyl, or from lower alkyl, lower alkynyl, lower alkoxy, halo-lower alkyl, 4-lower alkyl-piperazine-1-carbonyl, lower alkylaminocarbonyl, which are optionally substituted by amino, lower alkylamino, acylamino, oxo, hydroxy; lower alkoxy, lower alkylthio, or carboxy which is optionally esterified or amidated; or a 5-membered aromatic heterocycle which is optionally substituted by amino, lower alkylamino, acylamino, oxo, hydroxy, lower alkoxy, lower alkylthio, carboxy which is optionally esterified with lower alkyl or amidated with lower alkylamino which is eventually substituted by hydroxy, or lower alkyl which is optionally substituted by halogen, hydroxy, amino, lower alkylamino, acylamino, or amidino, which is optionally substituted by lower alkyl, —C(NRR')=NR" (where R, R' and R" are hydrogen or lower alkyl), hydroxy, lower alkoxy, lower alkylthio, acyloxy, lower alkylsulfinyl, lower alkylsulfonyl, lower alkoxy-lower alkylsulfanyl, lower alkylsulfanyl, cycloalkylsulfinyl, cycloalkylsulfonyl, hydroxyimino, or lower alkoxyimino, which is optionally esterified or amidated, lower alkenyl, oxo, cyano, carbamoyloxy, or sulfamoyl which is optionally substituted by lower alkyl,
with the proviso that, if X is a single bond and $R^3$ is pyridinyl, $R^1$ is not hydrogen, or methyl;
and their pharmaceutically acceptable acid addition salts.

It has surprisingly been found that the compounds of formula I are metabotropic glutamate receptor antagonists. Compounds of formula I are distinguished by valuable therapeutic properties.

The compounds of the present invention can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Objects of the present invention are compounds of formula I and their pharmaceutically acceptable salts per se and as pharmaceutically active substances, their manufacture, medicaments based on one or more compounds in accordance with the invention and their production, as well as the use of the compounds in accordance with the invention in the control or prevention of illnesses of the aforementioned kind, and, respectively, for the production of corresponding medicaments.

Preferred compounds of formula I are those in which $R^3$ is phenyl substituted in meta position by cyano; halogen; or imidazolyl, which is optionally substituted by lower alkyl; or 1,3-thiazolyl which is optionally substituted by hydroxy-lower alkyl, carboxy, or —CO—NH—$(CH_2)_2$OH; 1,3-oxazolyl; 1,2,3-triazolyl; 1,2,4-triazolyl which is optionally substituted with lower alkyl; tetrazolyl; or isoxazolyl, which is optionally substituted by lower alkyl;

The following are examples of such compounds:
3-(4-Oxo-7-phenylethynyl-4,5-dihydro-3H-benzo[b][1,4] diazepin-2-yl)-benzonitrile;
4-(3-Chloro-phenyl)-8-phenylethynyl-1,3-dihydro-benzo[b] [1,4]diazepin-2-one;
4-(3-Imidazol-1-yl-phenyl)-8-phenylethynyl-1,3-dihydro-benzo[b][1,4]diazepin-2-one;
3-[7-(4-Fluoro-phenyl)-4-oxo-4,5-dihydro-3H-benzo[b][1, 4]diazepin-2-yl]-benzonitrile;
8-(4-Fluoro-phenylethynyl)-4-(3-imidazol-1-yl-phenyl)-1, 3-dihydro-benzo[b][1,4]diazepin-2-one;
8-(4-Fluoro-phenylethynyl)-4-(3-[1,2,4]triazol-1-yl-phenyl)-1,3-dihydro-benzo[b][1,4]diazepin-2-one;
8-(4-Fluoro-phenyl)-4-[3-(4-methyl-imidazol-1-yl)-phenyl]-1,3-dihydro-benzo[b][1,4]diazepin-2-one;
8-(4-Fluoro-2-methyl-phenyl)-4-(3-imidazol-1-yl-phenyl)-1,3-dihydro-benzo[b][1,4]diazepin-2-one;
8-(4-Fluoro-2-hydroxy-phenyl)-4-(3-imidazol-1-yl-phenyl)-1,3-dihydro-benzo[b][1,4]diazepin-2-one;
8-(4-Fluoro-phenylethynyl)-4-(3-tetrazol-1-yl-phenyl)-1,3-dihydro-benzo[b][1,4]diazepin-2-one;
8-(2-Fluoro-phenyl)-4-(3-[1,2,3]triazol-1-yl-phenyl)-1,3-dihydro-benzo[b][1,4]diazepin-2-one;
8-(4-Fluoro-phenyl)-4-[3-(3-methyl-isoxazol-5-yl)-phenyl]-1,3-dihydro-benzo[b][1,4]diazepin-2-one;
8-(2,4-Difluoro-phenyl)-4-(3-[1,2,3]triazol-1-yl-phenyl)-1, 3-dihydro-benzo[b][1,4]diazepin-2-one;
8-(2,3-Difluoro-phenyl)-4-(3-[1,2,3]triazol-1-yl-phenyl)-1, 3-dihydro-benzo[b][1,4]diazepin-2-one;
8-(2-Fluoro-phenyl)-4-[3-(4-hydroxymethyl-thiazol-2-yl)-phenyl]-1,3-dihydro-benzo[b][1,4]diazepin-2-one;
2-{3-[7-(2-Fluoro-phenyl)-4-oxo-4,5-dihydro-3H-benzo[b] [1,4]diazepin-2-yl]-phenyl}-thiazole-4-carboxylic acid;
2-{3-[7-(4-Fluoro-phenyl)-4-oxo-4,5-dihydro-3H-benzo[b] [1,4]diazepin-2-yl]-phenyl}-4-methyl-thiazole-5-carboxylic acid (2-hydroxy-ethyl)-amide; and
4-[3-(4,5-Dimethyl-4H-[1,2,4]triazol-3-yl)-phenyl]-8-(4-fluoro-phenyl)-1,3-dihydro-benzo[b][1,4]diazepin-2-one;

Compounds of formula I, in which $R^3$ is thiophenyl, preferably tiophen-2-yl, optionally substituted with halogen, cyano; or pyridinyl, preferably pyridin-4-yl, optionally substituted, preferably in the 2-position, with halogen, or cyano; are also preferred.

The following are examples of such compounds:
8-(4-Fluoro-phenylethynyl)-4-(2-imidazol-1-yl-pyridin-4-yl)-1,3-dihydro-benzo[b][1,4]diazepin-2-one;
2-[7-(4-Fluoro-phenyl)-4-oxo-4,5-dihydro-1H-benzo[b][1, 4]diazepin-2-yl]-thiophene-3-carbonitrile;
4-(4-Oxo-7-phenylethynyl-4,5-dihydro-3H-benzo[b][1,4] diazepin-2-yl)-pyridine-2-carbonitrile; and
4-[7-(2,4-Difluoro-phenyl)-4-oxo-4,5-dihydro-3H-benzo[b] [1,4]diazepin-2-yl]-pyridine-2-carbonitrile.

All tautomeric forms of the compounds of invention are also embraced herewith.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkynyl" used in the present description denotes straight-chain or branched unsaturated hydrocarbon residues with 2–7 carbon atoms, preferably with 2–4 carbon atoms, such as ethynyl, n-propynyl, and the like.

The term "lower cycloalkyl" used in the present description denotes cyclic saturated hydrocarbon residues with 3–5 carbon atoms, preferably with 3 carbon atoms, such as cyclopropyl.

The term "lower alkoxy" denotes a lower alkyl residue in the sense of the foregoing definition bonded via an oxygen atom.

The term "halogen" embraces fluorine, chlorine, bromine and iodine.

The expression "5 or 6 membered heterocyclic ring" embraces thiophene, furane, thiazole, pyridine, partially hydrated pyridine, for example 2-pyridone, partially hydrogenated prydine, for example tetrahydropyridine, five-membered aromatic heterocycle containing up to 4 heteroatoms, selected from O, S, N, embracing imidazol-1-yl, imidazol-2-yl, imidazol-4-yl; pyrazol-1-yl, pyrazol-3-yl, pyrazol-4-yl; 1,3-thiazol-2-yl, 1,3-thiazol-4-yl, 1,3-thiazol-5-yl; 1,3-oxazol-2-yl, 1,3-oxazol-4-yl, 1,3-oxazol-5-yl, 1,2-oxazol-3-yl, 1,2-oxazol-4-yl, 1,2-oxazol-5-yl; 1,2,3-triazol-1-yl, 1,2,3-triazol-4-yl, 1,2,4-triazol-1-yl, 1,2,4-triazol-3-yl, 1,2,4-triazol-2-yl; 1,2,4-oxadiazol-2-yl, 1,2,4-oxadiazol-3-yl, 1,2,4-oxadiazol-5-yl, 1,2,3-oxadiazol-4-yl, 1,2,3-oxadiazol-5-yl; 1,2,4-thiadiazol-2-yl, 1,2,4-thiadiazol-3-yl, 1,2,4-thiadiazol-5-yl, 1,2,3-thiadiazol-4-yl, 1,2,3-thiadiazol-5-yl; tetrazol-1-yl, tetrazol-2-yl, tetrazol-5-yl;

The compounds of formula I and their pharmaceutically acceptable salts can be manufactured according to the following methods:

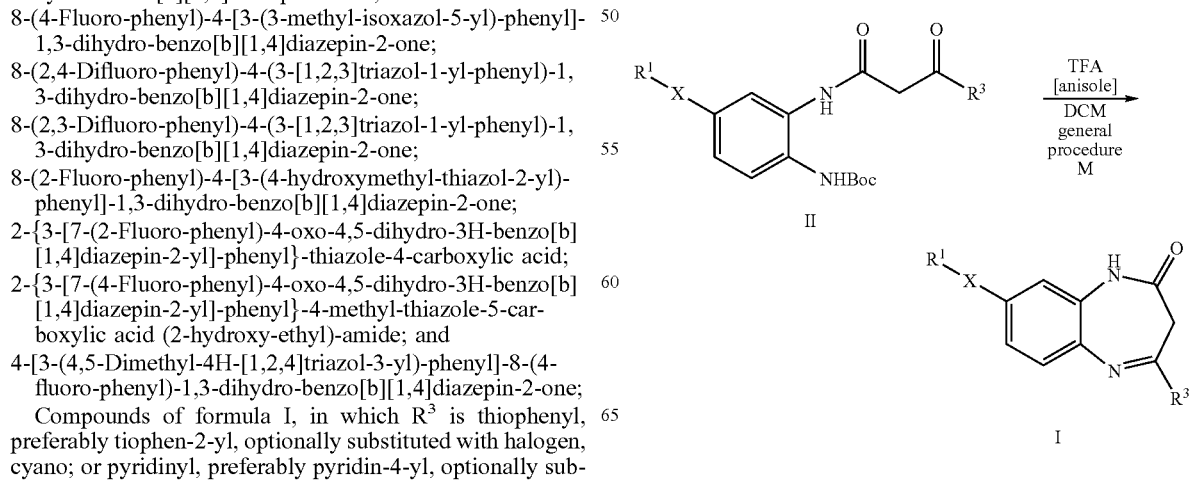

Scheme A

Compounds of formula I, in which $R^1$, $R^3$ and X are as described above can be prepared according to scheme A, by, for example, cleaving the BOC protecting group in compounds of formula II, and concomitant cyclization of the deprotected compound. The deprotection-cyclization step can be carried out by treating the compounds of formula II with a bronsted acid, like for example trifluoroacetic acid (TFA), in an inert solvent, like for example dichloromethane (DCM). The reaction is preferably carried out at temperatures between 0° C. and 50° C. It may be advantageous to use also anisole or 1,3-dimethoxybenzene as a carbocation scavenger in the reaction mixture. Any other suitable amino protecting group, such as e.g. Fmoc or benzyloxycarbonyl (Z), can be alternatively used instead of the BOC group.

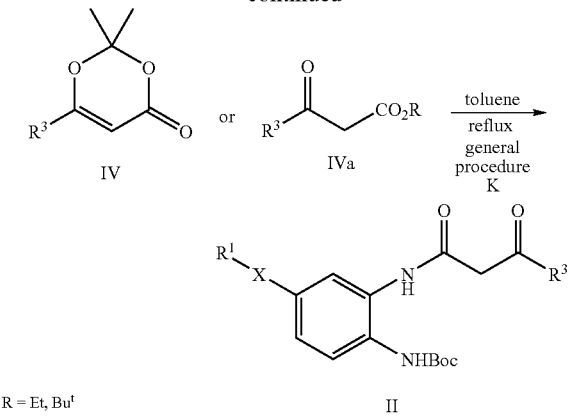

Compounds of formula II, in which $R^1$, $R^3$ and X are as described above, can be prepared according to scheme B by for example reacting a compound of formula III with a dioxinone (formula IV) in an inert solvent like for example toluene or xylene at elevated temperatures, preferably between 80° C. and 160° C.

Alternatively, compounds of formula II can also be prepared by for example reaction of a compound of formula III with a β-ketoester (formula IVa), in which $R^3$ is as described above using the same conditions as described for the reaction with the dioxinones.

Scheme B

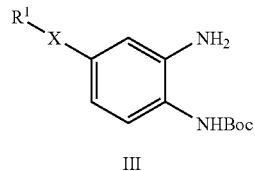

Scheme C

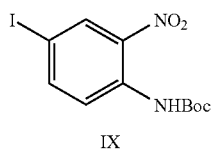

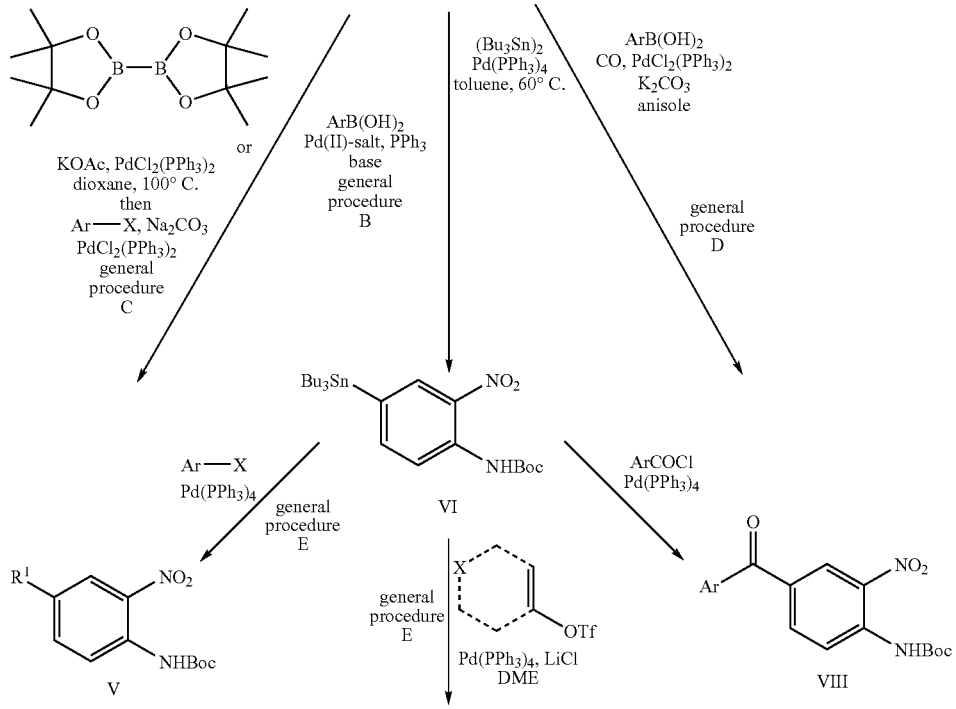

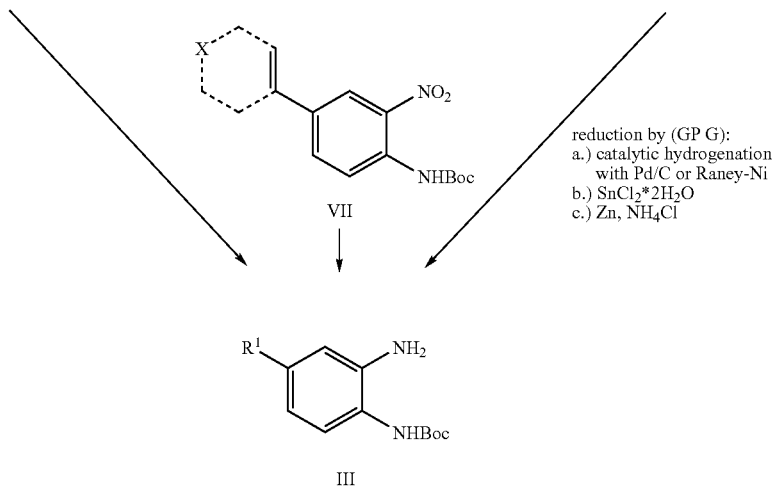

According to scheme C, compounds of formula III in which $R^1$ is as described above for compounds where X is a single bond can be prepared by different routes from the iodo-compound IX, depending on the nature of $R^1$. As shown in scheme C, the key steps are coupling reactions of Suzuki- and Stille-type in presence or absence of carbonmonoxide. The exact conditions for the respective compounds can be found in the experimental part.

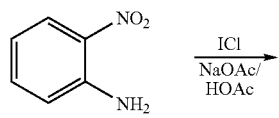

Scheme D

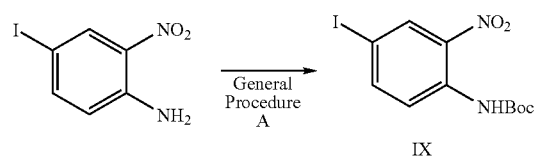

GP A, method a: diphosgene, EtOAc, 77° C.; then t-BuOH
GP A, method b: Boc$_2$O, Cs$_2$CO$_3$, 2-butanone, 52° C.
GP A, method c: i) Boc$_2$O, DMAP, THF; ii) TFA, DCM, 0° C.

According to scheme D, the key intermediate iodide IX can be prepared from commercially available 2-nitroaniline by a standard iodination-protection sequence.

Scheme E

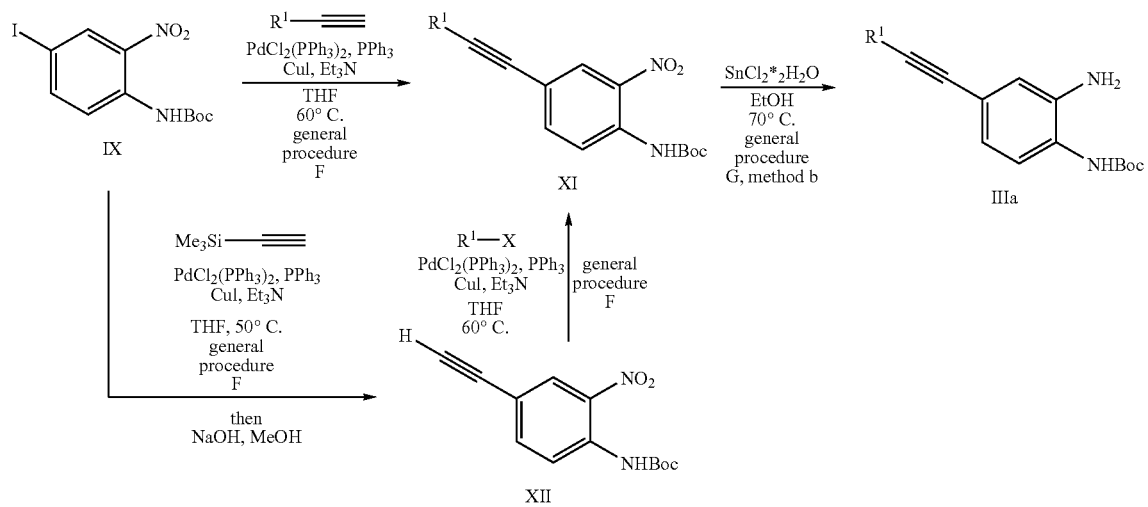

According to scheme E, compounds of formula IIIa in which $R^1$ is as described above for compounds where X is an ethynediyl group can be prepared by different routes from the iodo-compound IX, depending on the nature of $R^1$. As shown in Scheme E, the transformation can for example be carried out by directly attaching the $R^1$-alkynediyl-substituent via a Sonogashira-type coupling followed by the reduction of the nitro group or b) by two stepwise Sonogashira-type couplings, in which first trimethylsilyl-acetylene is coupled to iodide IX to yield, after deprotection with sodium hydroxide in methanol, the intermediate XII which then can be transformed via a second Sonogashira-type coupling with the appropriate reactant $R^1$—I, $R^1$—Br or $R^1$—$OSO_2CF_3$ and reduction of the nitro group to the desired compounds.

The exact conditions for the respective compounds can be found in the experimental part.

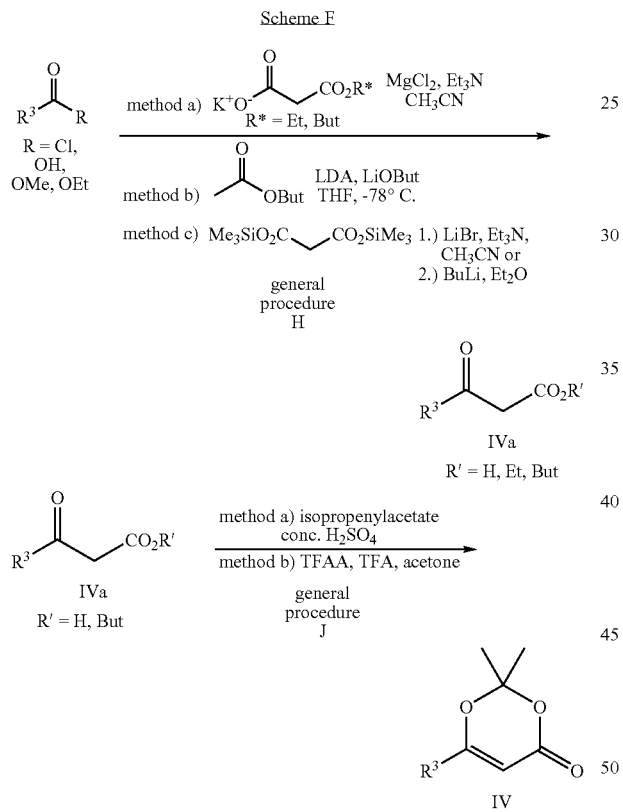

Scheme F

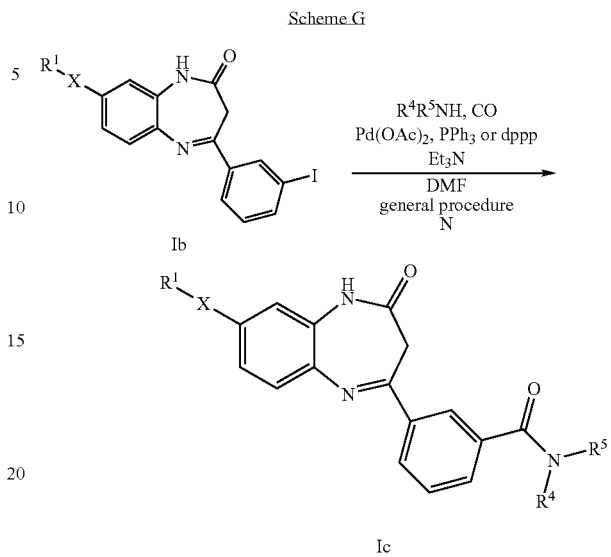

Scheme G

According to Scheme F, the dioxinones and β-keto esters building blocks with the formula IV and IVa can be prepared by methods known to someone skilled in the art from the corresponding carboxylic acid derivatives $R^3$—COR, i.e. free acids, methyl or ethyl esters and acid chlorides. The exact conditions for the corresponding compounds can be found in the experimental part.

Another synthetic route to prepare compounds of formula Ic, in which $R^1$ and X have the meaning as described above and $R^3$ is a phenyl-carboxamide of formula $C(O)NR^4R^5$, in which $R^4$ and $R^5$ are hydrogen, lower alkyl or $R^4$ and $R^5$ together form a morpholino-residue or a N-methyl-piperazine is outlined in scheme G:

The exact conditions for the respective compounds can be found in the experimental part.

Still another way to prepare compounds of formula I is the reaction of 4-aryl-8-iodo-1,3-dihydro-benzo[b][1,4]diazepin-2-ones (Formula Id, Synthetic Scheme H) with alkynes of formula $R^1$—C≡C—, in which $R^1$ has the meaning as described above, in a Sonogashira-coupling.

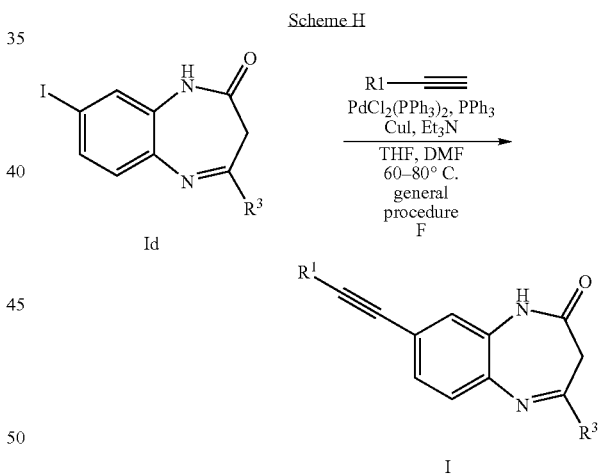

The exact conditions for the respective compounds can be found in the experimental part.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The compounds of formula I and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing one or more compounds of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The present invention relates also to the use of compounds of formula I and of pharmaceutically acceptable salts thereof for the production of medicaments, especially for the control or prevention of acute and/or chronic neurological disorders of the aforementioned kind.

The compounds of the present invention are group II mGlu receptor antagonists as determined using the assay described by Cartmell et al. (Br. J. Pharmacol. 1998, 123(3), 497–504).

The compounds show activities, as measured in the assay described below, of 50 μM or less, typically 3 μM or less, and ideally of 0.5 μM or less. In the table below are described some specific pKi values of preferred compounds

| Compound | Ki mGlu2 (μM) |
|---|---|
| 3-(7-Iodo-4-oxo-4,5-dihydro-3H-benzo[b][1,4]diazepin-2-yl)-benzonitrile | 0.017 |
| 4-(3-Chloro-phenyl)-8-phenylethynyl-1,3-dihydro-benzo[b][1,4]diazepin-2-one | 0.040 |
| 4-(3-Imidazol-1-yl-phenyl)-8-phenylethynyl-1,3-dihydro-benzo[b][1,4]diazepin-2-one | 0.006 |
| 3-[7-(4-Fluoro-phenyl)-4-oxo-4,5-dihydro-3H-benzo[b][1,4]diazepin-2-yl]-benzonitrile | 0.055 |
| 8-(4-Fluoro-phenylethynyl)-4-(3-imidazol-1-yl-phenyl)-1,3-dihydro-benzo[b][1,4]diazepin-2-one | 0.004 |
| 8-(4-Fluoro-phenylethynyl)-4-(3-[1,2,4]triazol-1-yl-phenyl)-1,3-dihydro-benzo[b][1,4]diazepin-2-one | 0.049 |
| 8-(4-Fluoro-phenylethynyl)-4-(2-imidazol-1-yl-pyridin-4-yl)-1,3-dihydro-benzo[b][1,4]diazepin-2-one | 0.004 |
| 8-(4-Fluoro-phenyl)-4-[3-(4-methyl-imidazol-1-yl)-phenyl]-1,3-dihydro-benzo[b][1,4]diazepin-2-one | 0.016 |
| 8-(4-Fluoro-2-methyl-phenyl)-4-(3-imidazol-1-yl-phenyl)-1,3-dihydro-benzo[b][1,4]diazepin-2-one | 0.050 |
| 8-(4-Fluoro-2-hydroxy-phenyl)-4-(3-imidazol-1-yl-phenyl)-1,3-dihydro-benzo[b][1,4]diazepin-2-one | 0.170 |
| 2-[7-(4-Fluoro-phenyl)-4-oxo-4,5-dihydro-1H-benzo[b][1,4]diazepin-2-yl]-thiophene-3-carbonitrile | 0.250 |
| 8-(4-Fluoro-phenylethynyl)-4-(3-tetrazol-1-yl-phenyl)-1,3-dihydro-benzo[b][1,4]diazepin-2-one | 0.036 |
| 4-(4-Oxo-7-phenylethynyl-4,5-dihydro-3H-benzo[b][1,4]diazepin-2-yl)-pyridine-2-carbonitrile | 0.039 |
| 4-[7-(2,4-Difluoro-phenyl)-4-oxo-4,5-dihydro-3H-benzo[b][1,4]diazepin-2-yl]-pyridine-2-carbonitrile | 0.026 |
| 8-(2-Fluoro-phenyl)-4-(3-[1,2,3]triazol-1-yl-phenyl)-1,3-dihydro-benzo[b][1,4]diazepin-2-one | 0.008 |
| 8-(4-Fluoro-phenyl)-4-[3-(3-methyl-isoxazol-5-yl)-phenyl]-1,3-dihydro-benzo[b][1,4]diazepin-2-one | 0.289 |
| 8-(2,4-Difluoro-phenyl)-4-(3-[1,2,3]triazol-1-yl-phenyl)-1,3-dihydro-benzo[b][1,4]diazepin-2-one | 0.010 |
| 8-(2-Fluoro-phenyl)-4-(2-imidazol-1-yl-thiazol-4-yl)-1,3-dihydro-benzo[b][1,4]diazepin-2-one | 0.298 |
| 8-(2,3-Difluoro-phenyl)-4-(3-[1,2,3]triazol-1-yl-phenyl)-1,3-dihydro-benzo[b][1,4]diazepin-2-one | 0.013 |
| 8-(2-Fluoro-phenyl)-4-[3-(4-hydroxymethyl-thiazol-2-yl)-phenyl]-1,3-dihydro-benzo[b][1,4]diazepin-2-one. | 0.016 |
| 2-{3-[7-(2-Fluoro-phenyl)-4-oxo-4,5-dihydro-3H-benzo[b][1,4]diazepin-2-yl]-phenyl}-thiazole-4-carboxylic acid. | 0.016 |
| 2-{3-[7-(4-Fluoro-phenyl)-4-oxo-4,5-dihydro-3H-benzo[b][1,4]diazepin-2-yl]-phenyl}-4-methyl-thiazole-5-carboxylic acid (2-hydroxy-ethyl)-amide | 0.049 |
| 4-[3-(4,5-Dimethyl-4H-[1,2,4]triazol-3-yl)-phenyl]-8-(4-fluoro-phenyl)-1,3-dihydro-benzo[b][1,4]diazepin-2-one | 0.108 |

[³H]-LY354740 Binding on mGlu2 Transfected CHO Cell Membranes

Transfection and Cell Culture cDNA encoding the rat mGlu2 receptor protein in pBluescript II was obtained from Prof. S. Nakanishi (Kyoto, Japan), and subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco BRL (Basel, Switzerland). Selection was made in the presence of G-418 (1000 ug/ml final). Clones were identified by reverse transcription of 5 μg total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM $(NH_4)_2SO_4$, 2 mM $MgCl_2$, 25 units/ml Taq Polymerase with 30 cycles annealing at 60° C. for 1 min., extension at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[³H]-LY354740 Binding

After thawing, the membranes were resuspended in cold 50 mM Tris-HCl buffer containing 2 mM $MgCl_2$ and 2 mM $CaCl_2$, (pH 7) (binding buffer). The final concentration of the membranes in the assays was 25 μg protein/ml. Inhibition experiments were performed with membranes incubated with 10 nM [³H]-LY354740 at room temperature, for 1 hour, in presence of various concentrations of the compound to be tested. Following the incubations, membranes were filtered onto Whatmann GF/C glass fiber filters and washed 5 times with cold binding buffer. Non specific binding was measured in the presence of 10 μM DCG IV (TOCRIS No. 0975). After transfer of the filters into plastic vials containing 10 ml of Ultima-gold scintillation fluid (Packard, Zürich, Switzerland), the radioactivity was measured by liquid scintillation in a Tri-Carb 2500 TR counter (Packard, Zürich, Switzerland).

Data Analysis.

The inhibition curves were fitted with a four parameter logistic equation giving IC50 values, and Hill coefficients.

EXAMPLES

General Procedure A (Synthetic Scheme D):

Preparation of (4-iodo-2-nitro-phenyl)-carbamic acid tert.-butyl esters from 4-iodo-2-nitroanilines.

Method a

To a solution of diphosgene (4.1 mL, 34.1 mmol) in EtOAc (40 mL) at 0° C. was added a solution of the 4-iodo-2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 4-iodo-2-nitrophenylisocyanate as a yellow solid. This material was refluxed in a mixture of excess tert.-BuOH in $CH_2Cl_2$ for 2.5 h. Removal of the solvent left an orange solid which was purified by silica gel column chromatography with hexane/EtOAc to give the (4-iodo-2-nitro-phenyl)-carbamic acid tert.-butyl ester as a yellow solid.

Method b

To a mixture of the 4-iodo-2-nitroaniline (142 mmol) and cesium carbonate (55.5 g, 170 mmol) in 2-butanone (740 mL) was dropwise added a solution of $Boc_2O$ (37.8 g, 173 mmol) in 2-butanone (170 mL) and the resulting mixture was stirred at 52° C. for 26 h. The solvent was removed in vacuum, the residue was treated with a mixture of $H_2O$ (240 mL) and MeOH (240 mL) and extracted with hexane (3×500 mL). The combined hexane layer was washed with brine (200 mL) and all aqueous layers were reextracted with hexane (300 mL). All combined hexane layers were dried over $MgSO_4$, filtered and the solvent was removed in vacuum to give an orange solid, which was purified by silica gel column chromatography with hexane/EtOAc to give the (4-iodo-2-nitro-phenyl)-carbamic acid tert.-butyl ester as a yellow solid.

Method c

To a solution of the 4-iodo-2-nitroaniline (550 mmol) and DMAP (1.22 g, 10 mmol) in THF (1000 mL) at 23° C. was dropwise added within 70 min a solution of $Boc_2O$ (246 g, 1128 mmol) in THF (500 mL) and stirring was continued at 23° C. for 75 min. The entire mixture was evaporated to dryness and dried at HV to leave a dark brown solid (253.59 g). This material was dissolved in DCM (1100 mL), cooled to 0° C. and TFA (84 mL, 1100 mmol) was added dropwise. The mixture was stirred at 0° C. for 2 h, poured into icecold sat. NaHCO3-sol., extracted with DCM, washed with brine and dried over $MgSO_4$. Removal of the solvent in vacuum left a dark brown solid (199.71 g) which was coated on silica gel and purified by silica gel column chromatography with hexane/EtOAc to give the (4-iodo-2-nitro-phenyl)-carbamic acid tert.-butyl ester as a yellow solid.

Example A1

(4-Iodo-2-nitro-phenyl)-carbamic acid tert.-butyl ester

Prepared the isocyanate from 4-iodo-2-nitroaniline (12.0 g, 45.5 mmol; prepared from 2-nitroaniline according to Wilson, J. Gerald; Hunt, Frederick C. Aust. *J. Chem.* 1983, 36, 2317–25; CAS-No. [20691-72-9]) with diphosgene (4.1 mL, 34.1 mmol) in EtOAc (250 mL), followed by treatment with tert.-BuOH (12 mL) in $CH_2Cl_2$ (60 mL) according to the general procedure A (method a). Obtained as a yellow solid (8.23 g, 82%). MS (EI) 390 (M⁺); mp 92–94° C.

Example A2

(4-Isopropyl-2-nitro-phenyl)-carbamic acid tert.-butyl ester

Prepared from 4-isopropyl-2-nitroaniline (CAS-No. [63649-64-9]) by reaction with $Boc_2O$ and cat. DMAP in THF, followed by treatment with TFA in CH$_2$Cl$_2$ according to the general procedure A (method c). Obtained as a yellow oil (14.1 g).

MS (EI) 280 (M$^+$).

Example A3

(4-Cyclopropyl-2-nitro-phenyl)-carbamic acid tert.-butyl ester

Prepared from 4-cyclopropyl-2-nitro-phenylamine prepared from nitration of N-(4-cyclopropyl-phenyl)-acetamide (CAS-No. [63649-64-9] with 65% HNO$_3$ in Ac$_2$O and subsequent saponification with 6N NaOH in refluxing dioxane) by reaction with Boc$_2$O and cat. DMAP in THF, followed by treatment with TFA in CH$_2$Cl$_2$ according to the general procedure A (method c). Obtained as an orange liquid (2.33 g).

MS (EI) 278 (M$^+$).

General Procedure B (Synthetic Scheme C)

Preparation of (4-aryl-2-nitro-phenyl)-carbamic acid tert.-butyl esters by direct Suzuki-coupling of (4-iodo-2-nitro-phenyl)-carbamic acid tert.-butyl esters with arylboronic acids.

A mixture of the (4-iodo-2-nitro-phenyl)-carbamic acid tert.-butyl ester (3.0 mmol), the arylboronic acid (4.5 mmol) and PdCl$_2$(PPh$_3$)$_2$ (2 mol %) was refluxed in 1,4-dioxane (25 mL) and 2M Na$_2$CO$_3$-sol. (7.5 mL) [or alternatively with 1M NaHCO$_3$-sol. (7.5 mL), LiCl (6.0 mmol) and (Ph$_3$P)$_4$Pd (3 mol %) in DME (30 mL); also possible with Et$_3$N (9.0 mmol), Pd(OAc)$_2$ (3 mol %), PPh$_3$ (6 mol %) in DMF (10 mL) at 100° C.] until tlc indicated complete conversion of the iodide. The mixture was transferred into a separating funnel, H$_2$O (25 mL) was added and the product was extracted with ether or EtOAc (3×30 mL). The combined organic layers were washed with brine (50 mL) and dried over Na$_2$SO$_4$. Removal of the solvent left a brown residue, which was purified by silica gel column chromatography with cyclohexane/ether or cyclohexane/EtOAc to give the title compound.

Example B1

(4'-Methoxy-3-nitro-biphenyl-4-yl)-carbamic acid tert.-butyl ester

Prepared from (4-iodo-2-nitro-phenyl)-carbamic acid tert.-butyl ester (Example A1) and 4-methoxyphenylboronic acid according to the general procedure B. Obtained as a yellow solid (637 mg).

MS (ISN) 343 [(M–H)$^-$]; mp 107–109° C.

Example B2

(2-Nitro-4-thiophen-3-yl-phenyl)-carbamic acid tert.-butyl ester

Prepared from (4-iodo-2-nitro-phenyl)-carbamic acid tert.-butyl ester (Example A1) and 3-thiopheneboronic acid according to the general procedure B. Obtained as a yellow solid (326 mg).

MS (ISN) 319 [(M–H)$^-$].

Example B3

(4-Furan-2-yl-2-nitro-phenyl)-carbamic acid tert.-butyl ester

Prepared from (4-iodo-2-nitro-phenyl)-carbamic acid tert.-butyl ester (Example A1) and furan-2-boronic acid according to the general procedure B. Obtained as an orange solid (282 mg).

MS (EI) 304 (M$^+$); mp 169–172° C.

Example B4

(4'-Ethyl-3-nitro-biphenyl-4-yl)-carbamic acid tert.-butyl ester

Prepared from (4-iodo-2-nitro-phenyl)-carbamic acid tert.-butyl ester (Example A1) and 4-ethylbenzene boronic acid according to the general procedure B. Obtained as an orange solid (689 mg).

MS (EI) 343 [(M+H)$^+$]; mp 94–99° C.

Example B5

(3-Nitro-biphenyl-4-yl)-carbamic acid tert.-butyl ester.

Prepared from (4-iodo-2-nitro-phenyl)-carbamic acid tert.-butyl ester (Example A1) (994 mg, 2.73 mmol) and phenyl boronic acid (576 mg, 3.00 mmol) according to the general procedure B. Obtained as a bright yellow solid (800 mg).

MS (EI) 314 (M$^+$); mp 119–121° C.

Example B6

(4-Furan-3-yl-2-nitro-phenyl)-carbamic acid tert.-butyl ester.

Prepared from (4-iodo-2-nitro-phenyl)-carbamic acid tert.-butyl ester (Example A1) and furan-3-boronic acid according to the general procedure B. Obtained as an orange solid (855 mg).

MS (ISP) 322 [(M+NH$_4$)$^+$] and 327 [(M+Na)$^+$]; mp 105–110° C.

Example B7

(4-Naphthalen-1-yl-2-nitro-phenyl)-carbamic acid tert.-butyl ester.

Prepared from (4-iodo-2-nitro-phenyl)-carbamic acid tert.-butyl ester (Example A1) and 1-naphthylboronic acid according to the general procedure B. Obtained as a yellow foam (1.0 g).

MS (ISN) 363 [(M–H)$^-$]; mp 60–66° C.

Example B8

(3'-Methoxy-3-nitro-biphenyl-4-yl)-carbamic acid tert.-butyl ester.

Prepared from (4-iodo-2-nitro-phenyl)-carbamic acid tert.-butyl ester (Example A1) and 3-methoxyphenylboronic acid according to the general procedure B. Obtained as an orange solid (818 mg).

MS (ISP) 345 [(M+H)⁺], 362 [(M+NH₄)⁺] and 367 [(M+Na)⁺]; mp 104–107° C.

Example B9

(3-Nitro-4'-trifluoromethoxy-biphenyl-4-yl)-carbamic acid tert.-butyl ester.

Prepared from (4-iodo-2-nitro-phenyl)-carbamic acid tert.-butyl ester (Example A1) and 4-(trifluoromethoxy)benzene boronic acid according to the general procedure B. Obtained as an orange solid (569 mg).

MS (ISN) 397 [(M−H)⁻]; mp 145–147° C.

Example B10

(2'-Fluoro-3-nitro-biphenyl-4-yl)-carbamic acid tert.-butyl ester.

Prepared from (4-iodo-2-nitro-phenyl)-carbamic acid tert.-butyl ester (Example A1) and 2-fluorobenzene boronic acid according to the general procedure B. Obtained as a yellow solid (1.48 g).

MS (ISN) 331 [(M−H)⁻]; mp 131–133° C.

Example B11

(3'-Fluoro-3-nitro-biphenyl-4-yl)-carbamic acid tert.-butyl ester.

Prepared from (4-iodo-2-nitro-phenyl)-carbamic acid tert.-butyl ester (Example A1) and 3-fluorobenzene boronic acid according to the general procedure B. Obtained as a yellow solid (3.87 g).

MS (ISN) 331 [(M−H)⁻]; mp 93–96° C.

Example B12

(4'-Fluoro-3-nitro-biphenyl-4-yl)-carbamic acid tert.-butyl ester.

Prepared from (4-iodo-2-nitro-phenyl)-carbamic acid tert.-butyl ester (Example A1) and 4-fluorobenzene boronic acid according to the general procedure B. Obtained as a yellow solid (1.08 g).

MS (ISN) 331 [(M−H)⁻]; mp 155–167° C.

Example B13

(4'-Fluoro-2'-methyl-3-nitro-biphenyl-4-yl)-carbamic acid tert.-butyl ester.

Prepared from (4-iodo-2-nitro-phenyl)-carbamic acid tert.-butyl ester (Example A1) and 4-fluoro-2-methylbenzene boronic acid [CAS-no. 139911-29-8; prepared from 2-bromo-5-fluorotoluene by reaction with n-BuLi at −78° C. followed by treatment with B(OMe)₃ and subsequent hydrolysis] according to the general procedure B. Obtained as a yellow solid (1.71 g).

MS (EI) 346 (M⁺).

Example B14

(4'-Fluoro-2'-methoxymethoxy-3-nitro-biphenyl-4-yl)-carbamic acid tert.-butyl ester.

Prepared from (4-iodo-2-nitro-phenyl)-carbamic acid tert.-butyl ester (Example A1) and 4-fluoro-2-methoxymethoxybenzene boronic acid [prepared from 1-bromo-4-fluoro-2-(methoxymethoxy)benzene (CAS-no. 162269-78-5) by reaction with n-BuLi at −78° C. followed by treatment with B(OMe)₃ and subsequent hydrolysis] according to the general procedure B. Obtained as a yellow solid (0.96 g).

MS (EI) 392 (M⁺).

Example B15

(2',4'-Difluoro-3-nitro-biphenyl-4-yl)-carbamic acid tert.-butyl ester.

Prepared from (4-iodo-2-nitro-phenyl)-carbamic acid tert.-butyl ester (Example A1) and 2,4-difluorobenzene boronic acid according to the general procedure B. Obtained as a yellow solid (3.26 g).

MS (ISN) 349 [(M−H)⁻].

Example B16

(2'-Fluoro-6'-methoxy-3-nitro-biphenyl-4-yl)-carbamic acid tert.-butyl ester.

Prepared from (4-iodo-2-nitro-phenyl)-carbamic acid tert.-butyl ester (Example A1) and 2-fluoro-6-methoxybenzene boronic acid according to the general procedure B. Obtained as a yellow solid (0.95 g).

MS (ISN) 361 [(M−H)⁻]; mp 65–68° C.

Example B17

(2',5'-Difluoro-3-nitro-biphenyl-4-yl)-carbamic acid tert.-butyl ester.

Prepared from (4-iodo-2-nitro-phenyl)-carbamic acid tert.-butyl ester (Example A1) and 2,5-difluorobenzene boronic acid according to the general procedure B. Obtained as a yellow solid (2.85 g).

MS (ISN) 349 [(M−H)⁻]; mp 104° C.

Example B18

(4-Benzofuran-2-yl-2-nitro-phenyl)-carbamic acid tert.-butyl ester.

Prepared from (4-iodo-2-nitro-phenyl)-carbamic acid tert.-butyl ester (Example A1) and benzo[b]furan-2-boronic acid according to the general procedure B. Obtained as an orange solid (711 mg).

MS (EI) 354 (M⁺); mp 175–177° C.

Example B19

(2',3'-Difluoro-3-nitro-biphenyl-4-yl)-carbamic acid tert.-butyl ester.

Prepared from (4-iodo-2-nitro-phenyl)-carbamic acid tert.-butyl ester (Example A1) (3.64 g, 10 mmol) and 2,3- difluorobenzene boronic acid (2.35 g, 14.9 mmol) according to the general procedure B. Obtained as a yellow solid (3.22 g).

MS (ISN) 349 [(M−H)⁻]; mp 93° C.

General Procedure C (Synthetic Scheme C)

Preparation of (4-aryl-2-nitro-phenyl)-carbamic acid tert.-butyl esters by Suzuki-coupling of (4-iodo-2-nitro-phenyl)-carbamic acid tert.-butyl esters with bis(pinacolato)diboron and subsequent reaction with aryl halides.

A mixture of the (4-iodo-2-nitro-phenyl)-carbamic acid tert.-butyl ester (2.0 mmol), bis(pinacolato)diboron (2.2 mmol), KOAc (6.0 mmol) and $PdCl_2(PPh_3)_2$ (3 mol %) in 1,4-dioxane (25 mL) was stirred at 100° C. until tlc indicated complete conversion of the iodide [cf. *Tetr. Lett.* 1997, 38, 3841–3844]. After addition of the aryl halide (4.0 mmol), $PdCl_2(PPh_3)_2$ (3 mol %) and 2M $Na_2CO_3$-sol. (7.5 mL) the mixture was stirred at 100° C. until tlc indicated complete conversion of the intermediate boronic ester. The mixture was transferred into a separating funnel, $H_2O$ (30 mL) was added and the product was extracted with ether or EtOAc (3×50 mL). The combined organic layers were washed with brine (100 mL) and dried over $Na_2SO_4$. Removal of the solvent left a brown residue, which was purified by silica gel column chromatography with cyclohexane/ether or cyclohexane/EtOAc to give the title compound.

Example C1

(2'-Methoxy-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 2-iodoanisole according to the general procedure C. Obtained as a yellow solid (735 mg).

MS (EI) 344 (M⁺)

Example C2

(4'-Chloro-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 1-chloro-4-iodobenzene according to the general procedure C. Obtained as a yellow solid (779 mg).

MS (ISN) 347 [(M−H)⁻]; mp 150–155° C. (dec.).

Example C3

(2-Nitro-4-thiophen-2-yl-phenyl)-carbamic acid tert.-butyl ester

Prepared from (4-iodo-2-nitro-phenyl)-carbamic acid tert.-butyl ester (Example A1), bis(pinacolato)diboron and 2-iodothiophene according to the general procedure C. Obtained as a yellow solid (91 mg).

MS (ISN) 319 [(M−H)⁻].

Example C4

(4'-Methyl-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 4-iodotoluene according to the general procedure C. Obtained as an orange solid (542 mg).

MS (ISP) 346 [(M+NH₄)⁺] and 367 [(M+Na)⁺]; mp 105–108° C.

Example C5

(2-Nitro-4-pyridin-2-yl-phenyl)-carbamic acid tert.-butyl ester

Prepared from (4-iodo-2-nitro-phenyl)-carbamic acid tert.-butyl ester (Example A1), bis(pinacolato)diboron and 2-bromopyridine according to the general procedure C. Obtained as a yellow solid (407 mg).

MS (ISP) 316 [(M+H)⁺].

Example C6

(3'-Methyl-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 3-iodotoluene according to the general procedure C. Obtained as a yellow solid (524 mg).

MS (ISP) 346 (M⁺) and 674 [(2M+NH₄)⁺]; mp 83–85° C.

Example C7

(3',4'-Dichloro-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 3,4-dichloro-iodobenzene according to the general procedure C. Obtained as a yellow solid (540 mg).

MS (EI) 382 (M⁺).

Example C8

(2'-Chloro-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 1-chloro-2-iodobenzene according to the general procedure C. Obtained as a yellow oil (886 mg).

MS (ISN) 347 [(M−H)⁻].

Example C9

(2'-Methyl-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 2-iodotoluene according to the general procedure C. Obtained as a yellow oil (755 mg).

MS (ISN) 327 [(M−H)⁺⁻].

Example C10

(2-Nitro-4-pyridin-3-yl-phenyl)-carbamic acid tert.-butyl ester

Prepared from (4-iodo-2-nitro-phenyl)-carbamic acid tert.-butyl ester (Example A1), bis(pinacolato)diboron and 3-bromopyridine according to the general procedure C. Obtained as a yellow solid (587 mg).

MS (ISP) 316 [(M+H)$^+$]; mp 107–109° C.

Example C11

(2-Nitro-4-pyridin-4-yl-phenyl)-carbamic acid tert.-butyl ester

Prepared from (4-iodo-2-nitro-phenyl)-carbamic acid tert.-butyl ester (Example A1), bis(pinacolato)diboron and 4-bromopyridine according to the general procedure C. Obtained as a yellow solid (379 mg).

MS (ISP) 316 [(M+H)$^+$].

Example C12

(3"-Nitro-[1,1';4',1"]terphenyl-4"-yl)-carbamic acid tert.-butyl ester

Prepared from (4-iodo-2-nitro-phenyl)-carbamic acid tert.-butyl ester (Example A1), bis(pinacolato)diboron and 4-bromobiphenyl according to the general procedure C. Obtained as a yellow solid (1.29 g).

MS (EI) 390 (M$^+$).

Example C13

(4'-Cyano-3-nitro-biphenyl-4-yl)-carbamic acid tert.-butyl ester

Prepared from (4-iodo-2-nitro-phenyl)-carbamic acid tert.-butyl ester (Example A1), bis(pinacolato)diboron and 4-bromobenzonitrile according to the general procedure C. Obtained as a yellow solid (1.38 g).

MS (ISN) 338 [(M–H)$^-$].

General Procedure D (Synthetic Scheme C)

Preparation of (4-aroyl-2-nitro-phenyl)-carbamic acid tert.-butyl esters by carbonylative Suzuki-coupling of (4-iodo-2-nitro-phenyl)-carbamic acid tert.-butyl esters with aryl boronic acids A mixture of the (4-iodo-2-nitro-phenyl)-carbamic acid tert.-butyl ester (1.0 mmol), aryl boronic acid (1.1 mmol), K$_2$CO$_3$ (3.0 mmol) and PdCl$_2$(PPh$_3$)$_2$ (3 mol %) in anisole (6 mL) was stirred at 80° C. under a CO-atmosphere until tlc indicated complete conversion of the iodide [cf. *Tetr. Lett.* 1993, 34, 7595–7598]. The mixture was transferred into a separating funnel, H$_2$O (30 mL) was added and the product was extracted with EtOAc (2×100 mL). The combined organic layers were washed with brine (50 mL) and dried over Na$_2$SO$_4$. Removal of the solvent left a yellow residue, which was purified by silica gel column chromatography with or hexane/EtOAc to give the title compound.

Example D1

(4-Benzoyl-2-nitro-phenyl)-carbamic acid tert.-butyl ester

Prepared from (4-iodo-2-nitro-phenyl)-carbamic acid tert.-butyl ester (Example A1) (364 mg, 1.0 mmol) and phenylboronic acid (134 mg, 1.1 mmol) according to the general procedure D. Obtained as a yellow solid (242 mg).

MS (EI) 342 (M$^+$).

Example D2

(2-Nitro-4-tributylstannanyl-phenyl)-carbamic acid tert.-butyl ester

A solution of (4-iodo-2-nitro-phenyl)-carbamic acid tert.-butyl ester (Example A1) (3.64 g, 10 mmol), hexabutyldistannane (7.5 mL, 15 mmol) and (Ph$_3$P)$_4$Pd (116 mg, 0.1 mmol) in toluene (20 mL) was heated to 60° C. for 5 days [cf. *Bull. Chem. Soc. Jpn.* 1983, 56, 3855–3856]. The reaction mixture was diluted with toluene (150 mL), washed with aqueous KF-sol. (2×50 mL), brine and dried over MgSO$_4$. Removal of the solvent in vacuum left a brown oil, which was purified by silica gel column chromatography with hexane/ether 49:1 to give the (2-nitro-4-tributylstannanyl-phenyl)-carbamic acid tert.-butyl ester as a yellow liquid (3.8 g, 72%).

MS (EI) 467, 469, 471 [all (M-butyl)$^+$].

General Procedure E (Synthetic Scheme C)

Preparation of (4-aryl-2-nitro-phenyl)-carbamic acid tert.-butyl esters or (4-{alkenyl-, cycloalkenyl- or heterocycloalkenyl}-2-nitro-phenyl)-carbamic acid tert.-butyl esters by Stille-coupling of (2-nitro-4-tributylstannanyl-phenyl)-carbamic acid tert.-butyl ester with aryl halides or vinyl triflates or Stille-coupling of (4-iodo-2-nitrophenyl)-carbamic acid tert.-butyl ester with trialkylarylstannanes.

A mixture of (2-nitro-4-tributylstannanyl-phenyl)-carbamic acid tert.-butyl ester (Example D2) (525 mg, 1.0 mmol), aryl halide or vinyl triflate (0.95–6.0 mmol), anhydrous LiCl (126 mg, 3.0 mmol) and Pd(PPh$_3$)$_4$ (5 mol %) in DME (3 mL) was stirred at 100° C. under argon atmosphere until tlc indicated complete consumption of the stannane. The reaction was cooled to 23° C., stirred with sat. aqueous KF-sol. (5 mL) for 45 min, filtered through celite, washed with ether and the filtrate was dried over MgSO$_4$. Removal of the solvent in vacuum left a brown oil, which was purified by silica gel column chromatography with hexane/EtOAc to give the title compound.

Example E1

4-(4-tert.-Butoxycarbonylamino-3-nitro-phenyl)-3,6-dihydro-2H-pyridine-1-carboxylic acid tert.-butyl ester Prepared from (2-nitro-4-tributylstannanyl-phenyl)-carbamic acid tert.-butyl ester (Example D2) (3.18 g, 6.06 mmol) and 4-trifluoromethylsulfonyloxy-3,6-dihydro-2H-pyridine-1-carboxylic acid tert.-butyl ester (1.99 g, 6.0 mmol) [prepared from Boc-4-piperidone by treatment with LDA in THF at –78° C. followed by reaction with N-phenyl-bis(trifluoromethanesulfonimide) according to Wustrow et al. *Synthesis* 1991, 1993] according to the general procedure E. Obtained as an orange solid (1.304 g, 52%).

MS (ISP) 420 [(M+H)$^+$], 442 [(M+Na)$^+$] and 458 [(M+K)$^+$]; mp 85–87° C.

Example E2

(2-Nitro-4-thiazol-2-yl-phenyl)-carbamic acid tert.-butyl ester

Prepared from (2-nitro-4-tributylstannanyl-phenyl)-carbamic acid tert.-butyl ester (Example D2) (1.0 g, 1.9 mmol) and 2-bromothiazole (0.56 mL, 6.27 mmol) according to the general procedure E. Obtained as a yellow solid (160 mg).

MS (EI) 321 (M$^+$).

Example E3

[4-(6-Benzyloxy-pyridin-3-yl)-2-nitro-phenyl]-carbamic acid tert.-butyl ester

Prepared from (4-iodo-2-nitro-phenyl)-carbamic acid tert.-butyl ester (Example A1) (728 mg, 2.0 mmol) and 2-(phenylmethoxy)-5-(trimethylstannyl)-pyridine (766 mg, 2.2 mmol) [CAS-No. [188881-22-3], WO 9709311] according to the general procedure E. Obtained as a yellow solid (876 mg).
MS (ISP) 422 [(M+H)$^+$]; mp 119–122° C.

General Procedure F (Synthetic Scheme E):

Preparation of (4-alkynyl-2-nitro-phenyl)-carbamic acid tert.-butyl esters by Sonogashira-coupling of (4-iodo-2-nitro-phenyl)-carbamic acid tert.-butyl esters with acetylenic compounds; also Sonogashira-coupling of (4-ethynyl-2-nitro-phenyl)-carbamic acid tert.-butyl esters with aryl halides; and Sonogashira-coupling of 8-iodo-4-aryl-1,3-dihydro-benzo[b][1,4]diazepin-2-ones with acetylenic compounds.

A mixture of the halide (3.0–4.5 mmol), acetylenic compound (3.0–4.5 mmol), Et$_3$N (13.5 mmol), PdCl$_2$(PPh$_3$)$_2$ (5 mol %) and PPh$_3$ (2.5 mol %) in THF (12 mL) [with very insoluble material DMF (up to 12 mL) could be added] was stirred for 20 min at 23° C. while being purged with Argon. CuI (1.2 mol %) was added and stirring was continued at 60° C. under Argon atmosphere until tlc indicated complete conversion of the minor component [cf. *J. Org. Chem.* 1998, 63, 8551]. The mixture was transferred into a separating funnel, 5% citric acid (50 mL) was added and the product was extracted with EtOAc (2×100 mL). The combined organic layers were washed with sat. NaHCO$_3$-sol. (50 mL) and brine (50 mL), followed by drying over MgSO$_4$. Removal of the solvent left a yellow residue, which was purified by silica gel column chromatography with hexane/EtOAc and/or triturated with hexane or aqueous EtOH to give the title compound.

Example F1

(2-Nitro-4-trimethylsilanylethynyl-phenyl)-carbamic acid tert.-butyl ester

Prepared from (4-iodo-2-nitro-phenyl)-carbamic acid tert.-butyl ester (Example A1) (3.64 g, 10 mmol) and trimethylsilylacetylene (4.2 mL, 30 mmol) according to the general procedure F. Obtained as a green oil (3.6 g).
MS (EI) 334 (M$^+$).

Example F2

(4-Ethynyl-2-nitro-phenyl)-carbamic acid tert.-butyl ester

To a solution of (2-nitro-4-trimethylsilanylethynyl-phenyl)-carbamic acid tert.-butyl ester (Example F1) (3.54 g, 10.6 mmol) in MeOH (10 mL) and THF (20 mL) at 0° C. was added 1N NaOH (13 mL) and stirring was continued at 23° C. for 30 min. Poured into cold 5% citric acid, extracted with EtOAc (300 mL), washed with sat. NaHCO$_3$-sol. and brine, dried over MgSO$_4$. Removal of the solvent in vacuum left a dark brown oil, which was purified by silica gel column chromatography with hexane/EtOAc 19:1. Obtained as a yellow solid (2.4 g).
MS (EI) 262 (M$^+$); mp 102° C.

Example F3

(2-Nitro-4-phenylethynyl-phenyl)-carbamic acid tert.-butyl ester

Prepared from (4-iodo-2-nitro-phenyl)-carbamic acid tert.-butyl ester (Example A1) (5.64 g, 15 mmol) and phenylacetylene (2.47 mL, 22.5 mmol) according to the general procedure F. Obtained as a yellow solid (4.96 g).
MS (EI) 338 (M$^+$); mp 146–148° C.

Example F4

(2-Nitro-4-p-tolylethynyl-phenyl)-carbamic acid tert.-butyl ester

Prepared from (4-iodo-2-nitro-phenyl)-carbamic acid tert.-butyl ester (Example A1) (728 mg, 2.0 mmol) and 4-tolylacetylene (349 mg, 3.0 mmol) according to the general procedure F. Obtained as a yellow solid (632 mg).
MS (EI) 352 (M$^+$); mp 164–165° C.

Example F5

[4-(2-Chloro-phenylethynyl)-2-nitro-phenyl]-carbamic acid tert.-butyl ester

Prepared from (4-iodo-2-nitro-phenyl)-carbamic acid tert.-butyl ester (Example A1) (1.82 g, 5.0 mmol) and 2-chlorophenylacetylene (1.02 g, 7.5 mmol) according to the general procedure F. Obtained as a yellow solid (1.8 g).
MS (ISN) 371 [(M–H)–] and 373 [(M+2-H)–]; mp 152–155° C.

Example F6

[4-(4-Chloro-phenylethynyl)-2-nitro-phenyl]-carbamic acid tert.-butyl ester

Prepared from (4-iodo-2-nitro-phenyl)-carbamic acid tert.-butyl ester (Example A1) (728 mg, 2.0 mmol) and 4-chlorophenylacetylene (416 mg, 3.0 mmol) according to the general procedure F. Obtained as a yellow solid (658 mg).
MS (EI) 372 (M$^+$) and 374 [(M+2)$^+$]; mp 213–218° C.

Example F7

(2-Nitro-4-thiazol-2-ylethynyl-phenyl)-carbamic acid tert.-butyl ester

Prepared from (4-ethynyl-2-nitro-phenyl)-carbamic acid tert.-butyl ester (Example F2) (262 mg, 1.00 mmol) and 2-bromothiazole (0.14 mL, 1.50 mmol) according to the general procedure F. Obtained as a yellow solid (215 mg).
MS (ISN) 344 [(M–H)$^-$]; mp 137° C.

Example F8

(2-Nitro-4-pyridin-2-ylethynyl-phenyl)-carbamic acid tert.-butyl ester

Prepared from (4-ethynyl-2-nitro-phenyl)-carbamic acid tert.-butyl ester (Example F2) (262 mg, 1.0 mmol) and 2-bromopyridine (0.15 mL, 1.6 mmol) according to the general procedure F. Obtained as a yellow solid (293 mg).
MS (ISP) 340 [(M+H)$^+$]; mp 142–144° C.

Example F9

[4-(4-Fluoro-phenylethynyl)-2-nitro-phenyl]-carbamic acid tert.-butyl ester

Prepared from (4-ethynyl-2-nitro-phenyl)-carbamic acid tert.-butyl ester (Example F2) (525 mg, 2.0 mmol) and 1-fluoro-4-iodobenzene (0.35 mL, 3 mmol) according to the general procedure F. Obtained as a yellow solid (793 mg).
MS (ISN) 355 [(M−H)⁻]; mp 157–158° C.

Example F10

[4-(2-Fluoro-phenylethynyl)-2-nitro-phenyl]-carbamic acid tert.-butyl ester

Prepared from (4-ethynyl-2-nitro-phenyl)-carbamic acid tert.-butyl ester (Example F2) (525 mg, 2.0 mmol) and 2-fluoro-1-iodobenzene (0.35 mL, 3 mmol) according to the general procedure F. Obtained as a yellow solid (759 mg).
MS (ISN) 355 [(M−H)⁻]; mp 140–142° C.

Example F11

[4-(2,4-Difluoro-phenylethynyl)-2-nitro-phenyl]-carbamic acid tert.-butyl ester

Prepared from (4-ethynyl-2-nitro-phenyl)-carbamic acid tert.-butyl ester (Example F2) (525 mg, 2.0 mmol) and 2,4-difluoro-1-iodobenzene (0.36 mL, 3 mmol) according to the general procedure F. Obtained as a yellow solid (807 mg).
MS (ISN) 373 [(M−H)⁻]; mp 134–136° C.

Example F12

[2-Nitro-4-(4-trifluoromethoxy-phenylethynyl)-phenyl]-carbamic acid tert.-butyl ester Prepared from (4-ethynyl-2-nitro-phenyl)-carbamic acid tert.-butyl ester (Example F2) (701 mg, 2.67 mmol) and 1-iodo-4-(trifluoromethoxy)benzene (1.0 g, 3.47 mmol) according to the general procedure F. Obtained as a yellow solid (1.10 g).
MS (ISN) 421 [(M−H)⁻]; mp 129–131° C.

General Procedure G (Synthetic Scheme E)

Preparation of the (2-amino-phenyl)-carbamic acid tert.-butyl esters by reduction of (2-nitro-phenyl)-carbamic acid tert.-butyl esters; Also preparation of 4-aryl-1,3-dihydro-benzo[b][1,4]diazepin-2-ones by reduction and concomitant cyclization of 3-aryl-N-(2-nitro-phenyl)-3-oxo-propionamides.

Method a: Catalytic Hydrogenation

A mixture of the nitro compound (1.0 mmol) in MeOH or EtOH and THF (1:1 to 1:9 ca. 20 mL) and 10% Palladium on carbon (20 mg) or Raney-Ni (20 mg) was stirred vigorously at 23° C. under hydrogen atmosphere until tlc indicated complete conversion. The catalyst was filtered off, washed thoroughly with MeOH or EtOH and THF (1:1), the solvent was removed in vacuum to give the title compound, which was generally pure enough for further transformations.

Method b: Reduction with $SnCl_2 \cdot 2H_2O$

A mixture of the nitro compound (1.0 mmol) and $SnCl_2 \cdot 2H_2O$ (5.0 mmol) in EtOH (30 mL) was stirred at 70–80° C. under Argon atmosphere until tlc indicated complete conversion [cf. Tetr. Lett. 1984, 25, 839]. The reaction mixture was brought to pH 8 by addition of sat. $NaHCO_3$-sol. and extracted with EtOAc (2×100 mL). The combined organic layer were washed with brine and dried over $Na_2SO_4$. Removal of the solvent left a yellow solid, which—if necessary—can be purified by silica gel column chromatography.

Method c: Reduction with Zn and $NH_4Cl$

To a mixture of the nitro compound (1.0 mmol) in EtOH/THF/sat. $NH_4Cl$-sol. (1:1:1, 30 mL) was added Zinc dust (3.0 mmol) and the mixture was stirred at 70° C. under Argon atmosphere until tlc indicated complete conversion. Aqueous workup as described in method b.

Method d: Reduction with Fe and HOAc

To a mixture of the nitro compound (1.0 mmol) in $THF/H_2O$ (4:1, 10–50 mL) was added Fe powder (6.0 mmol), followed by HOAc (10–12 drops) and the mixture was stirred at 70° C. under Argon atmosphere until tlc indicated complete conversion. Aqueous workup as described in method b.

Example G1

(2-Amino-4-iodo-phenyl)-carbamic acid tert.-butyl ester

Prepared from (4-iodo-2-nitro-phenyl)-carbamic acid tert.-butyl ester (Example A1) (2.18 g, 6.0 mmol) by reduction with $SnCl_2 \cdot 2H_2O$ (6.77 g, 30 mmol) according to the general procedure G (method b). Obtained as a brown-yellow solid (2.0 g).
MS (EI) 334 (M⁺); mp 127–130° C.

Example G2

(2-Amino-4-phenylethynyl-phenyl)-carbamic acid tert.-butyl ester

Prepared from (2-nitro-4-phenylethynyl-phenyl)-carbamic acid tert.-butyl ester (Example F3) (403 mg, 1.19 mmol) by reduction with $SnCl_2 \cdot 2H_2O$ (1.34 g, 5.96 mmol) according to the general procedure G (method b). Obtained as an orange solid (237 mg).
MS (ISP) 309 [(M+H)⁺]; mp 177–178° C.

Example G3

(2-Amino-4-p-tolylethynyl-phenyl)-carbamic acid tert.-butyl ester

Prepared from (2-nitro-4-p-tolylethynyl-phenyl)-carbamic acid tert.-butyl ester (Example F4) (640 mg, 1.82 mmol) by reduction with $SnCl_2 \cdot 2H_2O$ (2.0 g, 9.1 mmol) according to the general procedure G (method b). Obtained as a beige solid (569 mg).
MS (ISP) 323 [(M+H)⁺]; mp 175° C.

Example G4

[2-Amino-4-(2-chloro-phenylethynyl)-phenyl]-carbamic acid tert.-butyl ester

Prepared from (4-(2-chloro-phenylethynyl)-2-nitro-phenyl)-carbamic acid tert.-butyl ester (Example F5) (1.61 g, 4.3 mmol) by reduction with $SnCl_2 \cdot 2H_2O$ (5.3 g, 23.5 mmol)

according to the general procedure G (method b). Obtained as a light brown solid (1.1 g).
MS (EI) 342 (M$^+$) and 344 [(M+2)$^+$]; mp 120–122° C.

Example G5

(3-Amino-4'-methoxy-biphenyl-4-yl)-carbamic acid tert.-butyl ester

Prepared from (4'-methoxy-3-nitro-biphenyl-4-yl)-carbamic acid tert.-butyl ester (Example B1) by catalytic hydrogenation with Raney-Ni according to the general procedure G (method a). Obtained as a white solid (77 mg).
MS (ISP) 315 [(M+H)$^+$] and 337 [(M+Na)$^+$].

Example G6

(2-Amino-4-thiophen-3-yl-phenyl)-carbamic acid tert.-butyl ester

Prepared from (2-nitro-4-thiophen-3-yl-phenyl)-carbamic acid tert.-butyl ester (Example B2) by catalytic hydrogenation with Raney-Ni according to the general procedure G (method a). Obtained as a white solid (278 mg).
MS (ISP) 291 [(M+H)$^+$].

Example G7

(2-Amino-4-furan-2-yl-phenyl)-carbamic acid tert.-butyl ester

Prepared from (4-furan-2-yl-2-nitrophenyl)-carbamic acid tert.-butyl ester (Example B3) by catalytic hydrogenation with Raney-Ni according to the general procedure G (method a). Obtained as a grey powder (212 mg).
MS (EI) 274 (M$^+$).

Example G8

(3-Amino-4'-ethyl-biphenyl-4-yl)-carbamic acid tert.-butyl ester

Prepared from (4'-ethyl-3-nitro-biphenyl-4-yl)-carbamic acid tert.-butyl ester (Example B4) by catalytic hydrogenation with Raney-Ni according to the general procedure G (method a). Obtained as a white solid (311 mg).
MS (ISP) 313 [(M+H)$^+$] and 335 [(M+Na)$^+$].

Example G9

(3-Amino-biphenyl-4-yl)-carbamic acid tert.-butyl ester

Prepared from (3-nitro-biphenyl-4-yl)-carbamic acid tert.-butyl ester (Example B5) (100 mg, 0.32 mmol) by catalytic hydrogenation with Pd/C according to the general procedure G (method a). Obtained as a white solid (85 mg).
MS (ISP) 285 [(M+H)$^+$]; mp 137° C.

Example G10

(3-Amino-2'-methoxy-biphenyl-4-yl)-carbamic acid tert.-butyl ester

Prepared from (2'-methoxy-3-nitro-biphenyl-4-yl)-carbamic acid tert.-butyl ester (Example C1) by catalytic hydrogenation with Raney-Ni according to the general procedure G (method a). Obtained as a white solid (169 mg).
MS (ISP) 315 [(M+H)$^+$].

Example G11

(2-Amino-4-furan-3-yl-phenyl)-carbamic acid tert.-butyl ester

Prepared from (4-furan-3-yl-2-nitrophenyl)-carbamic acid tert.-butyl ester (Example B6) by catalytic hydrogenation with Raney-Ni according to the general procedure G (method a). Obtained as a light brown solid. (744 mg).
MS (ISP) 275 [(M+H)$^+$] and 297 [(M+Na)$^+$]; mp 158–161° C. (dec.).

Example G12

(3-Amino-4'-chloro-biphenyl-4-yl)-carbamic acid tert.-butyl ester

Prepared from (4'-chloro-3-nitro-biphenyl-4-yl)-carbamic acid tert.-butyl ester (Example C2) by reduction with Zn/NH$_4$Cl according to the general procedure G (method c). Obtained as a green solid (162 mg).
MS (EI) 318 (M$^+$).

Example G13

[2-Amino-4-(4-chloro-phenylethynyl)-phenyl]-carbamic acid tert.-butyl ester

Prepared from (4-(4-chloro-phenylethynyl)-2-nitro-phenyl)-carbamic acid tert.-butyl ester (Example F6) (606 mg, 1.63 mmol) by reduction with SnCl$_2$.2H$_2$O (1.83 g, 8.1 mmol) according to the general procedure G (method b). Obtained as a beige solid (406 mg).
MS (ISP) 343 [(M+H)$^+$] and 345 [(M+2+H)$^+$]; mp 170–173° C.

Example G14

(2-Amino-4-naphthalen-1-yl-phenyl)-carbamic acid tert.-butyl ester.

Prepared from (4-naphthalen-1-yl-2-nitro-phenyl)-carbamic acid tert.-butyl ester (Example B7) by catalytic hydrogenation with Raney-Ni according to the general procedure G (method a). Obtained as a white solid (226 mg).
MS (EI) 334 (M$^+$).

Example G15

(2-Amino-4-thiazol-2-ylethynyl-phenyl)-carbamic acid tert.-butyl ester

Prepared from (2-nitro-4-thiazol-2-ylethynyl-phenyl)-carbamic acid tert.-butyl ester (Example F7) (205 mg, 0.59 mmol) by reduction with SnCl$_2$.2H$_2$O (668 mg, 2.95 mmol) according to the general procedure G (method b). Obtained as a yellow solid (108 mg).
MS (ISP) 316 [(M+H)$^+$]; mp 182° C.

Example G16

(3-Amino-4'-methyl-biphenyl-4-yl)-carbamic acid tert.-butyl ester

Prepared from (4'-methyl-3-nitro-biphenyl-4-yl)-carbamic acid tert.-butyl ester (Example C4) by catalytic hydrogenation with Pd/C according to the general procedure G (method a). Obtained as a white solid (125 mg).
MS (ISP) 299 [(M+H)$^+$], 321 [(M+Na)$^+$] and 337 [(M+K)$^+$].

Example G17

(2-Amino-4-pyridin-2-yl-phenyl)-carbamic acid tert.-butyl ester

Prepared from (2-nitro-4-pyridin-2-yl-phenyl)-carbamic acid tert.-butyl ester (Example C5) by catalytic hydrogenation with Raney-Ni according to the general procedure G (method a). Obtained as a light brown solid (339 mg).
MS (ISP) 286 [(M+H)$^+$] and 308 [(M+Na)$^+$].

Example G18

(2-Amino-4-thiophen-2-yl-phenyl)-carbamic acid tert.-butyl ester

Prepared from (2-nitro-4-thiophen-2-yl-phenyl)-carbamic acid tert.-butyl ester (Example C3) by catalytic hydrogenation with Pd/C according to the general procedure G (method a). Obtained as a beige powder (151 mg).
MS (ISP) 291 [(M+H)$^+$].

Example G19

(2-Amino-4-pyridin-2-ylethynyl-phenyl)-carbamic acid tert.-butyl ester

Prepared from (2-nitro-4-pyridin-2-ylethynyl-phenyl)-carbamic acid tert.-butyl ester (Example F8) (262 mg, 0.772 mmol) by reduction with SnCl$_2$.2H$_2$O (871 mg, 3.86 mmol) according to the general procedure G (method b). Obtained as a light brown solid (130 mg).
MS (EI) 309 (M$^+$); mp 178° C.

Example G20

(3-Amino-3'-methyl-biphenyl-4-yl)-carbamic acid tert.-butyl ester

Prepared from (3'-methyl-3-nitro-biphenyl-4-yl)-carbamic acid tert.-butyl ester (Example C6) by catalytic hydrogenation with Raney-Ni according to the general procedure G (method a). Obtained as a white powder (212 mg).
MS (EI) 298 (M$^+$).

Example G21

(3-Amino-3',4'-dichloro-biphenyl-4-yl)-carbamic acid tert.-butyl ester

Prepared from (3',4'-dichloro-3-nitro-biphenyl-4-yl)-carbamic acid tert.-butyl ester (Example C7) by catalytic hydrogenation with Raney-Ni according to the general procedure G (method a). Obtained as a white solid (485 mg).
MS (ISP) 353 (M$^+$); mp 168–171° C.

Example G22

(3-Amino-2'-chloro-biphenyl-4-yl)-carbamic acid tert.-butyl ester

Prepared from (2'-chloro-3-nitro-biphenyl-4-yl)-carbamic acid tert.-butyl ester (Example C8) by catalytic hydrogenation with Raney-Ni according to the general procedure G (method a). Obtained as a white solid (180 mg).
MS (ISP) 319 [(M+H)$^+$], 341 [(M+Na)$^+$] and 357 [(M+K)$^+$].

Example G23

(3-Amino-2'-methyl-biphenyl-4-yl)-carbamic acid tert.-butyl ester

Prepared from (2'-methyl-3-nitro-biphenyl-4-yl)-carbamic acid tert.-butyl ester (Example C9) by catalytic hydrogenation with Raney-Ni according to the general procedure G (method a). Obtained as a white powder (281 mg).
MS (ISP) 299 [(M+H)$^+$], 321 [(M+Na)$^+$] and 337 [(M+K)$^+$].

Example G24

(2-Amino-4-benzoyl-phenyl)-carbamic acid tert.-butyl ester

Prepared from (4-benzoyl-2-nitro-phenyl)-carbamic acid tert.-butyl ester (Example D1) (280 mg, 0.82 mmol) by catalytic hydrogenation with Raney-Ni according to the general procedure G (method a). Obtained as a yellow foam (269 mg).
MS (ISP) 313 [(M+H)$^+$].

Example G25

(3-Amino-3'-methoxy-biphenyl-4-yl)-carbamic acid tert.-butyl ester

Prepared from (3'-methoxy-3-nitro-biphenyl-4-yl)-carbamic acid tert.-butyl ester (Example B8) by catalytic hydrogenation with Raney-Ni according to the general procedure G (method a). Obtained as a white solid (165 mg).
MS (ISP) 315 [(M+H)$^+$].

Example G26

(2-Amino-4-pyridin-3-yl-phenyl)-carbamic acid tert.-butyl ester

Prepared from (2-nitro-4-pyridin-3-yl-phenyl)-carbamic acid tert.-butyl ester (Example C10) by catalytic hydrogenation with Raney-Ni according to the general procedure G (method a). Obtained as a grey powder (200 mg).
MS (ISP) 286 [(M+H)$^+$].

Example G27

(3-Amino-4'-trifluoromethoxy-biphenyl-4-yl)-carbamic acid tert.-butyl ester

Prepared from (3-nitro-4'-trifluoromethoxy-biphenyl-4-yl)-carbamic acid tert.-butyl ester (Example B9) by catalytic hydrogenation with Raney-Ni according to the general procedure G (method a). Obtained as a white solid (371 mg).
MS (ISP) 369 [(M+H)$^+$] and 391 [(M+Na)$^+$].

Example G28

(2-Amino-4-pyridin-4-yl-phenyl)-carbamic acid tert.-butyl ester.

Prepared from (2-nitro-4-pyridin-4-yl-phenyl)-carbamic acid tert.-butyl ester (Example C11) by catalytic hydrogenation with Raney-Ni according to the general procedure G (method a). Obtained as a light grey powder (305 mg).
MS (ISP) 286 [(M+H)$^+$].

Example G29

4-(3-Amino-4-tert.-butoxycarbonylamino-phenyl)-3, 6-dihydro-2H-pyridine-1-carboxylic acid tert.-butyl ester Prepared from 4-(4-tert.-butoxycarbonylamino-3-nitro-phenyl)-3,6-dihydro-2H-pyridine-1-carboxylic acid tert.-butyl ester (Example E1) (256 mg, 0.61 mmol) by reduction with Zn/NH$_4$Cl according to the general procedure G (method c). Obtained as an orange foam (75 mg).
MS (EI) 389 (M$^+$).

Example G30

[2-Amino-4-(6-benzyloxy-pyridin-3-yl)-phenyl]-carbamic acid tert.-butyl ester

Prepared from [4-(6-benzyloxy-pyridin-3-yl)-2-nitro-phenyl]-carbamic acid tert.-butyl ester (Example E3) (768 mg, 1.82 mmol) by reduction with Zn/NH$_4$Cl according to the general procedure G (method c). Obtained as a light brown solid (678 mg).
MS (ISP) 392 [(M+H)$^+$]; mp 176–177° C.

Example G31

[2-Amino-4-(6-oxo-1,6-dihydro-pyridin-3-yl)-phenyl]-carbamic acid tert.-butyl ester Prepared from [2-amino-4-(6-benzyloxy-pyridin-3-yl)-phenyl]-carbamic acid tert.-butyl ester (Example G30) (160 mg, 0.409 mmol) by catalytic hydrogenation with Pd/C according to the general procedure G (method a). Obtained as an off-white solid (136 mg).
MS (ISP) 302 [(M+H)$^+$]; mp 120–124° C. (dec.).

Example G32

(3"-Amino-[1,1';4',1"]terphenyl-4"-yl)-carbamic acid tert.-butyl ester

Prepared from (3"-nitro-[1,1';4',1"]terphenyl-4"-yl)-carbamic acid tert.-butyl ester (Example C12) (160 mg, 0.409 mmol) by catalytic hydrogenation with Pd/C according to the general procedure G (method a). Obtained as a beige solid (175 mg).
MS (ISP) 361 [(M+H)$^+$]; mp 206–207° C.

Example G33

[2-Amino-4-(4-fluoro-phenylethynyl)-phenyl]-carbamic acid tert.-butyl ester

Prepared from [4-(4-fluoro-phenylethynyl)-2-nitro-phenyl]-carbamic acid tert.-butyl ester (Example F9) (10.0 g, 28.1 mmol) by reduction with SnCl$_2$.2H$_2$O (31.7 g, 140.5 mmol) according to the general procedure G (method b). Obtained as a yellow solid (7.08 g).
MS (ISP) 327 [(M+H)$^+$]; mp 180° C.

Example G34

[2-Amino-4-(2-fluoro-phenylethynyl)-phenyl]-carbamic acid tert.-butyl ester

Prepared from [4-(2-fluoro-phenylethynyl)-2-nitro-phenyl]-carbamic acid tert.-butyl ester (Example F10) (713 mg, 2 mmol) by reduction with SnCl$_2$.2H$_2$O (2.26 g, 10 mmol) according to the general procedure G (method b). Obtained as an orange solid (757 mg).
MS (ISP) 327 [(M+H)$^+$]; mp 137–139° C.

Example G35

[2-Amino-4-(2,4-difluoro-phenylethynyl)-phenyl]-carbamic acid tert.-butyl ester

Prepared from [4-(2,4-difluoro-phenylethynyl)-2-nitro-phenyl]-carbamic acid tert.-butyl ester (Example F11) (750 mg, 2 mmol) by reduction with SnCl$_2$.2H$_2$O (2.26 g, 10 mmol) according to the general procedure G (method b). Obtained as a brown solid (688 mg).
MS (ISP) 345 [(M+H)$^+$]; mp 113–116° C.

Example G36

[2-Amino-4-(4-trifluoromethoxy-phenylethynyl)-phenyl]-carbamic acid tert.-butyl ester Prepared from [2-nitro-4-(4-trifluoromethoxy-phenylethynyl)-phenyl]-carbamic acid tert.-butyl ester (Example F12) (1.09 g, 2.58 mmol) by reduction with SnCl$_2$$_2$H$_2$O (2.91 g, 12.9 mmol) according to the general procedure G (method b). Obtained as a light brown solid (690 mg).
MS (ISP) 393 [(M+H)$^+$]; mp 167–169° C.

Example G37

(3-Amino-2'-fluoro-biphenyl-4-yl)-carbamic acid tert.-butyl ester

Prepared from (2'-fluoro-3-nitro-biphenyl-4-yl)-carbamic acid tert.-butyl ester (Example B10) by catalytic hydrogenation with Pd/C according to the general procedure G (method a). Obtained as a yellow solid (1.31 g).
MS (ISP) 303 [(M+H)$^+$]; mp 100–103° C.

Example G38

(3-Amino-3'-fluoro-biphenyl-4-yl)-carbamic acid tert.-butyl ester

Prepared from (3'-fluoro-3-nitro-biphenyl-4-yl)-carbamic acid tert.-butyl ester (Example B1) by catalytic hydrogenation with Pd/C according to the general procedure G (method a). Obtained as a brown solid (3.40 g).
MS (ISP) 303 [(M+H)$^+$]; mp 125–128° C.

Example G39

(3-Amino-4'-fluoro-biphenyl-4-yl)-carbamic acid tert.-butyl ester

Prepared from (4'-fluoro-3-nitro-biphenyl-4-yl)-carbamic acid tert.-butyl ester (Example B12) by catalytic hydrogenation with Raney-Nickel according to the general procedure G (method a). Obtained as a light yellow solid (3.40 g).
MS (ISP) 303 [(M+H)$^+$].

Example G40

(3-Amino-4'-cyano-biphenyl-4-yl)-carbamic acid tert.-butyl ester

Prepared from (4'-cyano-3-nitro-biphenyl-4-yl)-carbamic acid tert.-butyl ester (Example C13) by reduction with SnCl$_2$.2H$_2$O according to the general procedure G (method b). Obtained as a yellow solid (360 mg).
MS (ISP) 310 [(M+H)$^+$]; mp 195° C. (dec.).

Example G41

(3-Amino-3'-fluoro-biphenyl-4-yl)-carbamic acid tert.-butyl ester

Prepared from (4'-fluoro-2'-methyl-3-nitro-biphenyl-4-yl)-carbamic acid tert.-butyl ester (Example B13) by catalytic hydrogenation with Pd/C according to the general procedure G (method a). Obtained as a light yellow solid (1.51 g).
MS (ISP) 317 [(M+H)$^+$]; mp 143° C.

Example G42

(3-Amino-4'-fluoro-2'-methoxymethoxy-biphenyl-4-yl)-carbamic acid tert.-butyl ester Prepared from (4'-fluoro-2'-methoxymethoxy-3-nitro-biphenyl-4-yl)-carbamic acid tert.-butyl ester (Example B14) by catalytic hydrogenation with Pd/C according to the general procedure G (method a). Obtained as a light purple foam (577 mg).
MS (ISP) 363 [(M+H)$^+$].

Example G43

(3-Amino-2',4'-difluoro-biphenyl-4-yl)-carbamic acid tert.-butyl ester

Prepared from (2',4'-difluoro-3-nitro-biphenyl-4-yl)-carbamic acid tert.-butyl ester (Example B15) by catalytic hydrogenation with Pd/C according to the general procedure G (method a). Obtained as a light yellow solid (1.77 g).
MS (ISP) 321 [(M+H)$^+$]; mp 120° C. (dec.).

Example G44

(3-Amino-2'-fluoro-6'-methoxy-biphenyl-4-yl)-carbamic acid tert.-butyl ester

Prepared from (2'-fluoro-6'-methoxy-3-nitro-biphenyl-4-yl)-carbamic acid tert.-butyl ester (Example B16) by catalytic hydrogenation with Pd/C according to the general procedure G (method a). Obtained as a light purple foam (577 mg).
MS (ISP) 333 [(M+H)$^+$]; mp 165–167° C.

Example G45

(3-Amino-2',5'-difluoro-biphenyl-4-yl)-carbamic acid tert.-butyl ester

Prepared from (2',5'-difluoro-3-nitro-biphenyl-4-yl)-carbamic acid tert.-butyl ester (Example B17) by catalytic hydrogenation with Pd/C according to the general procedure G (method a). Obtained as a light yellow gum (2.18 g).
MS (ISN) 319 [(M−H)$^-$].

Example G46

(2-Amino-4-benzofuran-2-yl-phenyl)-carbamic acid tert.-butyl ester

Prepared from (4-benzofuran-2-yl-2-nitro-phenyl)-carbamic acid tert.-butyl ester (Example B18) by reduction with SnCl$_2$.2H$_2$O according to the general procedure G (method b). Obtained as an orange solid (579 mg).
MS (ISN) 323 [(M−H)$^-$]; mp 165° C.

Example G47

(2-Amino-4-isopropyl-phenyl)-carbamic acid tert.-butyl ester

Prepared from (4-isopropyl-2-nitro-phenyl)-carbamic acid tert.-butyl ester (Example A2) by catalytic hydrogenation with Pd/C according to the general procedure G (method a). Obtained as a white solid (12.59 g).
MS (ISP) 251 [(M+H)$^+$]; mp 100–101° C.

Example G48

(2-Amino-4-cyclopropyl-phenyl)-carbamic acid tert.-butyl ester

Prepared from (4-cyclopropyl-2-nitro-phenyl)-carbamic acid tert.-butyl ester (Example A3) by reduction with SnCl$_2$.2H$_2$O according to the general procedure G (method b). Obtained as a dark solid (1.96 g).
MS (ISP) 249 [(M+H)$^+$].

Example G49

(3-Amino-2',3'-difluoro-biphenyl-4-yl)-carbamic acid tert.-butyl ester

Prepared from (2',3'-difluoro-3-nitro-biphenyl-4-yl)-carbamic acid tert.-butyl ester (Example B19) (3.14 g, 8.96 mmol) by catalytic hydrogenation with Pd/C according to the general procedure G (method a). Obtained as a green solid (2.91 g).
MS (ISP) 321 [(M+H)$^+$]; mp 78° C.

General Procedure H (Synthetic Scheme F)

Method a) Preparation of ethyl or tert.-butyl 3-aryl-3-oxo-propionates

The ethyl or tert.-butyl 3-aryl-3-oxo-propionates were prepared from the aryl acid chlorides and ethyl or tert.-butyl malonate potassium salt [CAS-no. 6148-64-7 and 75486-33-8] with Et$_3$N and MgCl$_2$ in CH$_3$CN at 0° C. to 23° C. according to *Synthesis* 1993, 290. If the free aryl carboxylic acid was employed in this reaction, it was activated by treatment with ethyl chloroformate and Et$_3$N in THF/CH$_3$CN at 0° C. prior to reaction with the malonate salt.

Method b) Preparation of tert.-butyl 3-aryl-3-oxo-propionates

The tert.-butyl 3-aryl-3-oxo-propionates were alternatively prepared from the methyl or ethyl aryl esters by treatment with lithium tert.-butyl acetate [prepared by treatment of tert.-butyl acetate with lithium diisopropylamide in THF at −78° C.] in the presence of lithium tert.-butoxide according to *Synthesis* 1985, 45. If the product contained residual starting material after workup, thus could be removed by selective saponification with LiOH in THF/MeOH/H$_2$O at 23° C.

Method c) Preparation of 3-aryl-3-oxo-propionic acids

The 3-aryl-3-oxo-propionic acids were prepared from the aryl acid chlorides and bis(trimethylsilyl)malonate with Et$_3$N and LiBr in CH$_3$CN at 0° C. according to *Synth. Commun.* 1985, 15, 1039 (method c1) or with n-BuLi in ether at −60° C. to 0° C. according to *Synthesis* 1979, 787 (method c2).

Example H1

3-Oxo-3-(3-[1,2,4]triazol-4-yl-phenyl)-propionic acid ethyl ester

Prepared from 3-[1,2,4]triazol-4-yl-benzoic acid [prepared by reaction of 3-aminobenzoic acid with hydrazine hydrate and triethyl orthoformate in acetic acid at 120° C.] by activation with ethyl chloroformate/Et$_3$N and reaction with ethyl malonate potassium salt with Et$_3$N and MgCl$_2$ in CH$_3$CN according to general procedure H (method a). Obtained as a white solid (5.74 g).
MS (EI) 259 (M$^+$).

Example H2

3-Oxo-3-(3-[1,2,3]triazol-1-yl-phenyl)-propionic acid ethyl ester

Prepared from 3-[1,2,3]triazol-1-yl-benzoic acid [prepared by refluxing of methyl 3-azidobenzoate [CAS-No. 93066-93-4] in trimethylsilylacetylene, followed by saponification with aqueous NaOH in refluxing EtOH] by activation with ethyl chloroformate/Et$_3$N and reaction with ethyl malonate potassium salt with Et$_3$N and MgCl$_2$ in CH$_3$CN according to general procedure H (method a). Obtained as a light yellow solid (2.22 g).
MS (EI) 259 (M$^+$); mp 72–74° C.

Example H3

3-(3-Cyano-phenyl)-3-oxo-propionic acid tert-butyl ester

Prepared from methyl 3-cyanobenzoate [CAS-No. 13531-48-1] by treatment with lithium tert.-butyl acetate according to general procedure H (method b). Obtained as a light brown oily semisolid. MS (EI) 245 (M$^+$).

Example H4

3-(3-Imidazol-1-yl-phenyl)-3-oxo-propionic acid tert.-butyl ester

Prepared from methyl 3-(1H-imidazol-1-yl)benzoate [prepared from 3-(1H-imidazol-1-yl)benzoic acid (*J. Med. Chem.* 1987, 30, 1342; CAS-No. [108035-47-8]) by refluxing in conc. H$_2$SO$_4$/MeOH] by treatment with lithium tert.-butyl acetate according to general procedure H (method b). Obtained as an orange-brown oil.
MS (ISP) 287 [(M+H)$^+$].

Example H5

3-(2-Imidazol-1-yl-pyridin-4-yl)-3-oxo-propionic acid tert.-butyl ester

Prepared from 2-imidazol-1-yl-isonicotinoyl chloride hydrochloride [prepared by reaction of tert.-butyl 2-chloroisonicotinoate with imidazole and NaH in DMF at 80° C., treatment with formic acid at 50° C. and reaction with thionylchloride in toluene at 100° C.] and tert.-butyl malonate potassium salt with Et$_3$N and MgCl$_2$ in CH$_3$CN according to general procedure H (method a). Obtained as a brown solid (10.8 g).
MS (EI) 287 (M$^+$); mp 80° C. (dec.).

Example H6

3-Oxo-3-(3-[1,2,4]triazol-1-yl-phenyl)-propionic acid tert.-butyl ester

Prepared from methyl 3-[1,2,4]triazol-1-yl-benzoate [CAS-No. 167626-27-9] by treatment with lithium tert.-butyl acetate according to general procedure H (method b). Obtained as an orange liquid (2.41 g).
MS (EI) 287 (M$^+$).

Example H7

3-[3-(4-Methyl-imidazol-1-yl)-phenyl]-3-oxo-propionic acid tert.-butyl ester.

Prepared from methyl 3-(4-methyl-imidazol-1-yl)-benzoate [prepared the corresponding acid from 3-isothiocyanatobenzoic acid and 2-aminopropionaldehyde dimethyl acetal according to *J. Med. Chem.* 1987, 30, 1342, followed by refluxing in conc. H$_2$SO$_4$/MeOH] by treatment with lithium tert.-butyl acetate according to general procedure H (method b). Obtained as a yellow-brown oil (10.69 g).
MS (EI) 300 (M$^+$).

Example H8

3-[3-(2-Methyl-imidazol-1-yl)-phenyl]-3-oxo-propionic acid tert.-butyl ester

Prepared from ethyl 3-(2-methyl-imidazol-1-yl)-benzoate [prepared by reaction of ethyl 3-aminobenzoate with ethyl acetimidate hydrochloride in EtOH at 0° C., direct treatment with aminoacetaldehyde diethyl acetal in EtOH at 23° C., follwed by addition of conc. H$_2$SO$_4$ and refluxing.] by treatment with lithium tert.-butyl acetate according to general procedure H (method b). Obtained as a brown oil (9.66 g).
MS (ISN) 299 [(M−H)$^-$].

Example H9

3-[3-(2,4-Dimethyl-imidazol-1-yl)-phenyl]-3-oxo-propionic acid tert.-butyl ester Prepared from ethyl 3-(2,4-dimethyl-imidazol-1-yl)-benzoate [prepared by reaction of ethyl 3-aminobenzoate with ethyl acetimidate hydrochloride in EtOH at 0° C., direct treatment with 2-aminopropionaldehyde dimethyl acetal in EtOH at 23° C., follwed by addition of conc. H$_2$SO$_4$ and refluxing.] by treatment with lithium tert.-butyl acetate according to general procedure H (method b). Obtained as a yellow-brown oil (6.00 g).
MS (ISN) 313 [(M–H)$^-$].

Example H10

3-(2-Cyano-pyridin-4-yl)-3-oxo-propionic acid tert.-butyl ester

Prepared from 2-cyano-isonicotinic acid ethyl ester [CAS-No. 58481-14-4] by treatment with lithium tert.-butyl acetate according to general procedure H (method b). Obtained as a light brown solid (7.70 g).
MS (ISN) 245 [(M–H)$^-$].

Example H11

3-Oxo-3-(3-[1,2,4]triazol-4-yl-phenyl)-propionic acid tert.-butyl ester

Prepared from methyl 3-[1,2,4]triazol-4-yl-benzoate [prepared by reaction of 3-aminobenzoic acid with hydrazine hydrate and triethyl orthoformate in acetic acid at 120° C., followed by esterification with conc. H$_2$SO$_4$ in refluxing MeOH] by treatment with lithium tert.-butyl acetate according to general procedure H (method b). Obtained as a light yellow gum (870 mg).
MS (ISN) 286 [(M–H)$^-$].

Example H12

3-[3-(2-Methoxymethylsulfanyl-imidazol-1-yl)-phenyl]-3-oxo-propionic acid tert.-butyl ester Prepared from ethyl 3-(2-methoxymethylsulfanyl-imidazol-1-yl)-benzoate [prepared by esterification of 3-(2-methoxymethylsulfanyl-imidazol-1-yl)-benzoic acid [CAS-No. 108035-46-7] with conc. H$_2$SO$_4$ in EtOH, followed by treatment with chloromethylmethyl ether and NaH in THF/DMF] by treatment with lithium tert.-butyl acetate according to general procedure H (method b). Obtained as an orange oil (1.82 g).
MS (EI) 362 (M$^+$).

Example H13

3-[3-(2-Methylsulfanyl-imidazol-1-yl)-phenyl]-3-oxo-propionic acid tert.-butyl ester Prepared from ethyl 3-(2-methylsulfanyl-imidazol-1-yl)-benzoate [prepared by esterification of 3-(2-methoxymethylsulfanyl-imidazol-1-yl)-benzoic acid [CAS-No. 108035-46-7] with conc. H$_2$SO$_4$ in EtOH, followed by treatment methyl iodide and NaH in THF/DMF] by treatment with lithium tert.-butyl acetate according to general procedure H (method b). Obtained as a light brown oil (4.41 g).
MS (ISP) 333 [(M+H)$^+$].

Example H14

3-[3-(3-Methyl-isoxazol-5-yl)-phenyl]-3-oxo-propionic acid tert.-butyl ester

Prepared from ethyl 3-(3-methyl-isoxazol-5-yl)-benzoate [prepared by reaction of ethyl 3-ethynylbenzoate [CAS-No. 178742-95-5] with a mixture of NCS, acetaldoxime, Et$_3$N and cat. amount of pyridine in CHCl$_3$ at 50° C. according to *Tetrahedron* 1984, 40, 2985–2988] by treatment with lithium tert.-butyl acetate according to general procedure H (method b). Obtained as a yellow solid (2.54 g).
MS (ISP) 302 [(M+H)$^+$]; mp 50–56° C.

Example H15

3-Oxo-3-(3-tetrazol-1-yl-phenyl)-propionic acid ethyl ester

Prepared from 3-tetrazol-1-yl-benzoic acid [CAS-No. 204196-80-5] by activation with ethyl chloroformate/Et$_3$N and reaction with ethyl malonate potassium salt with Et$_3$N and MgCl$_2$ in CH$_3$CN according to general procedure H (method a). Obtained as a light yellow solid (211 mg).
MS (EI) 260 (M$^+$).

Example H16

3-(3-Chloro-thiophen-2-yl)-3-oxo-propionic acid ethyl ester

Prepared from 3-chloro-2-thiophenecarbonyl chloride [CAS-No. 86427-02-3] by reaction with ethyl malonate potassium salt with Et$_3$N and MgCl$_2$ in CH$_3$CN according to general procedure H (method a). Obtained as a brown oil (6.84 g).
MS (EI) 232 (M$^+$) and 234 [(M+2)$^+$].

Example H17

3-(5-Cyano-thiophen-2-yl)-3-oxo-propionic acid tert.-butyl ester

Prepared from ethyl 5-cyano-2-thiophenecarboxylate [CAS-No. 67808-35-9] by treatment with lithium tert.-butyl acetate according to general procedure H (method b). Obtained as a yellow solid (6.66 g).
MS (EI) 251 (M$^+$); mp 78° C.

Example H18

3-(5-Cyano-2-fluoro-phenyl)-3-oxo-propionic acid ethyl ester

Prepared from 5-cyano-2-fluoro-benzoyl chloride [prepared from the corresponding acid [CAS-No. 146328-87-2] by treatment with SOCl$_2$, cat. DMF in toluene at 80° C.] by reaction with ethyl malonate potassium salt with Et$_3$N and MgCl$_2$ in CH$_3$CN according to general procedure H (method a). Obtained as a light yellow solid (3.85 g).
MS (EI) 235 (M$^+$); mp 55–60° C.

Example H19

3-(2-Imidazol-1-yl-thiazol-4-yl)-3-oxo-propionic acid tert.-butyl ester

Prepared from ethyl 2-imidazol-1-yl-thiazole-4-carboxylate [CAS-No. 256420-32-3] by treatment with lithium tert.-butyl acetate according to general procedure H (method b). Obtained as an orange oil (12.0 g).

Example H20

3-[2-(4-Methyl-imidazol-1-yl)-thiazol-4-yl]-3-oxo-propionic acid tert.-butyl ester Prepared from ethyl 2-(4-methyl-imidazol-1-yl)-thiazole-4-carboxylate [prepared from ethyl 2-amino-4-thiazolecarboxylate (CAS-No. [256420-32-3]) by the following synthetic sequence: 1.) NaH, 2-isothiocyanato-1,1-dimethoxypropane, DMF, 23° C.; 2.) aq. $H_2SO_4$, reflux; 3.) EtOH, conc. $H_2SO_4$, 23° C.; 4.) 30% $H_2O_2$, HOAc, 23° C.] by treatment with lithium tert.-butyl acetate according to general procedure H (method b). Obtained as a brown oil (8.73 g).

MS (EI) 307 ($M^+$).

Example H21

3-[3-(1-Methyl-1H-imidazol-2-yl)-phenyl]-3-oxo-propionic acid tert.-butyl ester

Prepared from ethyl 3-(1-methyl-1H-imidazol-2-yl)benzoate [CAS-No. 168422-44-4] by treatment with lithium tert.-butyl acetate according to general procedure H (method b). Obtained as a light yellow liquid (1.26 g).

MS (ISP) 301.3 [$(M+H)^+$].

General Procedure J (Synthetic Scheme F)

Preparation of 6-aryl-2,2-dimethyl-[1,3]dioxin-4-ones

Method a)

The 6-aryl-2,2-dimethyl-[1,3]dioxin-4-ones were prepared from 3-aryl-3-oxo-propionic acids and catalytic amount of conc. $H_2SO_4$ or trifluoroacetic acid (TFA) in isopropenyl acetate at 23° C. according to *Chem. Pharm. Bull.* 1983, 31, 1896. The final products were purified by silica gel column chromatography with hexane/EtOAc.

Method b)

The 6-aryl-2,2-dimethyl-[1,3]dioxin-4-ones were prepared from the tert.-butyl 3-aryl-3-oxo-propionates by treatment with trifluoroacetic anhydride (TFAA) in a mixture of TFA and acetone at 23° C. according to *Tetrahedron Lett.* 1998, 39, 2253. The final products were if necessary purified by silica gel column chromatography with hexane/EtOAc.

Example J1

2,2-Dimethyl-6-thiophen-2-yl-[1,3]dioxin-4-one

The 3-oxo-3-thiophen-2-yl-propionic acid was prepared from thiophene-2-carbonyl chloride (5.3 mL, 50 mmol) and bis(trimethylsilyl)malonate (25.6 mL, 100 mmol) with n-BuLi (1.6M in hexane, 62.5 mL) in ether at −60° C. to 0° C. according to the general procedure H (method c2). The crude material (7.88 g) was transformed into the title compound by stirring in isopropenyl acetate and TFA according to the general procedure J (method a). Obtained as a yellow solid (4.09 g).

MS (EI) 210 ($M^+$); mp 42° C. (dec.).

Example J2

6-(3-Chloro-thiophen-2-yl)-2,2-dimethyl-[1,3]dioxin-4-one

The 3-(3-chloro-thiophen-2-yl)-3-oxo-propionic acid was prepared from 3-chloro-thiophene-2-carbonyl chloride (7.82 g, 43.2 mmol) and bis(trimethylsilyl)malonate (11.6 mL, 45.4 mmol) with $Et_3N$ (12.65 mL, 90.7 mmol) and LiBr (3.53 g, 47.5 mmol) in $CH_3CN$ at 0° C. according to general procedure H (method c1). The crude material (5.69 g) was transformed into the title compound by stirring in isopropenyl acetate and conc. $H_2SO_4$ according to general procedure J (method a). Obtained as an orange solid (2.3 g).

MS (EI) 244 ($M^+$) and 246 [$(M+2)^+$]; mp 88–89° C. (dec.).

Example J3

6-(3-Cyano-thiophen-2-yl)-2,2-dimethyl-[1,3]dioxin-4-one

The 3-(3-cyano-thiophen-2-yl)-3-oxo-propionic acid was prepared from 3-cyano-thiophene-2-carbonyl chloride (24.33 g, 140.6 mmol) and bis(trimethylsilyl)malonate (38.0 mL, 147.7 mmol) with $Et_3N$ (41 mL, 295.4 mmol) and LiBr (13.5 g, 154.7 mmol) in $CH_3CN$ at 0° C. according to general procedure H (method c1). The crude material (24.8 g) was transformed into the title compound by stirring in isopropenyl acetate and conc. $H_2SO_4$ according to general procedure J (method a). Obtained as an orange solid (5.6 g).

MS (EI) 235 ($M^+$); mp 116–120° C. (dec.).

Example J4

3-(2,2-Dimethyl-6-oxo-6H-[1,3]dioxin-4-yl)-benzonitrile

The 3-(3-cyano-phenyl)-3-oxo-propionic acid was prepared from 3-cyanobenzoyl chloride (828 mg, 5 mmol) and bis(trimethylsilyl)malonate (2.56 mL, 10 mmol) with n-BuLi (1.6M in hexane, 6.25 mL) in ether at −60° C. to 0° C. according to general procedure H (method c2). The crude material (1.04 g) was transformed into the title compound by stirring in isopropenyl acetate and TFA according to general procedure J (method a). Obtained as a light yellow solid (0.8 g).

MS (EI) 229 ($M^+$); mp 138° C. (dec.).

Example J5

2,2-Dimethyl-6-(3-trifluoromethyl-phenyl)-[1,3]dioxin-4-one

The 3-oxo-3-(3-trifluoromethyl-phenyl)-propionic acid was prepared from 3-trifluoromethylbenzoyl chloride (10 mL, 67.6 mmol) and bis(trimethylsilyl)malonate (18.2 mL, 71 mmol) with $Et_3N$ (20 mL, 142 mmol) and LiBr (6.46 g, 74.4 mmol) in $CH_3CN$ at 0° C. according to general procedure H (method c1). The crude material (7.0 g of the obtained 15.4 g) was transformed into the title compound by stirring in isopropenyl acetate and conc. $H_2SO_4$ according to general procedure J (method a). Obtained as a light yellow solid (5.3 g).

MS (EI) 272 ($M^+$); mp 77–78° C. (dec.).

Example J6

6-(3-Chloro-phenyl)-2,2-dimethyl-[1,3]dioxin-4-one

The 3-(3-chloro-phenyl)-3-oxo-propionic acid was prepared from 3-chlorobenzoyl chloride (11 mL, 85.7 mmol) and bis(trimethylsilyl)malonate (23.0 mL, 90.0 mmol) with $Et_3N$ (25 mL, 180 mmol) and LiBr (8.19 g, 94.3 mmol) in

Example J7

6-(3-Iodo-phenyl)-2,2-dimethyl-[1,3]dioxin-4-one

The 3-(3-iodo-phenyl)-3-oxo-propionic acid was prepared from 3-iodobenzoyl chloride (21.0 g, 78.8 mmol) and bis(trimethylsilyl)malonate (21.0 mL, 82.8 mmol) with $Et_3N$ (23 mL, 165.5 mmol) and LiBr (7.54 g, 86.7 mmol) in $CH_3CN$ at 0° C. according to general procedure H (method c1). The crude material (21.9 g) was transformed into the title compound by stirring in isopropenyl acetate and conc. $H_2SO_4$ according to general procedure J (method a). Obtained as a yellow solid (9.6 g).

MS (EI) 330 (M$^+$); mp 79–80° C. (dec.).

Example J8

2,2-Dimethyl-6-(3-trifluoromethoxy-phenyl)-[1,3]dioxin-4-one

The 3-oxo-3-(3-trifluoromethoxy-phenyl)-propionic acid was prepared from 3-trifluoromethoxybenzoyl chloride and bis(trimethylsilyl) malonate with $Et_3N$ and LiBr in $CH_3CN$ at 0° C. according to general procedure H (method c1). The crude material was transformed into the title compound by stirring in isopropenyl acetate and conc. $H_2SO_4$ according to general procedure J (method a). Obtained as an orange solid (2.27 g).

MS (EI) 288 (M$^+$); mp 49–54° C. (dec.).

Example J9

2,2-Dimethyl-6-pyridin-4-yl-[1,3]dioxin-4-one

Prepared from 3-oxo-3-pyridin-4-yl-propionic acid [prepared from 4-acetylpyridine, magnesium methylcarbonate and $CO_2$ in DMF at 120° C. according to *Journal of Antibiotics* 1978, 31, 1245] by treatment with acetone, TFA and TFAA according to general procedure J (method b). Obtained as a white solid (1.3 g).

MS (EI) 205 (M$^+$)

Example J10

6-(3-Imidazol-1-yl-phenyl)-2,2-dimethyl-[1,3]dioxin-4-one

The 3-(3-imidazol-1-yl-phenyl)-3-oxo-propionic acid was prepared from 3-(1H-imidazol-1-yl)benzoyl chloride hydrochloride [prepared by treatment of 3-(1H-imidazol-1-yl)benzoic acid (*J. Med. Chem.* 1987, 30, 1342; CAS-No. [108035-47-8] with $SOCl_2$) and bis(trimethylsilyl)malonate with $Et_3N$ and LiBr in $CH_3CN$ at 0° C. according to general procedure H (method c1). The crude material was transformed into the title compound by stirring in isopropenyl acetate and conc. $H_2SO_4$ according to general procedure J (method a). Obtained as an orange semisolid (617 g).

MS (EI) 270 (M$^+$).

Example J11

2,2-Dimethyl-6-(3-methoxy-phenyl)-[1,3]dioxin-4-one

The 3-(3-methoxy-phenyl)-3-oxo-propionic acid was prepared from 3-methoxybenzoyl chloride (10.3 g, 60.4 mmol) and bis(trimethylsilyl)malonate (16.2 mL, 63.4 mmol) with $Et_3N$ (17.7 mL, 127 mmol) and LiBr (5.77 g, 66.4 mmol) in $CH_3CN$ at 0° C. according to general procedure H (method c1). The crude material (6.38 g) was transformed into the title compound by stirring in isopropenyl acetate and conc. $H_2SO_4$ according to general procedure J (method a). Obtained as a yellow oil (640 mg).

MS (ISP) 235 [(M+H)$^+$] and 252 [(M+NH$_4$)$^+$].

Example J12

2,2-Dimethyl-6-(3-nitro-phenyl)-[1,3]dioxin-4-one

The 3-(3-nitro-phenyl)-3-oxo-propionic acid tert.-butyl ester was prepared from 3-nitrobenzoyl chloride (2.71 g, 14.6 mmol) and tert.-butyl malonate potassium salt (6.0 g, 30.0 mmol) with $Et_3N$ (4.5 mL, 32.2 mmol) and $MgCl_2$ (3.48 g, 36.52 mmol) in $CH_3CN$ according to general procedure H (method a). The crude material (3.88 g) was transformed into the title compound by stirring in TFA/acetone with TFAA according to general procedure J (method b). Obtained as a yellow solid (2.76 g).

MS (EI) 249 (M$^+$); mp 110–117° C.

Example J13

2,2-Dimethyl-6-(3-[1,2,4]triazol-1-yl-phenyl)-[1,3]dioxin-4-one

The 3-oxo-3-(3-[1,2,4]triazol-1-yl-phenyl)-propionic acid tert.-butyl ester was prepared from 3-[1,2,4]triazol-1-yl-benzoic acid methyl ester [CAS-No. 167626-27-9] by treatment with lithium tert.-butyl acetate according to general procedure H (method b). Prepared from (Example H6) by stirring in TFA/acetone with TFAA according to general procedure J (method b). Obtained as a yellow solid (539 mg).

MS (EI) 271 (M$^+$).

Example J4

6-(2-Imidazol-1-yl-pyridin-4-yl)-2,2-dimethyl-[1,3]dioxin-4-one

Prepared from 3-(2-imidazol-1-yl-pyridin-4-yl)-3-oxo-propionic acid tert.-butyl ester (Example H5) by stirring in TFA/acetone with TFAA according to general procedure J (method b). Obtained as a brown solid (10.8 g).

MS (EI) 271 (M$^+$); mp 151° C. (dec.).

Example J15

2,2-Dimethyl-6-[3-(2-methyl-imidazol-1-yl)-phenyl]-[1,3]dioxin-4-one

Prepared from 3-[3-(2-methyl-imidazol-1-yl)-phenyl]-3-oxo-propionic acid tert.-butyl ester (Example H8) by stirring in TFA/acetone with TFAA according to general procedure J (method b). Obtained as a beige solid (2.13 g).

MS (EI) 284 (M$^+$); mp 122° C.

Example J16

4-(2,2-Dimethyl-6-oxo-6H-[1,3]dioxin-4-yl)-pyridine-2-carbonitrile

Prepared from 3-(2-cyano-pyridin-4-yl)-3-oxo-propionic acid tert.-butyl ester (Example H10) by stirring in TFA/acetone with TFAA according to general procedure J (method b). Obtained as a brown solid (3.30 g).

MS (EI) 230 (M$^+$); mp 132° C. (dec.).

General Procedure K (Synthetic Scheme B)

Preparation of {2-[3-aryl-3-oxo-propionylamino]-4-aryl-phenyl}-carbamic acid tert.-butyl ester by reaction of (2-amino-4-aryl-phenyl)-carbamic acid tert.-butyl esters with ethyl or tert.-butyl 3-aryl-3-oxo-propionates or 6-aryl-2,2-dimethyl-[1,3]dioxin-4-ones; also 3-aryl-N-(2-nitro-4-aryl-phenyl)-3-oxo-propionamides by reaction of 2-nitro-4-aryl-phenylamines with 6-aryl-2,2-dimethyl-[1,3]dioxin-4-ones.

A mixture of the (2-amino-4-aryl-phenyl)-carbamic acid tert.-butyl ester or 2-nitro-4-aryl-phenylamine (1.0 mmol) and the ethyl or tert.-butyl 3-aryl-3-oxo-propionate or 6-aryl-2,2-dimethyl-[1,3]dioxin-4-one (0.8–1.5 mmol) was refluxed in toluene (4–8 mL) until thin layer chromatography indicated complete consumption of the minor component. The solution was allowed to cool to 23° C., whereupon the product generally crystallized (in cases where crystallization failed to appear it was induced by addition of hexane or the entire reaction mixture was directly subjected to chromatography). The solid was filtered off, washed with ether or mixtures of ether/hexane and dried in vacuum to give the {2-[3-aryl-3-oxo-propionylamino]-4-aryl-phenyl}-carbamic acid tert.-butyl esters or 3-aryl-N-(2-nitro-4-aryl-phenyl)-3-oxo-propionamides, which was used directly in the following step or—if necessary—was purified by recrystallization or by silica gel column chromatography.

Example K1

{2-[3-(3-Cyano-phenyl)-3-oxo-propionylamino]-4-iodo-phenyl}-carbamic acid tert.-butyl ester

Prepared from (2-amino-4-iodo-phenyl)-carbamic acid tert.-butyl ester (Example G1) (900 mg, 2.7 mmol) and 3-(3-cyano-phenyl)-3-oxo-propionic acid ethyl ester (880 mg, 4.1 mmol) according to the general procedure K. Obtained as a yellow solid (1.2 g).

MS (ISP) 506 [(M+H)$^+$] and 528 [(M+Na)$^+$]; mp 182–183° C.

Example K2

{2-[3-(3-Cyano-phenyl)-3-oxo-propionylamino]-4-phenylethynyl-phenyl}-carbamic acid tert.-butyl ester

Prepared from (2-amino-4-phenylethynyl-phenyl)-carbamic acid tert.-butyl ester (Example G2) (214 mg, 0.7 mmol) and 3-(2,2-dimethyl-6-oxo-6H-[1,3]dioxin-4-yl)-benzonitrile (Example J4) (250 mg, 1.1 mmol) according to the general procedure K. Obtained as a light yellow solid (260 mg).

MS (ISP) 480 [(M+H)$^+$], 497 [(M+NH$_4$)$^+$] and 502 [(M+Na)$^+$]; mp 168–170° C. (dec.).

Example K3

{3-[3-(3-Cyano-phenyl)-3-oxo-propionylamino]-4'-methoxy-biphenyl-4-yl}-carbamic acid tert.-butyl ester

Prepared from (3-amino-4'-methoxy-biphenyl-4-yl)-carbamic acid tert.-butyl ester (Example G5) and 3-(2,2-dimethyl-6-oxo-6H-[1,3]dioxin-4-yl)-benzonitrile (Example J4) according to the general procedure K. Obtained as a light brown solid (207 mg).

MS (ISP) 486 [(M+H)$^+$], 508 [(M+Na)$^+$] and 524 [(M+K)$^+$]

Example K4

{2-[3-(3-Cyano-phenyl)-3-oxo-propionylamino]-4-thiophen-3-yl-phenyl}-carbamic acid tert.-butyl ester

Prepared from (2-amino-4-thiophen-3-yl-phenyl)-carbamic acid tert.-butyl ester (Example G6) and 3-(2,2-dimethyl-6-oxo-6H-[1,3]dioxin-4-yl)-benzonitrile (Example J4) according to the general procedure K. Obtained as a brown solid (104 mg) and used crude in the next step (Example 7).

Example K5

{2-[3-(3-Cyano-phenyl)-3-oxo-propionylamino]-4-furan-2-yl-phenyl}-carbamic acid tert.-butyl ester

Prepared from (2-amino-4-furan-2-yl-phenyl)-carbamic acid tert.-butyl ester (Example G7) and 3-(2,2-dimethyl-6-oxo-6H-[1,3]dioxin-4-yl)-benzonitrile (Example J4) according to the general procedure K. Obtained as a beige powder (271 mg).

MS (ISP) 446 [(M+H)$^+$], 468 [(M+Na)$^+$] and 484 [(M+K)$^+$]

Example K6

{3-[3-(3-Cyano-phenyl)-3-oxo-propionylamino]-biphenyl-4-yl}-carbamic acid tert.-butyl ester

Prepared from (3-amino-biphenyl-4-yl)-carbamic acid tert.-butyl ester (Example G9) (250 mg, 0.88 mmol) and 3-(2,2-dimethyl-6-oxo-6H-[1,3]dioxin-4-yl)-benzonitrile (Example J4) (243 mg, 1.06 mmol) according to the general procedure K. Obtained as a white solid (324 mg).

MS (ISP) 456 [(M+H)$^+$]; mp 168° C. (dec.)

Example K7

{2-[3-(3-Iodo-phenyl)-3-oxo-propionylamino]-4-phenylethynyl-phenyl}-carbamic acid tert.-butyl ester

Prepared from (2-amino-4-phenylethynyl-phenyl)-carbamic acid tert.-butyl ester (Example G2) (1.0 g, 3.24 mmol) and 6-(3-iodo-phenyl)-2,2-dimethyl-[1,3]dioxin-4-one (Example J7) (1.78 g, 3.57 mmol) according to the general procedure K. Obtained as a light yellow solid (1.9 g).

MS (ISP) 581 [(M+H)$^+$] and 603 [(M+Na)$^+$]; mp 193–195° C. (dec.)

Example K8

{3-[3-(3-Azido-phenyl)-3-oxo-propionylamino]-biphenyl-4-yl}-carbamic acid tert.-butyl ester Prepared (3-amino-biphenyl-4-yl)-carbamic acid tert.-butyl ester (Example G9) (569 mg, 2 mmol) and 3-(3-azido-phenyl)-3-oxo-propionic acid ethyl ester (700 mg, 3 mmol; prepared from 3-azido-benzoyl chloride (*Bioorg. Chem* 1986, 134) using the procedure described in *Synthesis*, 1993, 290, method A; MS (EI) 233 (M$^+$)) according to the general procedure K. Obtained as an orange solid (367 mg).

MS (ISP) 472 [(M+H)$^+$] and 494 [(M+Na)$^+$]

Example K8

{3-[3-(3-Cyano-phenyl)-3-oxo-propionylamino]-2',3'-difluoro-biphenyl-4-yl}-carbamic acid tert.-butyl ester Prepared from (3-amino-2',3'-difluoro-biphenyl-4-yl)-carbamic acid tert.-butyl ester (Example G49) (160 mg, 0.5 mmol) and 3-(2,2-dimethyl-6-oxo-6H-[1,3]dioxin-4-yl)-benzonitrile (Example J4) (115 mg, 0.5 mmol) according to the general procedure K. Obtained as a white solid (53 mg).

MS (ISP) 492 [(M+H)$^+$]; mp 118° C.

Example K9

{2-[3-(3-Cyano-phenyl)-3-oxo-propionylamino]-4-furan-3-yl-phenyl}-carbamic acid tert.-butyl ester Prepared from (2-amino-4-furan-3-yl-phenyl)-carbamic acid tert.-butyl ester (Example G11) and 3-(3-cyano-phenyl)-3-oxo-propionic acid ethyl ester (*Pol. J. Chem.* 1978, 25) according to the general procedure K. Obtained as an orange solid (460 mg).

MS (ISP) 446 [(M+H)$^+$], 463 [(M+NH$_4$)$^+$] and 468 [(M+Na)$^+$]

Example K10

{2-[3-(3-Cyano-phenyl)-3-oxo-propionylamino]-4-naphthalen-1-yl-phenyl}-carbamic acid tert.-butyl ester Prepared from (2-amino-4-naphthalen-1-yl-phenyl)-carbamic acid tert.-butyl ester (Example G14) and 3-(2,2-dimethyl-6-oxo-6H-[1,3]dioxin-4-yl)-benzonitrile (Example J4) according to the general procedure K. Obtained as an off-white solid (92 mg) and used crude in the next step (Example 20).

Example K11

{2-[3-(3-Cyano-phenyl)-3-oxo-propionylamino]-4-thiazol-2-ylethynyl-phenyl}-carbamic acid tert.-butyl ester Prepared from (2-amino-4-thiazol-2-ylethynyl-phenyl)-carbamic acid tert.-butyl ester (Example G11) (89 mg, 0.28 mmol) and 3-(3-cyano-phenyl)-3-oxo-propionic acid ethyl ester (*Pol. J. Chem.* 1978, 25) (74 mg, 0.34 mmol) according to the general procedure K. Obtained as a light yellow solid (129 mg).

MS (ISP) 487 [(M+H)$^+$]; mp 131° C.

Example K12

{2-[3-(3-Chloro-thiophen-2-yl)-3-oxo-propionylamino]-4-pyridin-2-yl-phenyl}-carbamic acid tert.-butyl ester Prepared from (2-amino-4-pyridin-2-yl-phenyl)-carbamic acid tert.-butyl ester (Example G17) and 6-(3-chloro-thiophen-2-yl)-2,2-dimethyl-[1,3]dioxin-4-one (Example J2) according to the general procedure K. Obtained as an amorphous brown solid (145 mg).

MS (ISP) 472 [(M+H)$^+$] and 494 [(M+Na)$^+$]

Example K13

{2-[3-(3-Cyano-phenyl)-3-oxo-propionylamino]-4-pyridin-2-yl-phenyl}-carbamic acid tert.-butyl ester Prepared from (2-amino-4-pyridin-2-yl-phenyl)-carbamic acid tert.-butyl ester (Example G17) and 3-(2,2-dimethyl-6-oxo-6H-[1,3]dioxin-4-yl)-benzonitrile (Example J4) according to the general procedure K. Obtained as a light brown solid (90 mg).

MS (ISP) 457 [(M+H)$^+$] and 479 [(M+Na)$^+$].

Example K14

[3-(3-Oxo-3-thiophen-3-yl-propionylamino)-biphenyl-4-yl]-carbamic acid tert.-butyl ester Prepared from (3-amino-biphenyl-4-yl)-carbamic acid tert.-butyl ester (Example G9) (144 mg, 0.51 mmol) and 3-oxo-3-thiophen-3-yl-propionic acid ethyl ester (FR 7191887) (151 mg, 0.76 mmol) according to the general procedure K. Obtained as a yellow foam (181 mg).

MS (ISN) 435 [(M+H)$^+$].

Example K15

{3-[3-(3-Cyano-phenyl)-3-oxo-propionylamino]-3'-methyl-biphenyl-4-yl}-carbamic acid tert.-butyl ester Prepared from (3-amino-3'-methyl-biphenyl-4-yl)-carbamic acid tert.-butyl ester (Example G20) and 3-(2,2-dimethyl-6-oxo-6H-[1,3]dioxin-4-yl)-benzonitrile (Example J4) according to the general procedure K. Obtained as a viscous orange oil (290 mg).

MS (ISP) 470 [(M+H)$^+$], 492 [(M+Na)$^+$] and 508 [(M+K)$^+$].

Example K16

{3-[3-(3-Chloro-thiophen-2-yl)-3-oxo-propionylamino]-2'-methyl-biphenyl-4-yl}-carbamic acid tert.-butyl ester Prepared from (3-amino-2'-methyl-biphenyl-4-yl)-carbamic acid tert.-butyl ester (Example G23) and 6-(3-chloro-thiophen-2-yl)-2,2-dimethyl-[1,3]dioxin-4-one (Example J2) according to the general procedure K. Obtained as a viscous brown oil (154 mg).

MS (ISP) 485 [(M+H)$^+$], 507 [(M+Na)$^+$] and 523 [(M+K)$^+$].

Example K17

{4-Benzoyl-2-[3-(3-chloro-phenyl)-3-oxo-propionylamino]-phenyl}-carbamic acid tert.-butyl ester Prepared from (2-amino-4-benzoyl-phenyl)-carbamic acid tert.-butyl ester (Example G24) (205 mg, 0.66 mmol) and 6-(3-chloro-phenyl)-2,2-dimethyl-[1,3]dioxin-4-one (Example J6) (174 mg, 0.73 mmol) according to the general procedure K. Obtained as a brown foam (232 mg).

MS (ISP) 493 [(M+H)$^+$].

Example K18

{4-Benzoyl-2-[3-(3-cyano-phenyl)-3-oxo-propionylamino]-phenyl}-carbamic acid tert.-butyl ester Prepared from (2-amino-4-benzoyl-phenyl)-carbamic acid tert.-butyl ester (Example G24) (375 mg, 1.20 mmol) and 3-(3-cyano-phenyl)-3-oxo-propionic acid ethyl ester (*Pol. J. Chem.* 1978, 25) (313 mg, 1.44 mmol) according to the general procedure K. Obtained as a light yellow solid (170 mg).

MS (ISP) 484 [(M+H)$^+$], 501 [(M+NH4)$^+$] and 506 [(M+Na)$^+$]; mp 168° C. (dec.)

Example K19

[4-Benzoyl-2-(3-oxo-3-thiophen-2-yl-propionylamino)-phenyl]-carbamic acid tert.-butyl ester Prepared from (2-amino-4-benzoyl-phenyl)-carbamic acid tert.-butyl ester (Example G24) (259 mg, 0.5 mmol) and 2,2-dimethyl-6-thiophen-2-yl-[1,3]dioxin-4-one (Example J1) (135 mg, 0.55 mmol) according to the general procedure K. Obtained as a light yellow solid (60 mg).

MS (ISP) 465 [(M+H)$^+$]

Example K20

{3-[3-(3-Chloro-thiophen-2-yl)-3-oxo-propionylamino]-biphenyl-4-yl}-carbamic acid tert.-butyl ester Prepared from (3-amino-biphenyl-4-yl)-carbamic acid tert.-butyl ester (Example G9) (100 mg, 0.35 mmol) and 6-(3-chloro-thiophen-2-yl)-2,2-dimethyl-[1,3]dioxin-4-one (Example J2) (95 mg, 0.39 mmol) according to the general procedure K. Obtained as a white solid (127 mg).

MS (ISP) 471 [(M+H)$^+$]; mp 165° C.

Example K21

{3-[3-(3-Cyano-phenyl)-3-oxo-propionylamino]-3'-methoxy-biphenyl-4-yl}-carbamic acid tert.-butyl ester Prepared from (3-amino-3'-methoxy-biphenyl-4-yl)-carbamic acid tert.-butyl ester (Example G25) and 3-(2,2-dimethyl-6-oxo-6H-[1,3]dioxin-4-yl)-benzonitrile (Example J4) according to the general procedure K. Obtained as a beige solid (238 mg).

MS (ISP) 486 [(M+H)$^+$], 508 [(M+Na)$^+$] and 524 [(M+K)$^+$].

Example K22

[5-(6-Oxo-1,6-dihydro-pyridin-3-yl)-2-(3-oxo-3-thiophen-2-yl-propionylamino)-phenyl]-carbamic acid tert.-butyl ester Prepared from [2-amino-4-(6-oxo-1,6-dihydro-pyridin-3-yl)-phenyl]-carbamic acid tert.-butyl ester (Example G31) (200 mg, 0.664 mmol) and 2,2-dimethyl-6-thiophen-2-yl-[1,3]dioxin-4-one (Example J1) (140 mg, 0.665 mmol) according to the general procedure K. Obtained as a beige solid (235 mg).

MS (ISP) 454 [(M+H)$^+$]

Example K23

{4-(6-Benzyloxy-pyridin-3-yl)-2-[3-oxo-3-(3-trifluoromethyl-phenyl)-propionylamino]-phenyl}-carbamic acid tert.-butyl ester Prepared from [2-amino-4-(6-benzyloxy-pyridin-3-yl)-phenyl]-carbamic acid tert.-butyl ester (Example G30) (203 mg, 0.52 mmol) and 2,2-dimethyl-6-(3-trifluoromethyl-phenyl)-[1,3]dioxin-4-one (Example J5) (150 mg, 0.55 mmol) according to the general procedure K. Obtained as an off-white solid (213 mg).

MS (ISP) 606 [(M+H)$^+$]; mp 190° C. (dec.).

Example K24

{3-[3-(3-Cyano-phenyl)-3-oxo-propionylamino]-4'-trifluoromethoxy-biphenyl-4-yl}-carbamic acid tert.-butyl ester Prepared from (3-amino-4'-trifluoromethoxy-biphenyl-4-yl)-carbamic acid tert.-butyl ester (Example G27) and 3-(3-cyano-phenyl)-3-oxo-propionic acid ethyl ester (*Pol J. Chem.* 1978, 25) according to the general procedure K. Obtained as a brown semisolid (94 mg).

MS (ISP) 540 [(M+H)$^+$], 557 [(M+NH4)$^+$] and 562 [(M+Na)$^+$].

Example K25

4-{4-tert.-Butoxycarbonylamino-3-[3-(3-cyano-phenyl)-3-oxo-propionylamino]-phenyl}-3,6-dihydro-2H-pyridine-1-carboxylic acid tert.-butyl ester Prepared from 4-(3-amino-4-tert.-butoxycarbonylamino-phenyl)-3,6-dihydro-2H-pyridine-1-carboxylic acid tert.-butyl ester (Example G29) (544 mg, 1.4 mmol) and 3-(2,2-dimethyl-6-oxo-6H-[1,3]dioxin-4-yl)-benzonitrile (Example J4) (336 mg, 1.5 mmol) according to the general procedure K. Obtained as an orange solid (722 mg).

MS (ISP) 561 [(M+H)$^+$]; mp 75–79° C. (dec.).

Example K26

{4-(6-Benzyloxy-pyridin-3-yl)-2-[3-(3-chloro-thiophen-2-yl)-3-oxo-propionylamino]-phenyl}-carbamic acid tert.-butyl ester Prepared from [2-amino-4-(6-benzyloxy-pyridin-3-yl)-phenyl]-carbamic acid tert.-butyl ester (Example G30) (216 mg, 0.55 mmol) and 6-(3-chloro-thiophen-2-yl)-2,2-dimethyl-[1,3]dioxin-4-one (Example J2) (142 mg, 0.58 mmol) according to the general procedure K. Obtained as a beige solid (172 mg).

MS (ISP) 578 [(M+H)$^+$]; mp 158–159° C. (dec.).

Example K27

{2-[3-(3-Imidazol-1-yl-phenyl)-3-oxo-propionylamino]-4-phenylethynyl-phenyl}-carbamic acid tert.-butyl ester Prepared from (2-amino-4-phenylethynyl-phenyl)-carbamic acid tert.-butyl ester (Example G2) (154 mg, 0.5 mmol) and 6-(3-imidazol-1-yl-phenyl)-2,2-dimethyl-[1,3]dioxin-4-one (Example J10) (135 mg, 0.5 mmol) according to the general procedure K. Obtained as an orange oil (179 mg).
MS (ISN) 519 [(M−H)⁻].

Example K28

{4-Benzofuran-2-yl-2-[3-(3-cyano-phenyl)-3-oxo-propionylamino]-phenyl}-carbamic acid tert.-butyl ester Prepared from (2-amino-4-benzofuran-2-yl-phenyl)-carbamic acid tert.-butyl ester (Example G46) (324 mg, 1.0 mmol) and 3-(2,2-dimethyl-6-oxo-6H-[1,3]dioxin-4-yl)-benzonitrile (Example J4) (252 mg, 1.1 mmol) according to the general procedure K. Obtained as a yellow solid (299 mg).
MS (ISP) 496 [(M+H)⁺]; mp 115° C.

Example K29

{3-[3-(3-Cyano-phenyl)-3-oxo-propionylamino]-[1,1';4',1"]terphenyl-4-yl}-carbamic acid tert.-butyl ester Prepared from (3"-amino-[1,1';4',1"]terphenyl-4"-yl)-carbamic acid tert.-butyl ester (Example G32) (159 mg, 0.44 mmol) and 3-(2,2-dimethyl-6-oxo-6H-[1,3]dioxin-4-yl)-benzonitrile (Example J4) (111 mg, 0.49 mmol) according to the general procedure K. Obtained as an off-white solid (156 mg).
MS (ISN) 530 [(M−H)⁻]; mp 214–216° C.

Example K30

[2-[3-(3-Cyano-phenyl)-3-oxo-propionylamino]-4-(4-trifluoromethoxy-phenylethynyl)-phenyl]-carbamic acid tert.-butyl ester Prepared from [2-amino-4-(4-trifluoromethoxy-phenylethynyl)-phenyl]-carbamic acid tert.-butyl ester (Example G36) (196 mg, 0.5 mmol) and 3-(2,2-dimethyl-6-oxo-6H-[1,3]dioxin-4-yl)-benzonitrile (Example J4) (126 mg, 0.55 mmol) according to the general procedure K. Obtained as an off-white solid (175 mg).
MS (ISP) 564 [(M+H)⁺]; mp 152–154° C.

Example K31

{2-[3-(3-Nitro-phenyl)-3-oxo-propionylamino]-4-phenylethynyl-phenyl}-carbamic acid tert.-butyl ester Prepared from (2-amino-4-phenylethynyl-phenyl)-carbamic acid tert.-butyl ester (Example G2) (1.1 g, 4.0 mmol) and 2,2-dimethyl-6-(3-nitro-phenyl)-[1,3]dioxin-4-one (Example J12) (1.23 g, 4.4 mmol) according to the general procedure K. Obtained as a light yellow solid (989 mg).
MS (ISN) 498 [(M−H)⁻]; mp 177–179° C.

Example K32

{3-[3-(3-Cyano-phenyl)-3-oxo-propionylamino]-4'-fluoro-biphenyl-4-yl}-carbamic acid tert.-butyl ester Prepared from (3-amino-4'-fluoro-biphenyl-4-yl)-carbamic acid tert.-butyl ester (Example G39) and 3-(2,2-dimethyl-6-oxo-6H-[1,3]dioxin-4-yl)-benzonitrile (Example J4) according to the general procedure K. Obtained as a yellow solid (257 mg).
MS (ISP) 474 [(M+H)⁺]; mp 177–179° C.

Example K33

{4-(4-Fluoro-phenylethynyl)-2-[3-(3-imidazol-1-yl-phenyl)-3-oxo-propionylamino]-phenyl}-carbamic acid tert.-butyl ester Prepared from [2-amino-4-(4-fluoro-phenylethynyl)-phenyl]-carbamic acid tert.-butyl ester (Example G33) and 6-(3-imidazol-1-yl-phenyl)-2,2-dimethyl-[1,3]dioxin-4-one (Example J10) according to the general procedure K. Obtained as an orange oil (207 mg).
MS (ISN) 537 [(M−H)⁻].

Example K34

{3-[3-(3-Imidazol-1-yl-phenyl)-3-oxo-propionylamino]-biphenyl-4-yl}-carbamic acid tert.-butyl ester Prepared from (3-amino-biphenyl-4-yl)-carbamic acid tert.-butyl ester (Example G9) (142 mg, 0.5 mmol) and 6-(3-imidazol-1-yl-phenyl)-2,2-dimethyl-[1,3]dioxin-4-one (Example J10) (170 mg, 0.63 mmol) according to the general procedure K. Obtained as a light yellow foam (248 mg).
MS (ISN) 495 [(M−H)⁻].

Example K35

{4'-Fluoro-3-[3-(3-imidazol-1-yl-phenyl)-3-oxo-propionylamino]-biphenyl-4-yl}-carbamic acid tert.-butyl ester Prepared from (3-amino-4'-fluoro-biphenyl-4-yl)-carbamic acid tert.-butyl ester (Example G39) and 6-(3-imidazol-1-yl-phenyl)-2,2-dimethyl-[1,3]dioxin-4-one (Example J10) according to the general procedure K. Obtained as a light yellow solid (489 mg).
MS (ISN) 513 [(M−H)⁻].

Example K36

(3-Amino-4'-methoxy-biphenyl-4-yl)-carbamic acid tert.-butyl ester

Prepared from (3-amino-4'-methoxy-biphenyl-4-yl)-carbamic acid tert.-butyl ester (Example G5) and 6-(3-imidazol-1-yl-phenyl)-2,2-dimethyl-[1,3]dioxin-4-one (Example J10) according to the general procedure K. Obtained as a yellow liquid (195 mg).

Example K37

{4-(4-Fluoro-phenylethynyl)-2-[3-oxo-3-(3-[1,2,4]triazol-1-yl-phenyl)-propionylamino]-phenyl}-carbamic acid tert.-butyl ester Prepared from [2-amino-4-(4-fluoro-phenylethynyl)-phenyl]-carbamic acid tert.-butyl ester (Example G33) and 2,2-dimethyl-6-(3-[1,2,4]triazol-1-yl-phenyl)-[1,3]dioxin-4-one (Example J13) according to the general procedure K. Obtained as a yellow solid (230 mg).

mp 131–139° C.

Example K38

{4-(2-Fluoro-phenylethynyl)-2-[3-(3-imidazol-1-yl-phenyl)-3-oxo-propionylamino]-phenyl}-carbamic acid tert.-butyl ester Prepared from [2-amino-4-(2-fluoro-phenylethynyl)-phenyl]-carbamic acid tert.-butyl ester (Example G34) (245 mg, 0.75 mmol) and 6-(3-imidazol-1-yl-phenyl)-2,2-dimethyl-[1,3]dioxin-4-one (Example J10) (300 mg, 1.1 mmol) according to the general procedure K. Obtained as a yellow-brown foam (211 mg).

MS (ISN) 537 [(M−H)⁻].

Example K39

{4'-Fluoro-3-[3-oxo-3-(3-[1,2,4]triazol-1-yl-phenyl)-propionylamino]-biphenyl-4-yl}-carbamic acid tert.-butyl ester Prepared from (3-amino-4'-fluoro-biphenyl-4-yl)-carbamic acid tert.-butyl ester (Example G39) and 2,2-dimethyl-6-(3-[1,2,4]triazol-1-yl-phenyl)-[1,3]dioxin-4-one (Example J13) according to the general procedure K. Obtained as an orange foam (233 mg).

Example K40

{4'-Cyano-3-[3-(3-cyano-phenyl)-3-oxo-propionylamino]-biphenyl-4-yl}-carbamic acid tert.-butyl ester Prepared from (3-amino-4'-cyano-biphenyl-4-yl)-carbamic acid tert.-butyl ester (Example G40) and 3-(2,2-dimethyl-6-oxo-6H-[1,3]dioxin-4-yl)-benzonitrile (Example J4) according to the general procedure K. Obtained as a light red solid (185 mg).

Example K41

{4'-Cyano-3-[3-(3-imidazol-1-yl-phenyl)-3-oxo-propionylamino]-biphenyl-4-yl}-carbamic acid tert.-butyl ester Prepared from (3-amino-4'-cyano-biphenyl-4-yl)-carbamic acid tert.-butyl ester (Example G40) and 6-(3-imidazol-1-yl-phenyl)-2,2-dimethyl-[1,3]dioxin-4-one (Example J10) according to the general procedure K. Obtained as a yellow solid (228 mg).

Example K42

{4'-Fluoro-3-[3-(3-nitro-phenyl)-3-oxo-propionylamino]-biphenyl-4-yl}-carbamic acid tert.-butyl ester Prepared from (3-amino-4'-fluoro-biphenyl-4-yl)-carbamic acid tert.-butyl ester (Example G39) and 2,2-dimethyl-6-(3-nitro-phenyl)-[1,3]dioxin-4-one (Example J12) according to the general procedure K. Obtained as a light yellow solid (1.01 g).

Example K43

{4-(4-Fluoro-phenylethynyl)-2-[3-(2-imidazol-1-yl-pyridin-4-yl)-3-oxo-propionylamino]-phenyl}-carbamic acid tert.-butyl ester Prepared from [2-amino-4-(4-fluoro-phenylethynyl)-phenyl]-carbamic acid tert.-butyl ester (Example G33) and 6-(2-imidazol-1-yl-pyridin-4-yl)-2,2-dimethyl-[1,3]dioxin-4-one (Example J14) according to the general procedure K. Obtained as a brown solid (284 mg).

MS (ISP) 540 [(M+H)⁺]; mp 169° C.

Example K44

{4'-Fluoro-3-[3-(2-imidazol-1-yl-pyridin-4-yl)-3-oxo-propionylamino]-biphenyl-4-yl}-carbamic acid tert.-butyl ester Prepared from (3-amino-4'-fluoro-biphenyl-4-yl)-carbamic acid tert.-butyl ester (Example G39) and 6-(2-imidazol-1-yl-pyridin-4-yl)-2,2-dimethyl-[1,3]dioxin-4-one (Example J14) according to the general procedure K. Obtained as a brown solid (361 mg).

MS (ISP) 516 [(M+H)⁺]; mp 124° C. (dec.).

Example K45

{2'-Fluoro-3-[3-(3-imidazol-1-yl-phenyl)-3-oxo-propionylamino]-biphenyl-4-yl}-carbamic acid tert.-butyl ester Prepared from (3-amino-2'-fluoro-biphenyl-4-yl)-carbamic acid tert.-butyl ester (Example G37) and 6-(3-imidazol-1-yl-phenyl)-2,2-dimethyl-[1,3]dioxin-4-one (Example J10) according to the general procedure K. Obtained as a brown solid (352 mg).

MS (ISP) 515 [(M+H)⁺]; mp 50–58° C.

Example K46

{4-(6-Benzyloxy-pyridin-3-yl)-2-[3-(3-imidazol-1-yl-phenyl)-3-oxo-propionylamino]-phenyl}-carbamic acid tert.-butyl ester Prepared from [2-amino-4-(6-benzyloxy-pyridin-3-yl)-phenyl]-carbamic acid tert.-butyl ester (Example G30) (196 mg, 0.5 mmol) and 6-(3-imidazol-1-yl-phenyl)-2,2-dimethyl-[1,3]dioxin-4-one (Example J10) (229 mg, 0.85 mmol) according to the general procedure K. Obtained as a yellow solid (209 mg).

MS (ISN) 602 [(M−H)⁻]; mp 79–83° C.

Example K47

(4'-Fluoro-3-{3-[3-(4-methyl-imidazol-1-yl)-phenyl]-3-oxo-propionylamino}-biphenyl-4-yl)-carbamic acid tert.-butyl ester Prepared from (3-amino-4'-fluoro-biphenyl-4-yl)-carbamic acid tert.-butyl ester (Example G39) (362 mg, 1.2 mmol) and 3-[3-(4-methyl-imidazol-1-yl)-phenyl]-3-oxo-propionic acid tert.-butyl ester (Example H7) (300 mg, 1.0 mmol) according to the general procedure K. Obtained as a light yellow solid (392 mg).
MS (ISP) 529 [(M+H)$^+$]; mp 124° C.

Example K48

{2'-Fluoro-3-[3-(2-imidazol-1-yl-pyridin-4-yl)-3-oxo-propionylamino]-biphenyl-4-yl}-carbamic acid tert.-butyl ester Prepared from (3-amino-2'-fluoro-biphenyl-4-yl)-carbamic acid tert.-butyl ester (Example G37) and 6-(2-imidazol-1-yl-pyridin-4-yl)-2,2-dimethyl-[1,3]dioxin-4-one (Example J14) according to the general procedure K. Obtained as an orange solid (103 mg).
MS (ISP) 516 [(M+H)$^+$].

Example K49

(4-(4-Fluoro-phenylethynyl)-2-{3-[3-(4-methyl-imidazol-1-yl)-phenyl]-3-oxo-propionylamino}-phenyl)-carbamic acid tert.-butyl ester Prepared from [2-amino-4-(4-fluoro-phenylethynyl)-phenyl]-carbamic acid tert.-butyl ester (Example G33) (392 mg, 1.2 mmol) and 3-[3-(4-methyl-imidazol-1-yl)-phenyl]-3-oxo-propionic acid tert.-butyl ester (Example H7) (300 mg, 1.0 mmol) according to the general procedure K. Obtained as a yellow solid (407 mg).
MS (ISP) 553 [(M+H)$^+$]; mp 166° C.

Example K50

{4'-Fluoro-3-[3-(3-imidazol-1-yl-phenyl)-3-oxo-propionylamino]-2'-methyl-biphenyl-4-yl}-carbamic acid tert.-butyl ester Prepared from (3-amino-3'-fluoro-biphenyl-4-yl)-carbamic acid tert.-butyl ester (Example G41) (158 mg, 0.5 mmol) and 6-(3-imidazol-1-yl-phenyl)-2,2-dimethyl-[1,3]dioxin-4-one (Example J10) (186 mg, 0.69 mmol) according to the general procedure K. Obtained as an orange oil (168 mg).
MS (ISP) 529 [(M+H)$^+$].

Example K51

{4'-Fluoro-3-[3-(3-imidazol-1-yl-phenyl)-3-oxo-propionylamino]-2'-methoxymethoxy-biphenyl-4-yl}-carbamic acid tert.-butyl ester Prepared from (3-amino-4'-fluoro-2'-methoxymethoxy-biphenyl-4-yl)-carbamic acid tert.-butyl ester (Example G42) (181 mg, 0.5 mmol) and 6-(3-imidazol-1-yl-phenyl)-2,2-dimethyl-[1,3]dioxin-4-one (Example J10) (135 mg, 0.5 mmol) according to the general procedure K. Obtained as a yellow amorphous substance (221 mg).
MS (ISN) 573 [(M−H)$^−$].

Example K52

(2'-Fluoro-3-{3-[3-(2-methyl-imidazol-1-yl)-phenyl]-3-oxo-propionylamino}-biphenyl-4-yl)-carbamic acid tert.-butyl ester Prepared from (3-amino-2'-fluoro-biphenyl-4-yl)-carbamic acid tert.-butyl ester (Example G37) (362 mg, 1.2 mmol) and 3-[3-(2-methyl-imidazol-1-yl)-phenyl]-3-oxo-propionic acid tert.-butyl ester (Example H8) (300 mg, 1.0 mmol) according to the general procedure K. Obtained as a yellow amorphous substance (312 mg).
MS (ISP) 529 [(M+H)$^+$].

Example K53

(4'-Fluoro-3-{3-[3-(2-methyl-imidazol-1-yl)-phenyl]-3-oxo-propionylamino}-biphenyl-4-yl)-carbamic acid tert.-butyl ester Prepared from (3-amino-4'-fluoro-biphenyl-4-yl)-carbamic acid tert.-butyl ester (Example G39) (362 mg, 1.2 mmol) and 3-[3-(2-methyl-imidazol-1-yl)-phenyl]-3-oxo-propionic acid tert.-butyl ester (Example H8) (300 mg, 1.0 mmol) according to the general procedure K. Obtained as a yellow amorphous substance (302 mg).
MS (ISP) 529 [(M+H)$^+$].

Example K54

{3-[3-(3-Cyano-thiophen-2-yl)-3-oxo-propionylamino]-4'-fluoro-biphenyl-4-yl}-carbamic acid tert.-butyl ester Prepared from (3-amino-4'-fluoro-biphenyl-4-yl)-carbamic acid tert.-butyl ester (Example G39) (302 mg, 1.0 mmol) and 6-(3-cyano-thiophen-2-yl)-2,2-dimethyl-[1,3]dioxin-4-one (Example J3) (250 mg, 1.06 mmol) according to the general procedure K. Obtained as a light yellow solid (251 mg).
MS (ISP) 480 [(M+H)$^+$]; mp 156–157° C.

Example K55

{3-[3-(3-Cyano-thiophen-2-yl)-3-oxo-propionylamino]-2'-fluoro-biphenyl-4-yl}-carbamic acid tert.-butyl ester Prepared from (3-amino-2'-fluoro-biphenyl-4-yl)-carbamic acid tert.-butyl ester (Example G37) (302 mg, 1.0 mmol) and 6-(3-cyano-thiophen-2-yl)-2,2-dimethyl-[1,3]dioxin-4-one (Example J3) (280 mg, 1.19 mmol) according to the general procedure K. Obtained as a light yellow solid (446 mg).
MS (ISP) 480 [(M+H)$^+$]; mp 63–66° C.

Example K56

{4'-Fluoro-3-[3-oxo-3-(3-tetrazol-1-yl-phenyl)-propionylamino]-biphenyl-4-yl}-carbamic acid tert.-butyl ester Prepared from (3-amino-4'-fluoro-biphenyl-4-yl)-carbamic acid tert.-butyl ester (Example G39) and 3-oxo-3-(3- tetrazol-1-yl-phenyl)-propionic acid ethyl ester (Example H15) according to the general procedure K. Obtained as a light yellow solid (159 mg).

MS (ISN) 515 [(M−H)⁻].

Example K57

{3-[3-(3-Cyano-phenyl)-3-oxo-propionylamino]-2'-fluoro-biphenyl-4-yl}-carbamic acid tert.-butyl ester Prepared from (3-amino-2'-fluoro-biphenyl-4-yl)-carbamic acid tert.-butyl ester (Example G37) and 3-(2,2-dimethyl-6-oxo-6H-[1,3]dioxin-4-yl)-benzonitrile (Example J4) according to the general procedure K. Obtained as a light yellow foam (239 mg).

MS (ISP) 474 [(M+H)⁺].

Example K58

{2'-Fluoro-3-[3-oxo-3-(3-tetrazol-1-yl-phenyl)-propionylamino]-biphenyl-4-yl}-carbamic acid tert.-butyl ester Prepared from (3-amino-2'-fluoro-biphenyl-4-yl)-carbamic acid tert.-butyl ester (Example G37) and 3-oxo-3-(3-tetrazol-1-yl-phenyl)-propionic acid ethyl ester (Example H15) according to the general procedure K. Obtained as a light red solid (129 mg).

MS (ISP) 517 [(M+H)⁺].

Example K59

(3-{3-[3-(2,4-Dimethyl-imidazol-1-yl)-phenyl]-3-oxo-propionylamino}-4'-fluoro-biphenyl-4-yl)-carbamic acid tert.-butyl ester Prepared from (3-amino-4'-fluoro-biphenyl-4-yl)-carbamic acid tert.-butyl ester (Example G39) (227 mg, 0.75 mmol) and 3-[3-(2,4-dimethyl-imidazol-1-yl)-phenyl]-3-oxo-propionic acid tert.-butyl ester (Example H9) (157 mg, 0.5 mmol) according to the general procedure K. Obtained as a yellow amorphous substance (127 mg).

MS (ISP) 543 [(M+H)⁺].

Example K60

(2-{3-[3-(2,4-Dimethyl-imidazol-1-yl)-phenyl]-3-oxo-propionylamino}-4-phenylethynyl-phenyl)-carbamic acid tert.-butyl ester Prepared from (2-amino-4-phenylethynyl-phenyl)-carbamic acid tert.-butyl ester (Example G2) (231 mg, 0.75 mmol) and 3-[3-(2,4-dimethyl-imidazol-1-yl)-phenyl]-3-oxo-propionic acid tert.-butyl ester (Example H9) (157 mg, 0.5 mmol) according to the general procedure K. Obtained as a yellow amorphous substance (140 mg).

MS (ISP) 549 [(M+H)⁺].

Example K61

{3-[3-(3-Chloro-thiophen-2-yl)-3-oxo-propionylamino]-4'-fluoro-biphenyl-4-yl}-carbamic acid tert.-butyl ester Prepared from (3-amino-4'-fluoro-biphenyl-4-yl)-carbamic acid tert.-butyl ester (Example G39) (360 mg, 1.2 mmol) and 3-(3-chloro-thiophen-2-yl)-3-oxo-propionic acid ethyl ester (Example H16) (350 mg, 1.5 mmol) according to the general procedure K. Obtained as a white-yellow solid (353 mg).

MS (ISP) 489 [(M+H)⁺] and 491 [(M+2+H)⁺]; mp 168–169° C.

Example K62

{2'-Fluoro-3-[3-(3-nitro-phenyl)-3-oxo-propionylamino]-biphenyl-4-yl}-carbamic acid tert.-butyl ester Prepared from (3-amino-2'-fluoro-biphenyl-4-yl)-carbamic acid tert.-butyl ester (Example G37) and 2,2-dimethyl-6-(3-nitro-phenyl)-[1,3]dioxin-4-one (Example J12) according to the general procedure K. Obtained as a yellow solid (113 mg).

MS (ISN) 492 [(M−H)⁻]; mp 167° C.

Example K63

{3-[3-(2-Cyano-pyridin-4-yl)-3-oxo-propionylamino]-4'-fluoro-biphenyl-4-yl}-carbamic acid tert.-butyl ester Prepared from (3-amino-4'-fluoro-biphenyl-4-yl)-carbamic acid tert.-butyl ester (Example G39) and 3-(2-cyano-pyridin-4-yl)-3-oxo-propionic acid tert.-butyl ester (Example H10) according to the general procedure K. Obtained as a red solid (118 mg).

Example K64

{3-[3-(2-Cyano-pyridin-4-yl)-3-oxo-propionylamino]-2'-fluoro-biphenyl-4-yl}-carbamic acid tert.-butyl ester Prepared from (3-amino-2'-fluoro-biphenyl-4-yl)-carbamic acid tert.-butyl ester (Example G37) and 3-(2-cyano-pyridin-4-yl)-3-oxo-propionic acid tert.-butyl ester (Example H10) according to the general procedure K. Obtained as a white solid (151 mg).

mp 190° C. (dec.).

Example K65

{3-[3-(3-Cyano-phenyl)-3-oxo-propionylamino]-3'-fluoro-biphenyl-4-yl}-carbamic acid tert.-butyl ester Prepared from (3-amino-3'-fluoro-biphenyl-4-yl)-carbamic acid tert.-butyl ester (Example G38) (151 mg, 0.5 mmol) and 3-(2,2-dimethyl-6-oxo-6H-[1,3]dioxin-4-yl)-benzonitrile (Example J4) (175 mg, 0.76 mmol) according to the general procedure K. Obtained as an orange solid (141 mg).

MS (ISP) 474 [(M+H)⁺]; mp 148–150° C.

Example K66

{3'-Fluoro-3-[3-(3-imidazol-1-yl-phenyl)-3-oxo-propionylamino]-biphenyl-4-yl}-carbamic acid tert.-butyl ester Prepared from (3-amino-3'-fluoro-biphenyl-4-yl)-carbamic acid tert.-butyl ester (Example G38) (151 mg, 0.5 mmol) and 6-(3-imidazol-1-yl-phenyl)-2,2-dimethyl-[1,3]

dioxin-4-one (Example J10) (135 mg, 0.5 mmol) according to the general procedure K. Obtained as an orange solid (150 mg).

MS (ISP) 515 [(M+H)$^+$]; mp 70–83° C.

Example K67

{2-[3-(2-Cyano-pyridin-4-yl)-3-oxo-propionylamino]-4-phenylethynyl-phenyl}-carbamic acid tert.-butyl ester Prepared from (2-amino-4-phenylethynyl-phenyl)-carbamic acid tert.-butyl ester (Example G2) and 3-(2-cyano-pyridin-4-yl)-3-oxo-propionic acid tert.-butyl ester (Example H10) according to the general procedure K. Obtained as a white solid (174 mg).

mp 189° C. (dec.).

Example K68

{2'-Fluoro-3-[3-oxo-3-(3-[1,2,4]triazol-4-yl-phenyl)-propionylamino]-biphenyl-4-yl}-carbamic acid tert.-butyl ester Prepared from (3-amino-2'-fluoro-biphenyl-4-yl)-carbamic acid tert.-butyl ester (Example G37) (302 mg, 1.0 mmol) and 3-oxo-3-(3-[1,2,4]triazol-4-yl-phenyl)-propionic acid tert.-butyl ester (Example H11) (345 mg, 1.2 mmol) according to the general procedure K. Obtained as a yellow amorphous substance (207 mg).

MS (ISP) 516 [(M+H)$^+$].

Example K69

{3-[3-(5-Cyano-thiophen-2-yl)-3-oxo-propionylamino]-2'-fluoro-biphenyl-4-yl}-carbamic acid tert.-butyl ester Prepared from (3-amino-2'-fluoro-biphenyl-4-yl)-carbamic acid tert.-butyl ester (Example G37) (302 mg, 1.0 mmol) and 3-(5-cyano-thiophen-2-yl)-3-oxo-propionic acid tert.-butyl ester (Example H17) (276 mg, 1.1 mmol) according to the general procedure K. Obtained as a yellow solid (451 mg).

MS (ISP) 480 [(M+H)$^+$]; mp 201° C.

Example K70

(3-{3-[3-(2,4-Dimethyl-imidazol-1-yl)-phenyl]-3-oxo-propionylamino}-2'-fluoro-biphenyl-4-yl)-carbamic acid tert.-butyl ester Prepared from (3-amino-2'-fluoro-biphenyl-4-yl)-carbamic acid tert.-butyl ester (Example G37) (333 mg, 1.1 mmol) and 3-[3-(2,4-dimethyl-imidazol-1-yl)-phenyl]-3-oxo-propionic acid tert.-butyl ester (Example H9) (314 mg, 1.0 mmol) according to the general procedure K. Obtained as a light yellow solid (374 mg).

MS (ISP) 543 [(M+H)$^+$]; mp 145° C.

Example K71

(2'-Fluoro-3-{3-[3-(2-methoxymethylsulfanyl-imidazol-1-yl)-phenyl]-3-oxo-propionylamino}-biphenyl-4-yl)-carbamic acid tert.-butyl ester Prepared from (3-amino-2'-fluoro-biphenyl-4-yl)-carbamic acid tert.-butyl ester (Example G37) (303 mg, 1.0 mmol) and 3-[3-(2-methoxymethylsulfanyl-imidazol-1-yl)-phenyl]-3-oxo-propionic acid tert.-butyl ester (Example H12) (512 mg, 1.41 mmol) according to the general procedure K. Obtained as a light yellow solid (552 mg).

MS (ISN) 589 [(M−H)$^-$]; mp 83–86° C.

Example K72

{3-[3-(5-Cyano-2-fluoro-phenyl)-3-oxo-propionylamino]-2'-fluoro-biphenyl-4-yl}-carbamic acid tert.-butyl ester Prepared from (3-amino-2'-fluoro-biphenyl-4-yl)-carbamic acid tert.-butyl ester (Example G37) (302 mg, 1.0 mmol) and 3-(5-cyano-2-fluoro-phenyl)-3-oxo-propionic acid ethyl ester (Example H18) (362 mg, 1.5 mmol) according to the general procedure K. Obtained as a yellow-brown solid (352 mg).

MS (ISP) 492 [(M+H)$^+$]; mp 170° C.

Example K73

{3-[3-(2-Cyano-pyridin-4-yl)-3-oxo-propionylamino]-2',4'-difluoro-biphenyl-4-yl}-carbamic acid tert.-butyl ester Prepared from (3-amino-2',4'-difluoro-biphenyl-4-yl)-carbamic acid tert.-butyl ester (Example G43) and 3-(2-cyano-pyridin-4-yl)-3-oxo-propionic acid tert.-butyl ester (Example H10) according to the general procedure K. Obtained as a light brown solid (207 mg).

MS (ISN) 491 [(M−H)$^-$]; mp 160–161° C.

Example K74

{2-[3-(2-Cyano-pyridin-4-yl)-3-oxo-propionylamino]-4-isopropyl-phenyl}-carbamic acid tert.-butyl ester Prepared from (2-amino-4-isopropyl-phenyl)-carbamic acid tert.-butyl ester (Example G47) and 3-(2-cyano-pyridin-4-yl)-3-oxo-propionic acid tert.-butyl ester (Example H10) according to the general procedure K. Obtained as a light brown solid (183 mg).

MS (ISN) 421 [(M−H)$^-$]; mp 163–165° C.

Example K75

(2'-Fluoro-3-{3-[2-(4-methyl-imidazol-1-yl)-thiazol-4-yl]-3-oxo-propionylamino}-biphenyl-4-yl)-carbamic acid tert.-butyl ester Prepared from (3-amino-2'-fluoro-biphenyl-4-yl)-carbamic acid tert.-butyl ester (Example G37) (151 mg, 0.5 mmol) and 3-[2-(4-methyl-imidazol-1-yl)-thiazol-4-yl]-3-oxo-propionic acid tert.-butyl ester (Example H20) (154 mg, 0.5 mmol) according to the general procedure K. Obtained as a yellow amorphous substance (157 mg).

MS (ISN) 534 [(M−H)$^-$].

Example K76

(4'-Fluoro-3-{3-[2-(4-methyl-imidazol-1-yl)-thiazol-4-yl]-3-oxo-propionylamino}-biphenyl-4-yl)-carbamic acid tert.-butyl ester Prepared from (3-amino-4'-fluoro-biphenyl-4-yl)-carbamic acid tert.-butyl ester (Example G39) (151 mg, 0.5 mmol) and 3-[2-(4-methyl-imidazol-1-yl)-thiazol-4-yl]-3-oxo-propionic acid tert.-butyl ester (Example H20) (154 mg, 0.5 mmol) according to the general procedure K. Obtained as a yellow amorphous substance (225 mg).
MS (ISN) 534 [(M−H)⁻].

Example K77

{2'-Fluoro-3-[3-oxo-3-(3-[1,2,3]triazol-1-yl-phenyl)-propionylamino]-biphenyl-4-yl}-carbamic acid tert.-butyl ester Prepared from (3-amino-2'-fluoro-biphenyl-4-yl)-carbamic acid tert.-butyl ester (Example G37) (152 mg, 0.5 mmol) and 3-oxo-3-(3-[1,2,3]triazol-1-yl-phenyl)-propionic acid ethyl ester (Example H2) (200 mg, 0.77 mmol) according to the general procedure K. Obtained as a yellow oil (191 mg).
MS (ISP) 516 [(M+H)⁺].

Example K78

{2-[3-(3-Cyano-phenyl)-3-oxo-propionylamino]-4-cyclopropyl-phenyl}-carbamic acid tert.-butyl ester Prepared from (2-amino-4-cyclopropyl-phenyl)-carbamic acid tert.-butyl ester (Example G48) and 3-(2,2-dimethyl-6-oxo-6H-[1,3]dioxin-4-yl)-benzonitrile (Example J4) according to the general procedure K. Obtained as a light brown solid (92 mg).
MS (EI) 419 (M⁺).

Example K79

{2-[3-(2-Cyano-pyridin-4-yl)-3-oxo-propionylamino]-4-cyclopropyl-phenyl}-carbamic acid tert.-butyl ester Prepared from (2-amino-4-cyclopropyl-phenyl)-carbamic acid tert.-butyl ester (Example G48) and 4-(2,2-dimethyl-6-oxo-6H-[1,3]dioxin-4-yl)-pyridine-2-carbonitrile (Example J16) according to the general procedure K. Obtained as a light brown solid (148 mg).
MS (ISP) 421 [(M+H)⁺].

Example K80

{4-Cyclopropyl-2-[3-(3-imidazol-1-yl-phenyl)-3-oxo-propionylamino]-phenyl}-carbamic acid tert.-butyl ester Prepared from (2-amino-4-cyclopropyl-phenyl)-carbamic acid tert.-butyl ester (Example G48) and 6-(3-imidazol-1-yl-phenyl)-2,2-dimethyl-[1,3]dioxin-4-one (Example J10) according to the general procedure K. Obtained as a light yellow solid (79 mg).
MS (ISP) 461 [(M+H)⁺].

Example K81

{4'-Fluoro-3-[3-oxo-3-(3-[1,2,3]triazol-1-yl-phenyl)-propionylamino]-biphenyl-4-yl}-carbamic acid tert.-butyl ester Prepared from (3-amino-4'-fluoro-biphenyl-4-yl)-carbamic acid tert.-butyl ester (Example G39) (152 mg, 0.5 mmol) and 3-oxo-3-(3-[1,2,3]triazol-1-yl-phenyl)-propionic acid ethyl ester (Example H2) (200 mg, 0.77 mmol) according to the general procedure K. Obtained as a yellow oil (107 mg).
MS (ISP) 516 [(M+H)⁺].

Example K82

{4-(4-Fluoro-phenylethynyl)-2-[3-oxo-3-(3-[1,2,3]triazol-1-yl-phenyl)-propionylamino]-phenyl}-carbamic acid tert.-butyl ester Prepared from [2-amino-4-(4-fluoro-phenylethynyl)-phenyl]-carbamic acid tert.-butyl ester (Example G33) (163 mg, 0.5 mmol) and 3-oxo-3-(3-[1,2,3]triazol-1-yl-phenyl)-propionic acid ethyl ester (Example H2) (181 mg, 0.7 mmol) according to the general procedure K. Obtained as a yellow oil (107 mg).
MS (ISP) 540 [(M+H)⁺].

Example K83

{4'-Fluoro-3-[3-(2-imidazol-1-yl-thiazol-4-yl)-3-oxo-propionylamino]-biphenyl-4-yl}-carbamic acid tert.-butyl ester Prepared from (3-amino-4'-fluoro-biphenyl-4-yl)-carbamic acid tert.-butyl ester (Example G39) (151 mg, 0.5 mmol) and 3-(2-imidazol-1-yl-thiazol-4-yl)-3-oxo-propionic acid tert.-butyl ester (Example H19) (235 mg, 0.8 mmol) according to the general procedure K. Obtained as an orange oil (162 mg).
MS (ISP) 522 [(M+H)⁺].

Example K84

(4'-Fluoro-3-{3-[3-(3-methyl-isoxazol-5-yl)-phenyl]-3-oxo-propionylamino}-biphenyl-4-yl)-carbamic acid tert.-butyl ester Prepared from (3-amino-4'-fluoro-biphenyl-4-yl)-carbamic acid tert.-butyl ester (Example G39) (151 mg, 0.5 mmol) and 3-[3-(3-methyl-isoxazol-5-yl)-phenyl]-3-oxo-propionic acid tert.-butyl ester (Example H14) (190 mg, 0.63 mmol) according to the general procedure K. Obtained as an off-white solid (86 mg).
MS (ISP) 530 [(M+H)⁺]; mp 100–101° C.

Example K85

{3-[3-(3-Cyano-phenyl)-3-oxo-propionylamino]-2',4'-difluoro-biphenyl-4-yl}-carbamic acid tert.-butyl ester Prepared from (3-amino-2',4'-difluoro-biphenyl-4-yl)-carbamic acid tert.-butyl ester (Example G43) and 3-(2,2-dimethyl-6-oxo-6H-[1,3]dioxin-4-yl)-benzonitrile (Example J4) according to the general procedure K. Obtained as an orange oil (95 mg).
MS (ISP) 492 [(M+H)⁺].

Example K86

{2-[3-(3-Cyano-phenyl)-3-oxo-propionylamino]-4-isopropyl-phenyl}-carbamic acid tert.-butyl ester Prepared from (2-amino-4-isopropyl-phenyl)-carbamic acid tert.-butyl ester (Example G47) and 3-(2,2-dimethyl-6- oxo-6H-[1,3]dioxin-4-yl)-benzonitrile (Example J4) according to the general procedure K. Obtained as a light red solid (100 mg).

MS (ISP) 422 [(M+H)$^+$]; mp 179–180° C.

Example K87

(4'-Fluoro-3-{3-[3-(2-methylsulfanyl-imidazol-1-yl)-phenyl]-3-oxo-propionylamino}-biphenyl-4-yl)-carbamic acid tert.-butyl ester Prepared from (3-amino-4'-fluoro-biphenyl-4-yl)-carbamic acid tert.-butyl ester (Example G39) and 3-[3-(2-methylsulfanyl-imidazol-1-yl)-phenyl]-3-oxo-propionic acid tert.-butyl ester (Example H13) according to the general procedure K. Obtained as a light yellow oil (181 mg).

MS (ISP) 561 [(M+H)$^+$].

Example K88

(4-Isopropyl-2-{3-[3-(2-methyl-imidazol-1-yl)-phenyl]-3-oxo-propionylamino}-phenyl)-carbamic acid tert.-butyl ester Prepared from (2-amino-4-isopropyl-phenyl)-carbamic acid tert.-butyl ester (Example G47) and 2,2-dimethyl-6-[3-(2-methyl-imidazol-1-yl)-phenyl]-[1,3]dioxin-4-one (Example J15) according to the general procedure K. Obtained as a yellow oil (186 mg).

MS (ISP) 477 [(M+H)$^+$].

Example K89

(2',4'-Difluoro-3-{3-[3-(2-methyl-imidazol-1-yl)-phenyl]-3-oxo-propionylamino}-biphenyl-4-yl)-carbamic acid tert.-butyl ester Prepared from (3-amino-2',4'-difluoro-biphenyl-4-yl)-carbamic acid tert.-butyl ester (Example G43) and 2,2-dimethyl-6-[3-(2-methyl-imidazol-1-yl)-phenyl]-[1,3]dioxin-4-one (Example J15) according to the general procedure K. Obtained as a yellow oil (145 mg).

MS (ISP) 547 [(M+H)$^+$].

Example K90

{2',4'-Difluoro-3-[3-oxo-3-(3-[1,2,3]triazol-1-yl-phenyl)-propionylamino]-biphenyl-4-yl}-carbamic acid tert.-butyl ester Prepared from (3-amino-2',4'-difluoro-biphenyl-4-yl)-carbamic acid tert.-butyl ester (Example G43) and 3-oxo-3-(3-[1,2,3]triazol-1-yl-phenyl)-propionic acid ethyl ester (Example H2) according to the general procedure K. Obtained as a light yellow oil (164 mg).

MS (ISP) 534 [(M+H)$^+$].

Example K91

{2'-Fluoro-3-[3-(2-imidazol-1-yl-thiazol-4-yl)-3-oxo-propionylamino]-biphenyl-4-yl}-carbamic acid tert.-butyl ester Prepared from (3-amino-2'-fluoro-biphenyl-4-yl)-carbamic acid tert.-butyl ester (Example G37) (151 mg, 0.5 mmol) and 3-(2-imidazol-1-yl-thiazol-4-yl)-3-oxo-propionic acid tert.-butyl ester (Example H19) (235 mg, 0.8 mmol) according to the general procedure K. Obtained as a white solid (98 mg).

MS (ISP) 522 [(M+H)$^+$]; mp 115–130° C.

Example K92

{3-[3-(3-Cyano-phenyl)-3-oxo-propionylamino]-2',5'-difluoro-biphenyl-4-yl}-carbamic acid tert.-butyl ester Prepared from (3-amino-2',5'-difluoro-biphenyl-4-yl)-carbamic acid tert.-butyl ester (Example G45) (160 mg, 0.5 mmol) and 3-(2,2-dimethyl-6-oxo-6H-[1,3]dioxin-4-yl)-benzonitrile (Example J4) (115 mg, 0.5 mmol) according to the general procedure K. Obtained as an amorphous white substance (110 mg).

MS (ISN) 490 [(M−H)$^-$].

Example K93

{2',5'-Difluoro-3-[3-oxo-3-(3-[1,2,3]triazol-1-yl-phenyl)-propionylamino]-biphenyl-4-yl}-carbamic acid tert.-butyl ester Prepared from (3-amino-2',5'-difluoro-biphenyl-4-yl)-carbamic acid tert.-butyl ester (Example G45) (160 mg, 0.5 mmol) and 3-oxo-3-(3-[1,2,3]triazol-1-yl-phenyl)-propionic acid ethyl ester (Example H2) (130 mg, 0.5 mmol) according to the general procedure K. Obtained as an amorphous off-white substance (129 mg).

MS (ISN) 532 [(M−H)$^-$].

Example K94

(2'-Fluoro-3-{3-[3-(3-methyl-isoxazol-5-yl)-phenyl]-3-oxo-propionylamino}-biphenyl-4-yl)-carbamic acid tert.-butyl ester Prepared from (3-amino-2'-fluoro-biphenyl-4-yl)-carbamic acid tert.-butyl ester (Example G37) (151 mg, 0.5 mmol) and 3-[3-(3-methyl-isoxazol-5-yl)-phenyl]-3-oxo-propionic acid tert.-butyl ester (Example H14) (190 mg, 0.63 mmol) according to the general procedure K. Obtained as a white solid (213 mg).

MS (ISN) 528 [(M−H)$^-$]; mp 158–160° C.

Example K95

{2',3'-Difluoro-3-[3-oxo-3-(3-[1,2,3]triazol-1-yl-phenyl)-propionylamino]-biphenyl-4-yl}-carbamic acid tert.-butyl ester Prepared from (3-amino-2',3'-difluoro-biphenyl-4-yl)-carbamic acid tert.-butyl ester (Example G49) (160 mg, 0.5 mmol) and 3-oxo-3-(3-[1,2,3]triazol-1-yl-phenyl)-propionic acid ethyl ester (Example H2) (130 mg, 0.5 mmol) according to the general procedure K. Obtained as an amorphous yellow substance (166 mg).

MS (ISP) 534 [(M+H)$^+$].

Example K96

[2-[3-(3-Cyano-phenyl)-3-oxo-propionylamino]-4-(2,4-difluoro-phenylethynyl)-phenyl]-carbamic acid tert.-butyl ester Prepared from [2-amino-4-(2,4-difluoro-phenylethynyl)-phenyl]-carbamic acid tert.-butyl ester (Example G35) (172 mg, 0.5 mmol) and 3-(2,2-dimethyl-6-oxo-6H-[1,3]dioxin-4-yl)-benzonitrile (Example J4) (126 mg, 0.55 mmol) according to the general procedure K. Obtained as an orange oil (198 mg).

MS (ISP) 516 [(M+H)$^+$].

Example K97

[2-[3-(3-Cyano-phenyl)-3-oxo-propionylamino]-4-(2-fluoro-phenylethynyl)-phenyl]-carbamic acid tert.-butyl ester Prepared from [2-amino-4-(2-fluoro-phenylethynyl)-phenyl]-carbamic acid tert.-butyl ester (Example G34) (163 mg, 0.5 mmol) and 3-(2,2-dimethyl-6-oxo-6H-[1,3]dioxin-4-yl)-benzonitrile (Example J4) (126 mg, 0.55 mmol) according to the general procedure K. Obtained as a brown solid (143 mg).

MS (ISN) 496 [(M−H)$^-$]; mp 216–217° C.

Example K98

[2-[3-(3-Cyano-phenyl)-3-oxo-propionylamino]-4-(4-fluoro-phenylethynyl)-phenyl]-carbamic acid tert.-butyl ester Prepared from [2-amino-4-(4-fluoro-phenylethynyl)-phenyl]-carbamic acid tert.-butyl ester (Example G33) (245 mg, 0.75 mmol) and 3-(2,2-dimethyl-6-oxo-6H-[1,3]dioxin-4-yl)-benzonitrile (Example J4) (190 mg, 0.825 mmol) according to the general procedure K. Obtained as a yellow oil (318 mg).

MS (ISN) 496 [(M−H)$^-$].

General Procedure M (Synthetic Scheme B)

Preparation of 4,8-diaryl-1,3-dihydro-benzo[b][1,4]diazepin-2-ones, 4-aryl-8-aroyl-1,3-dihydro-benzo[b][1,4]diazepin-2-ones or 4-aryl-8-arylethynyl-1,3-dihydro-benzo[b][1,4]diazepin-2-ones A suspension of the {2-[3-aryl-3-oxo-propionylamino]-4-aryl-phenyl}-carbamic acid tert.-butyl ester or {2-[3-aryl-3-oxo-propionylamino]-4-arylethynyl-phenyl}-carbamic acid tert.-butyl ester (1.0 mmol) in CH$_2$Cl$_2$ (5 mL) [anisole or 1,3-dimethoxybenzene (5 to 25 mmol) can be added if necessary] was treated with TFA (0.5–5.0 mL) at 0° C. and stirring was continued at 23° C. until tlc indicated complete consumption of the starting material. The solvent was removed in vacuum, the residue treated with little ether, whereupon it crystallized. The solid was stirred with sat. NaHCO$_3$-sol., filtered, washed with H$_2$O and ether or mixtures of ether/hexane and was dried to give the title compound, which if necessary can be purified by crystallization from THF/CH$_2$Cl$_2$/ether/hexane.

Example 1

3-(7-Iodo-4-oxo-4,5-dihydro-3H-benzo[b][1,4]diazepin-2-yl)-benzonitrile

Prepared from {2-[3-(3-cyano-phenyl)-3-oxo-propionylamino]-4-iodo-phenyl}-carbamic acid tert.-butyl ester (Example K1) (1.15 g, 2.3 mmol) by treatment with TFA in CH$_2$Cl$_2$ according to the general procedure M. Obtained as a yellow solid (880 mg).

MS (EI) 387 (M$^+$); mp 198–200° C. (dec.)

Example 2

3-(4-Oxo-7-phenylethynyl-4,5-dihydro-3H-benzo[b][1,4]diazepin-2-yl)-benzonitrile Prepared from {2-[3-(3-cyano-phenyl)-3-oxo-propionylamino]-4-phenylethynyl-phenyl}-carbamic acid tert.-butyl ester (Example K2) (230 mg, 0.48 mmol) by treatment with TFA in CH$_2$Cl$_2$ according to the general procedure M. Obtained as a light yellow solid (135 mg).

MS (EI) 361 (M$^+$); mp 245° C. (dec.)

Example 3

3-(4-Oxo-7-p-tolylethynyl-4,5-dihydro-3H-benzo[b][1,4]diazepin-2-yl)-benzonitrile Prepared from (2-amino-4-p-tolylethynyl-phenyl)-carbamic acid tert.-butyl ester (Example G3) (161 mg, 0.5 mmol) and 3-(2,2-dimethyl-6-oxo-6H-[1,3]dioxin-4-yl)-benzonitrile (Example J4) (183 mg, 0.6 mmol) according to the general procedure K. Obtained as a light yellow solid (228 mg). This material was deprotected and cyclized by treatment with TFA in CH$_2$Cl$_2$ according to the general procedure M. obtained as a light yellow solid (86 mg).

MS (EI) 375 (M$^+$); mp 236–239° C. (dec.).

Example 4

3-[7-(2-Chloro-phenylethynyl)-4-oxo-4,5-dihydro-3H-benzo[b][1,4]diazepin-2-yl]-benzonitrile Prepared from [2-amino-4-(2-chloro-phenylethynyl)-phenyl]-carbamic acid tert.-butyl ester (Example G4) (172 mg, 0.5 mmol) and 3-(2,2-dimethyl-6-oxo-6H-[1,3]dioxin-4-yl)-benzonitrile (Example J4) (230 mg, 0.75 mmol, 75% pure) according to the general procedure K. Obtained as a yellow solid (321 mg). This material was deprotected and cyclized by treatment with TFA in CH$_2$Cl$_2$ according to the general procedure M. Obtained as a light yellow solid (148 mg).

MS (EI) 395 (M$^+$) and 397 [(M+2)$^+$]; mp 239–240° C. (dec.).

Example 5

4-(3-Chloro-phenyl)-8-phenylethynyl-1,3-dihydro-benzo[b][1,4]diazepin-2-one

Prepared from (2-amino-4-phenylethynyl-phenyl)-carbamic acid tert.-butyl ester (Example G2) and 6-(3-chloro-phenyl)-2,2-dimethyl-[1,3]dioxin-4-one (Example J6) according to the general procedure K. The obtained material was deprotected and cyclized by treatment with TFA in CH$_2$Cl$_2$ according to the general procedure M. Obtained as an orange solid (155 mg).

MS (EI): 370 (M$^+$)

Example 6

3-[7-(4-Methoxy-phenyl)-4-oxo-4,5-dihydro-3H-benzo[b][1,4]diazepin-2-yl]-benzonitrile Prepared from {3-[3-(3-cyano-phenyl)-3-oxo-propionylamino]-4'-methoxy-biphenyl-4-yl}-carbamic acid tert.-butyl ester (Example K3) by treatment with TFA in $CH_2Cl_2$ according to the general procedure M. Obtained as a light yellow powder (122 mg).

MS (ISP) 368 $[(M+H)^+]$; mp 236–237° C. (dec.).

Example 7

3-(4-Oxo-7-thiophen-3-yl-4,5-dihydro-3H-benzo[b] [1,4]diazepin-2-yl)-benzonitrile Prepared from {2-[3-(3-cyano-phenyl)-3-oxo-propionylamino]-4-thiophen-3-yl-phenyl}-carbamic acid tert.-butyl ester (Example K4) by treatment with TFA in $CH_2Cl_2$ according to the general procedure M. Obtained as a beige solid (54 mg).

MS (EI) 343 $(M^+)$; mp 238–243° C. (dec.).

Example 8

3-(7-Furan-2-yl-4-oxo-4,5-dihydro-3H-benzo[b][1,4] diazepin-2-yl)-benzonitrile

Prepared from {2-[3-(3-cyano-phenyl)-3-oxo-propionylamino]-4-furan-2-yl-phenyl}-carbamic acid tert.-butyl ester (Example K5) by treatment with TFA in $CH_2Cl_2$ according to the general procedure M. Obtained as a brown powder (73 mg).

MS (EI) 327 $(M^+)$; mp 205–210° C. (dec.).

Example 9

3-[7-(4-Ethyl-phenyl)-4-oxo-4,5-dihydro-3H-benzo [b][1,4]diazepin-2-yl]-benzonitrile Prepared from (3-amino-4'-ethyl-biphenyl-4-yl)-carbamic acid tert.-butyl ester (Example G8) and 3-(2,2-dimethyl-6-oxo-6H-[1,3]dioxin-4-yl)-benzonitrile (Example J4) according to the general procedure K. The obtained material was deprotected and cyclized by treatment with TFA in $CH_2Cl_2$ according to the general procedure M. Obtained as a beige solid (67 mg).

MS (EI) 365 $(M^+)$; mp 225–229° C. (dec.).

Example 10

3-(4-Oxo-7-phenyl-4,5-dihydro-3H-benzo[b][1,4] diazepin-2-yl)-benzonitrile

Prepared from {3-[3-(3-cyano-phenyl)-3-oxo-propionylamino]-biphenyl-4-yl}-carbamic acid tert.-butyl ester (Example K6) (268 mg, 0.59 mmol) by treatment with TFA in $CH_2Cl_2$ according to the general procedure M. Obtained as a white solid (188 mg).

MS (EI) 337 $(M^+)$; mp 238–240° C. (dec.).

Example 11

4-(3-Iodo-phenyl)-8-phenylethynyl-1,3-dihydrobenzo[b][1,4]diazepin-2-one

Prepared from {2-[3-(3-iodo-phenyl)-3-oxo-propionylamino]-4-phenylethynyl-phenyl}-carbamic acid tert.-butyl ester (Example K7) (871 mg, 1.5 mmol) by treatment with TFA in $CH_2Cl_2$ according to the general procedure M. Obtained as a light yellow solid (542 mg).

MS (EI) 462 $(M^+)$; mp 227–229° C. (dec.).

Example 12

8-Phenylethynyl-4-pyridin-4-yl-1,3-dihydro-benzo [b][1,4]diazepin-2-one

Prepared from (2-amino-4-phenylethynyl-phenyl)-carbamic acid tert.-butyl ester (Example G2) and 2,2-dimethyl-6-pyridin-4-yl-[1,3]dioxin-4-one (Example J9) according to the general procedure K. The obtained material was deprotected and cyclized by treatment with TFA in $CH_2Cl_2$ according to the general procedure M. Obtained as a brown solid (50 mg).

MS (EI) 337 $(M^+)$; mp 198–200° C. (dec.).

Example 13

3-[7-(2-Methoxy-phenyl)-4-oxo-4,5-dihydro-3H-benzo[b][1,4]diazepin-2-yl]-benzonitrile Prepared from (3-amino-2'-methoxy-biphenyl-4-yl)-carbamic acid tert.-butyl ester (Example G10) and 3-(2,2-dimethyl-6-oxo-6H-[1,3]dioxin-4-yl)-benzonitrile (Example J4) according to the general procedure K. The obtained material was deprotected and cyclized by treatment with TFA in $CH_2Cl_2$ according to the general procedure M. Obtained as a light green powder (30 mg).

MS (EI) 367 $(M^+)$

Example 14

3-(7-Furan-3-yl-4-oxo-4,5-dihydro-3H-benzo[b][1,4] diazepin-2-yl)-benzonitrile

Prepared from {2-[3-(3-cyano-phenyl)-3-oxo-propionylamino]-4-furan-3-yl-phenyl}-carbamic acid tert.-butyl ester (Example K9) by treatment with TFA in $CH_2Cl_2$ according to the general procedure M. Obtained as a light yellow powder (73 mg).

MS (EI) 327 $(M^+)$; mp 228–233° C. (dec.).

Example 15

3-[7-(4-Chloro-phenyl)-4-oxo-4,5-dihydro-3H-benzo [b][1,4]diazepin-2-yl]-benzonitrile Prepared from (3-amino-4'-chloro-biphenyl-4-yl)-carbamic acid tert.-butyl ester (Example G12) and 3-(2,2-dimethyl-6-oxo-6H-[1,3]dioxin-4-yl)-benzonitrile (Example J4) according to the general procedure K. The obtained material was deprotected and cyclized by treatment with TFA in $CH_2Cl_2$ according to the general procedure M. Obtained as a yellow powder (79 mg).

MS (EI) 371 $(M^+)$; mp 244–250° C. (dec.).

Example 16

3-[7-(4-Chloro-phenylethynyl)-4-oxo-4,5-dihydro-3H-benzo[b][1,4]diazepin-2-yl]-benzonitrile Prepared from [2-amino-4-(4-chloro-phenylethynyl)-phenyl]-carbamic acid tert.-butyl ester (Example G13) (187 mg, 0.5 mmol) and 3-(2,2-dimethyl-6-oxo-6H-[1,3]dioxin-4-yl)-benzonitrile (Example J4) (184 mg, 0.6 mmol) according to the general procedure K. The obtained material (234 mg) was deprotected and cyclized by treatment with TFA in $CH_2Cl_2$ according to the general procedure M. Obtained as

Example 17

8-Phenyl-4-thiophen-2-yl-1,3-dihydro-benzo[b][1,4]diazepin-2-one

Prepared from (3-amino-biphenyl-4-yl)-carbamic acid tert.-butyl ester (Example G9) (69 mg, 0.243 mmol) and 2,2-dimethyl-6-thiophen-2-yl-[1,3]dioxin-4-one (Example J1) (54 mg, 0.257 mmol) according to the general procedure K. The obtained material was deprotected and cyclized by treatment with TFA in $CH_2Cl_2$ according to the general procedure M. Obtained as a brown solid (46 mg).

MS (ISP) 319 [(M+H)$^+$].

Example 18

8-Phenylethynyl-4-(3-trifluoromethyl-phenyl)-1,3-dihydro-benzo[b][1,4]diazepin-2-one Prepared from (2-amino-4-phenylethynyl-phenyl)-carbamic acid tert.-butyl ester (Example G2) and 2,2-dimethyl-6-(3-trifluoromethoxy-phenyl)-[1,3]dioxin-4-one (Example J8) according to the general procedure K. The obtained material was deprotected and cyclized by treatment with TFA in $CH_2Cl_2$ according to the general procedure M. Obtained as a yellow solid (157 mg).

MS (EI) 404 (M$^+$).

Example 19

4-(3-Chloro-phenyl)-8-phenyl-1,3-dihydro-benzo[b][1,4]diazepin-2-one

Prepared from (3-amino-biphenyl-4-yl)-carbamic acid tert.-butyl ester (Example G9) (284 mg, 1.0 mmol) and 6-(3-Chloro-phenyl)-2,2-dimethyl-[1,3]dioxin-4-one (Example J6) (358 mg, 1.2 mmol) according to the general procedure K. The obtained material (339 mg) was deprotected and cyclized by treatment with TFA in $CH_2Cl_2$ according to the general procedure M. Obtained as a yellow solid (188 mg).

MS (EI) 346 (M$^+$) and 348 [(M+2)$^+$]; mp 208° C. (dec.).

Example 20

3-(7-Naphthalen-1-yl-4-oxo-4,5-dihydro-3H-benzo[b][1,4]diazepin-2-yl)-benzonitrile Prepared from {2-[3-(3-cyano-phenyl)-3-oxo-propionylamino]-4-naphthalen-1-yl-phenyl}-carbamic acid tert.-butyl ester (Example K10) by treatment with TFA in $CH_2Cl_2$ according to the general procedure M. Obtained as a light yellow powder (41 mg).

MS (ISP) 388 [(M+H)$^+$]; mp 240–245° C. (dec.)

Example 21

3-(4-Oxo-7-thiazol-2-ylethynyl-4,5-dihydro-3H-benzo[b][1,4]diazepin-2-yl)-benzonitrile Prepared from {2-[3-(3-cyano-phenyl)-3-oxo-propionylamino]-4-thiazol-2-ylethynyl-phenyl}-carbamic acid tert.-butyl ester (Example K11) (119 mg, 0.24 mmol) by treatment with TFA in $CH_2Cl_2$ according to the general procedure M. Obtained as a yellow solid (36 mg).

MS (EI) 368 (M$^+$); mp 230° C. (dec.).

Example 22

3-(4-Oxo-7-p-tolyl-4,5-dihydro-3H-benzo[b][1,4]diazepin-2-yl)-benzonitrile

Prepared from (3-amino-4'-methyl-biphenyl-4-yl)-carbamic acid tert.-butyl ester (Example G16) and 3-(2,2-dimethyl-6-oxo-6H-[1,3]dioxin-4-yl)-benzonitrile (Example J4) according to the general procedure K. The obtained material was deprotected and cyclized by treatment with TFA in $CH_2Cl_2$ according to the general procedure M. Obtained as a white solid (76 mg).

MS (ISP) 352 [(M+H)$^+$]; mp 242–245° C. (dec.).

Example 23

4-(3-Chloro-thiophen-2-yl)-8-pyridin-2-yl-1,3-dihydro-benzo[b][1,4]diazepin-2-one Prepared from {2-[3-(3-chloro-thiophen-2-yl)-3-oxo-propionylamino]-4-pyridin-2-yl-phenyl}-carbamic acid tert.-butyl ester (Example K12) by treatment with TFA in $CH_2Cl_2$ according to the general procedure M. Obtained as a light brown powder (51 mg).

MS (EI) 353 (M$^+$); mp 220–225° C. (dec.).

Example 24

3-(4-Oxo-7-thiophen-2-yl-4,5-dihydro-3H-benzo[b][1,4]diazepin-2-yl)-benzonitrile Prepared from (2-amino-4-thiophen-2-yl-phenyl)-carbamic acid tert.-butyl ester (Example G18) and 3-(2,2-dimethyl-6-oxo-6H-[1,3]dioxin-4-yl)-benzonitrile (Example J4) according to the general procedure K. The obtained material was deprotected and cyclized by treatment with TFA in $CH_2Cl_2$ according to the general procedure M. Obtained as a light yellow solid (108 mg).

MS (EI) 343 (M$^+$); mp>250° C. (dec.).

Example 25

8-Iodo-4-thiophen-2-yl-1,3-dihydro-benzo[b][1,4]diazepin-2-one

Prepared from (2-amino-4-iodo-phenyl)-carbamic acid tert.-butyl ester (Example G1) and 2,2-dimethyl-6-thiophen-2-yl-[1,3]dioxin-4-one (Example J1) according to the general procedure K. The obtained material was deprotected and cyclized by treatment with TFA in $CH_2Cl_2$ according to the general procedure M. Obtained as a yellow solid (30 mg).

MS (EI) 368 (M$^+$); mp>260° C.

Example 26

3-(4-Oxo-7-pyridin-2-ylethynyl-4,5-dihydro-3H-benzo[b][1,4]diazepin-2-yl)-benzonitrile Prepared from (2-amino-4-pyridin-2-ylethynyl-phenyl)-carbamic acid tert.-butyl ester (Example G19) (124 mg, 0.4 mmol) and 3-(2,2-dimethyl-6-oxo-6H-[1,3]dioxin-4-yl)-benzonitrile (Example J4) (147 mg, 0.48 mmol) according to the general procedure K. The obtained material (199 mg)

Note: The first line of page 67 reads: "a light yellow powder (93 mg). MS (EI) 395 (M$^+$) and 397 [(M+2)$^+$]; mp 237–240° C. (dec.)."

was deprotected and cyclized by treatment with TFA in CH$_2$Cl$_2$ according to the general procedure M. Obtained as a yellow solid (124 mg).

MS (EI) 362 (M$^+$); mp 229–231° C. (dec.).

Example 27

4-(3-Methoxy-phenyl)-8-phenylethynyl-1,3-dihydro-benzo[b][1,4]diazepin-2-one

Prepared from (2-amino-4-phenylethynyl-phenyl)-carbamic acid tert.-butyl ester (Example G2) and 2,2-dimethyl-6-(3-methoxy-phenyl)-[1,3]dioxin-4-one (Example J11) according to the general procedure K. The obtained material was deprotected and cyclized by treatment with TFA in CH$_2$Cl$_2$ according to the general procedure M. Obtained as a light yellow solid (131 mg).

MS (EI) 366 (M$^+$).

Example 28

3-(4-Oxo-7-pyridin-2-yl-4,5-dihydro-3H-benzo[b][1,4]diazepin-2-yl)-benzonitrile

Prepared from {2-[3-(3-cyano-phenyl)-3-oxo-propionylamino]-4-pyridin-2-yl-phenyl}-carbamic acid tert.-butyl ester (Example K13) by treatment with TFA in CH$_2$Cl$_2$ according to the general procedure M. Obtained as a brown powder (29 mg).

MS (EI) 338 (M$^+$); mp 243–244° C. (dec.).

Example 29

8-Phenyl-4-thiophen-3-yl-1,3-dihydro-benzo[b][1,4]diazepin-2-one

Prepared from [3-(3-oxo-3-thiophen-3-yl-propionylamino)-biphenyl-4-yl]-carbamic acid tert.-butyl ester (Example K14) (110 mg, 0.25 mmol) by treatment with TFA in CH$_2$Cl$_2$ according to the general procedure M. Obtained as a light yellow solid (53 mg).

MS (EI) 318 (M$^+$); mp 233° C. (dec.).

Example 30

3-(4-Oxo-7-m-tolyl-4,5-dihydro-3H-benzo[b][1,4]diazepin-2-yl)-benzonitrile

Prepared from {3-[3-(3-cyano-phenyl)-3-oxo-propionylamino]-3'-methyl-biphenyl-4-yl}-carbamic acid tert.-butyl ester (Example K15) by treatment with TFA in CH$_2$Cl$_2$ according to the general procedure M. Obtained as a light yellow powder (145 mg).

MS (ISP) 352 [(M+H)$^+$]; mp 248–251° C. (dec.).

Example 31

3-[7-(3,4-Dichloro-phenyl)-4-oxo-4,5-dihydro-3H-benzo[b][1,4]diazepin-2-yl]-benzonitrile Prepared from (3-amino-3',4'-dichloro-biphenyl-4-yl)-carbamic acid tert.-butyl ester (Example G21) and 3-(2,2-dimethyl-6-oxo-6H-[1,3]dioxin-4-yl)-benzonitrile (Example J4) according to the general procedure K. The obtained material was deprotected and cyclized by treatment with TFA in CH$_2$Cl$_2$ according to the general procedure M. Obtained as a light yellow solid (150 mg).

MS (EI) 405 (Mt); mp 252–255° C. (dec.).

Example 32

8-Phenyl-4-(3-trifluoromethyl-phenyl)-1,3-dihydro-benzo[b][1,4]diazepin-2-one

Prepared from (3-amino-biphenyl-4-yl)-carbamic acid tert.-butyl ester (Example G9) (284 mg, 1.0 mmol) and 2,2-dimethyl-6-(3-trifluoromethyl-phenyl)-[1,3]dioxin-4-one (Example J5) (408 mg, 1.2 mmol) according to the general procedure K. The obtained material (392 mg) was deprotected and cyclized by treatment with TFA in CH$_2$Cl$_2$ according to the general procedure M. Obtained as a yellow solid (238 mg).

MS (EI) 380 (M$^+$); mp 210° C. (dec.).

Example 33

3-[7-(2-Chloro-phenyl)-4-oxo-4,5-dihydro-3H-benzo[b][1,4]diazepin-2-yl]-benzonitrile Prepared from (3-amino-2'-chloro-biphenyl-4-yl)-carbamic acid tert.-butyl ester (Example G22) and 3-(2,2-dimethyl-6-oxo-6H-[1,3]dioxin-4-yl)-benzonitrile (Example J4) according to the general procedure K. The obtained material was deprotected and cyclized by treatment with TFA in CH$_2$Cl$_2$ according to the general procedure M. Obtained as a white powder (43 mg).

MS (ISP) 372 [(M+H)$^+$]; mp 240–244° C. (dec.).

Example 34

4-(3-Chloro-thiophen-2-yl)-8-o-tolyl-1,3-dihydro-benzo[b][1,4]diazepin-2-one

Prepared from {3-[3-(3-chloro-thiophen-2-yl)-3-oxo-propionylamino]-2'-methyl-biphenyl-4-yl}-carbamic acid tert.-butyl ester (Example K16) by treatment with TFA in CH$_2$Cl$_2$ according to the general procedure M. Obtained as a light yellow powder (60 mg).

MS (ISP) 366 (M$^+$) and 368 [(M+2)$^+$]; mp 247–248° C. (dec.).

Example 35

8-Benzoyl-4-(3-chloro-phenyl)-1,3-dihydro-benzo[b][1,4]diazepin-2-one

Prepared from {4-benzoyl-2-[3-(3-chloro-phenyl)-3-oxo-propionylamino]-phenyl}-carbamic acid tert.-butyl ester (Example K17) (193 mg, 0.39 mmol) by treatment with TFA in CH$_2$Cl$_2$ according to the general procedure M. Obtained as a light yellow solid (93 mg).

MS (EI) 374 (M$^+$) and 376 [(M+2)$^+$]; mp 199–202° C. (dec.).

Example 36

3-(7-Benzoyl-4-oxo-4,5-dihydro-3H-benzo[b][1,4]diazepin-2-yl)-benzonitrile

Prepared from {4-benzoyl-2-[3-(3-cyano-phenyl)-3-oxo-propionylamino]-phenyl}-carbamic acid tert.-butyl ester (Example K18) (263 mg, 0.54 mmol) by treatment with TFA in CH₂Cl₂ according to the general procedure M. Obtained as an orange solid (77 mg).

MS (EI) 365 (M⁺); mp 207° C. (dec.).

Example 37

8-Benzoyl-4-thiophen-2-yl-1,3-dihydro-benzo[b][1,4]diazepin-2-one

Prepared from [4-benzoyl-2-(3-oxo-3-thiophen-2-yl-propionylamino)-phenyl]-carbamic acid tert.-butyl ester (Example K19) (54 mg, 0.12 mmol) by treatment with TFA in CH₂Cl₂ according to the general procedure M. Obtained as a yellow solid (8 mg).

MS (EI) 346 (M⁺).

Example 38

4-(3-Chloro-thiophen-2-yl)-8-phenyl-1,3-dihydro-benzo[b][1,4]diazepin-2-one

Prepared from {3-[3-(3-chloro-thiophen-2-yl)-3-oxo-propionylamino]-biphenyl-4-yl}-carbamic acid tert.-butyl ester (Example K20) (100 mg, 0.21 mmol) by treatment with TFA in CH₂Cl₂ according to the general procedure M. Obtained as a yellow solid (93 mg).

MS (EI) 352 (M⁺) and 354 [(M+2)⁺]; mp 228° C. (dec.).

Example 39

3-[7-(3-Methoxy-phenyl)-4-oxo-4,5-dihydro-3H-benzo[b][1,4]diazepin-2-yl]-benzonitrile Prepared from {3-[3-(3-cyano-phenyl)-3-oxo-propionylamino]-3'-methoxy-biphenyl-4-yl}-carbamic acid tert.-butyl ester (Example K21) by treatment with TFA in CH₂Cl₂ according to the general procedure M. Obtained as a light yellow powder (118 mg).

MS (ISP) 368 [(M+H)⁺]; mp 240–243° C. (dec.).

Example 40

3-(4-Oxo-7-pyridin-3-yl-4,5-dihydro-3H-benzo[b][1,4]diazepin-2-yl)-benzonitrile

Prepared from (2-amino-4-pyridin-3-yl-phenyl)-carbamic acid tert.-butyl ester (Example G26) and 3-(2,2-dimethyl-6-oxo-6H-[1,3]dioxin-4-yl)-benzonitrile (Example J4) according to the general procedure K. The obtained material was deprotected and cyclized by treatment with TFA in CH₂Cl₂ according to the general procedure M. Obtained as a beige powder (161 mg).

MS (EI) 338 (M⁺); mp 210–214° C. (dec.).

Example 41

8-(6-Oxo-1,6-dihydro-pyridin-3-yl)-4-thiophen-2-yl-1,3-dihydro-benzo[b][1,4]diazepin-2-one Prepared from [5-(6-oxo-1,6-dihydro-pyridin-3-yl)-2-(3-oxo-3-thiophen-2-yl-propionylamino)-phenyl]-carbamic acid tert.-butyl ester (Example K22) (127 mg, 0.28 mmol) by treatment with TFA in CH₂Cl₂ according to the general procedure M. Obtained as a yellow solid (57 mg).

MS (ISP) 336 [(M+H)⁺]; mp>250° C.

Example 42

8-(6-Benzyloxy-pyridin-3-yl)-4-(3-trifluoromethyl-phenyl)-1,3-dihydro-benzo[b][1,4]diazepin-2-one Prepared from {4-(6-benzyloxy-pyridin-3-yl)-2-[3-oxo-3-(3-trifluoromethyl-phenyl)-propionylamino]-phenyl}-carbamic acid tert.-butyl ester (Example K 23) (198 mg, 0.33 mmol) by treatment with TFA in CH₂Cl₂ according to the general procedure M. Obtained as a yellow solid (49 mg).

MS (ISP) 488 [(M+H)⁺]; mp 195° C. (dec.).

Example 43

3-[4-Oxo-7-(4-trifluoromethoxy-phenyl)-4,5-dihydro-3H-benzo[b][1,4]diazepin-2-yl]-benzonitrile Prepared from {3-[3-(3-cyano-phenyl)-3-oxo-propionylamino]-4'-trifluoromethoxy-biphenyl-4-yl}-carbamic acid tert.-butyl ester (Example K24) by treatment with TFA in CH₂Cl₂ according to the general procedure M. Obtained as a light yellow powder (23 mg).

MS (EI) 421 (M⁺); mp 237–241° C. (dec.).

Example 44

3-(4-Oxo-7-pyridin-4-yl-4,5-dihydro-3H-benzo[b][1,4]diazepin-2-yl)-benzonitrile

Prepared from (2-amino-4-pyridin-4-yl-phenyl)-carbamic acid tert.-butyl ester (Example G28) and 3-(2,2-dimethyl-6-oxo-6H-[1,3]dioxin-4-yl)-benzonitrile (Example J4) according to the general procedure K. The obtained material was deprotected and cyclized by treatment with TFA in CH₂Cl₂ according to the general procedure M. Obtained as a red-brown solid (25 mg).

MS (EI) 338 (M⁺); mp>200° C. (dec.).

Example 45

3-[7-(1-Benzenesulfonyl-1,2,3,6-tetrahydro-pyridin-4-yl)-4-oxo-4,5-dihydro-3H-benzo[b][1,4]diazepin-2-yl]-benzonitrile Prepared from 3-[4-oxo-7-(1,2,3,6-tetrahydro-pyridin-4-yl)-4,5-dihydro-3H-benzo[b][1,4]diazepin-2-yl]-benzonitrile [prepared from 4-{4-tert.-butoxycarbonylamino-3-[3-(3-cyano-phenyl)-3-oxo-propionylamino]-phenyl}-3,6-dihydro-2H-pyridine-1-carboxylic acid tert.-butyl ester (Example K25) (690 mg, 1.23 mmol) by treatment with TFA in CH₂Cl₂ according to the general procedure M. Obtained as a brown solid (309 mg)] (56 mg, 0.164 mmol) and benzenesulfonyl chloride (0.164 mmol) in THF (2 mL) at 23° C. Obtained as a brown solid (40 mg).

MS (ISP) 483 [(M+H)⁺]; mp 92–95° C. (dec.).

Example 46

3-[7-(1-Methanesulfonyl-1,2,3,6-tetrahydro-pyridin-4-yl)-4-oxo-4,5-dihydro-3H-benzo[b][1,4]diazepin-2-yl]-benzonitrile Prepared from 3-[4-oxo-7-(1,2,3,6-tetrahydro-pyridin-4-yl)-4,5-dihydro-3H-benzo[b][1,4]diazepin-2-yl]-benzonitrile [prepared from 4-{4-tert.-butoxycarbonylamino-3-[3-(3-cyano-phenyl)-3-oxo-propionylamino]-phenyl}-3,6-dihydro-2H-pyridine-1-carboxylic acid tert.-butyl ester (Example K25) (690 mg, 1.23 mmol) by treatment with TFA in CH$_2$Cl$_2$ according to the general procedure M. Obtained as a brown solid (309 mg)] (60 mg, 0.175 mmol), methanesulfonyl chloride (0.014 mL, 0.175 mmol) and Et$_3$N (0.025 mL, 0.175 mmol) in THF (3 mL) at 23° C. Obtained as an orange solid (35 mg).

MS (ISP) 421 [(M+H)$^+$]; mp 211–213° C. (dec.).

Example 47

3-[7-(1-Acetyl-1,2,3,6-tetrahydro-pyridin-4-yl)-4-oxo-4,5-dihydro-3H-benzo[b][1,4]diazepin-2-yl]-benzonitrile Prepared from 3-[4-oxo-7-(1,2,3,6-tetrahydro-pyridin-4-yl)-4,5-dihydro-3H-benzo[b][1,4]diazepin-2-yl]-benzonitrile [prepared from 4-{4-tert.-butoxycarbonylamino-3-[3-(3-cyano-phenyl)-3-oxo-propionylamino]-phenyl}-3,6-dihydro-2H-pyridine-1-carboxylic acid tert.-butyl ester (Example K25) (690 mg, 1.23 mmol) by treatment with TFA in CH$_2$Cl$_2$ according to the general procedure M. Obtained as a brown solid (309 mg)] (54 mg, 0.158 mmol) and Ac$_2$O (0.017 mL, 0.173 mmol) in THF (3 mL) at 23° C. Obtained as an orange solid (65 mg).

MS (EI) 384 (M$^+$); mp 220–222° C. (dec.).

Example 48

8-(6-Benzyloxy-pyridin-3-yl)-4-(3-chloro-thiophen-2-yl)-1,3-dihydro-benzo[b][1,4]diazepin-2-one Prepared from {4-(6-benzyloxy-pyridin-3-yl)-2-[3-(3-chloro-thiophen-2-yl)-3-oxo-propionylamino]-phenyl}-carbamic acid tert.-butyl ester (Example K26) (172 mg, 0.3 mmol) by treatment with TFA in CH$_2$Cl$_2$ according to the general procedure M. Obtained as a yellow solid (38 mg).

MS (ISP) 460 [(M+H)$^+$]; mp 213–215° C. (dec.).

Example 49

3-[7-(4-Methoxy-phenylethynyl)-4-oxo-4,5-dihydro-3H-benzo[b][1,4]diazepin-2-yl]-benzonitrile Prepared from 3-(7-iodo-4-oxo-4,5-dihydro-3H-benzo[b][1,4]diazepin-2-yl)-benzonitrile (Example 1) (290 mg, 0.75 mmol) and 4-methoxy-phenylacetylene (350 mg, 1.57 mmol) according to the general procedure F. Obtained as a light yellow solid (172 mg).

MS (EI) 391 (M$^+$); mp 234–235° C. (dec.).

Example 50

3-(4-Oxo-7-thiophen-2-ylethynyl-4,5-dihydro-3H-benzo[b][1,4]diazepin-2-yl)-benzonitrile Prepared from 3-(7-iodo-4-oxo-4,5-dihydro-3H-benzo[b][1,4]diazepin-2-yl)-benzonitrile (Example 50) (185 mg, 0.48 mmol) and 2-ethynylthiophene (78 mg, 0.72 mmol) [prepared from 2-thiophenecarboxaldehyde according to *J. Org. Chem.* 1982, 47, 2201–2204] according to the general procedure F. Obtained as a light yellow solid (146 mg).

MS (EI) 367 (M$^+$); mp 235–238° C. (dec.).

Example 51

3-[7-(2,3-Difluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-2',3'-difluoro-biphenyl-4-yl}-carbamic acid tert.-butyl ester (Example K8) (35 mg, 0.07 mmol) by treatment with TFA in CH$_2$Cl$_2$ according to the general procedure M. Obtained as a grey solid (23 mg).

MS (ISP) 374 [(M+H)$^+$]; mp 240° C.

Example 52

4-(3-Imidazol-1-yl-phenyl)-8-phenylethynyl-1,3-dihydro-benzo[b][1,4]diazepin-2-one Prepared from {2-[3-(3-imidazol-1-yl-phenyl)-3-oxo-propionylamino]-4-phenylethynyl-phenyl}-carbamic acid tert.-butyl ester (Example K27) (170 mg, 0.33 mmol) by treatment with TFA in CH$_2$Cl$_2$ according to the general procedure M. Obtained as a brown solid (64 mg).

MS (EI) 402 (M$^+$); mp 193–196° C.

Example 53

3-(7-Benzofuran-2-yl-4-oxo-4,5-dihydro-3H-benzo[b][1,4]diazepin-2-yl)-benzonitrile Prepared from {4-benzofuran-2-yl-2-[3-(3-cyano-phenyl)-3-oxo-propionylamino]-phenyl}-carbamic acid tert.-butyl ester (Example K28) (255 mg, 0.51 mmol) by treatment with TFA in CH$_2$Cl$_2$ according to the general procedure M. Obtained as a yellow solid (260 mg).

MS (EI) 377 (M$^+$); mp>250° C.

Example 54

3-(7-Biphenyl-4-yl-4-oxo-4,5-dihydro-3H-benzo[b][1,4]diazepin-2-yl)-benzonitrile Prepared from {3-[3-(3-cyano-phenyl)-3-oxo-propionylamino]-[1,1';4',1''] terphenyl-4-yl}-carbamic acid tert.-butyl ester (Example K29) (135 mg, 0.25 mmol) by treatment with TFA in CH$_2$Cl$_2$ according to the general procedure M. Obtained as a light yellow solid (100 mg).

MS (EI) 413 (M$^+$); mp 251–253° C.

Example 55

3-[4-Oxo-7-(4-trifluoromethoxy-phenylethynyl)-4,5-dihydro-3H-benzo[b][1,4]diazepin-2-yl]-benzonitrile Prepared from [2-[3-(3-cyano-phenyl)-3-oxo-propionylamino]-4-(4-trifluoromethoxy-phenylethynyl)-phenyl]-carbamic acid tert.-butyl ester (Example K30) (170 mg, 0.3 mmol) by treatment with TFA in CH$_2$Cl$_2$ according to the general procedure M. Obtained as a beige solid (112 mg).

MS (EI) 445 (M$^+$); mp 239–241° C.

Example 56

4-(3-Nitro-phenyl)-8-phenylethynyl-1,3-dihydro-benzo[b][1,4]diazepin-2-one

Prepared from {2-[3-(3-nitro-phenyl)-3-oxo-propionylamino]-4-phenylethynyl-phenyl}-carbamic acid tert.-butyl ester (Example K31) (970 mg, 1.94 mmol) by treatment with TFA in $CH_2Cl_2$ according to the general procedure M. Obtained as a light yellow solid (631 mg).

MS (EI) 381 ($M^+$); mp 228–229° C.

Example 57

3-[7-(4-Fluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-4'-fluoro-biphenyl-4-yl}-carbamic acid tert.-butyl ester (Example K32) by treatment with TFA in $CH_2Cl_2$ according to the general procedure M. Obtained as an orange solid (141 mg).

MS (EI) 355 ($M^+$).

Example 58

8-(4-Fluoro-phenylethynyl)-4-(3-imidazol-1-yl-phenyl)-1,3-dihydro-benzo[b][1,4]diazepin-2-one Prepared from {4-(4-fluoro-phenylethynyl)-2-[3-(3-imidazol-1-yl-phenyl)-3-oxo-propionylamino]-phenyl}-carbamic acid tert.-butyl ester (Example K33) by treatment with TFA in $CH_2Cl_2$ according to the general procedure M. Obtained as a beige solid (89 mg).

MS (EI) 420 ($M^+$); mp 216–218° C.

Example 59

4-(3-Imidazol-1-yl-phenyl)-8-phenyl-1,3-dihydro-benzo[b][1,4]diazepin-2-one

Prepared from {3-[3-(3-imidazol-1-yl-phenyl)-3-oxo-propionylamino]-biphenyl-4-yl}-carbamic acid tert.-butyl ester (Example K34) by treatment with TFA in $CH_2Cl_2$ according to the general procedure M. Obtained as a light yellow solid (125 mg).

MS (EI) 378 ($M^+$); mp 201–205° C.

Example 60

8-(4-Fluoro-phenyl)-4-(3-imidazol-1-yl-phenyl)-1,3-dihydro-benzo[b][1,4]diazepin-2-one Prepared from {4'-fluoro-3-[3-(3-imidazol-1-yl-phenyl)-3-oxo-propionylamino]-biphenyl-4-yl}-carbamic acid tert.-butyl ester (Example K35) by treatment with TFA in $CH_2Cl_2$ according to the general procedure M. Obtained as an orange solid (261 mg).

MS (EI) 396 ($M^+$).

Example 61

4-(3-Imidazol-1-yl-phenyl)-8-(4-methoxy-phenyl)-1,3-dihydro-benzo[b][1,4]diazepin-2-one Prepared from (3-amino-4'-methoxy-biphenyl-4-yl)-carbamic acid tert.-butyl ester (Example K36) by treatment with TFA in $CH_2Cl_2$ according to the general procedure M. Obtained as a light yellow solid (100 mg). MS (EI) 408 ($M^+$); mp 207–208° C.

Example 62

8-(4-Fluoro-phenylethynyl)-4-(3-[1,2,4]triazol-1-yl-phenyl)-1,3-dihydro-benzo[b][1,4]diazepin-2-one Prepared from {4-(4-fluoro-phenylethynyl)-2-[3-oxo-3-(3-[1,2,4]triazol-1-yl-phenyl)-propionylamino]-phenyl}-carbamic acid tert.-butyl ester (Example K37) by treatment with TFA in $CH_2Cl_2$ according to the general procedure M. Obtained as a yellow solid (156 mg).

MS (EI) 421 ($M^+$); mp 217–218° C.

Example 63

8-(2-Fluoro-phenylethynyl)-4-(3-imidazol-1-yl-phenyl)-1,3-dihydro-benzo[b][1,4]diazepin-2-one Prepared from {4-(2-fluoro-phenylethynyl)-2-[3-(3-imidazol-1-yl-phenyl)-3-oxo-propionylamino]-phenyl}-carbamic acid tert.-butyl ester (Example K38) by treatment with TFA in $CH_2Cl_2$ according to the general procedure M. Obtained as a yellow solid (99 mg).

MS (EI) 420 ($M^+$); mp 201–203° C.

Example 64

8-(4-Fluoro-phenyl)-4-(3-[1,2,4]triazol-1-yl-phenyl)-1,3-dihydro-benzo[b][1,4]diazepin-2-one Prepared from {4'-fluoro-3-[3-oxo-3-(3-[1,2,4]triazol-1-yl-phenyl)-propionylamino]-biphenyl-4-yl}-carbamic acid tert.-butyl ester (Example K39) by treatment with TFA in $CH_2Cl_2$ according to the general procedure M. Obtained as a light yellow solid (115 mg).

MS (EI) 397 ($M^+$); mp 241–245° C.

Example 65

3-[7-(4-Cyano-phenyl)-4-oxo-4,5-dihydro-3H-benzo[b][1,4]diazepin-2-yl]-benzonitrile Prepared from {4'-cyano-3-[3-(3-cyano-phenyl)-3-oxo-propionylamino]-biphenyl-4-yl}-carbamic acid tert.-butyl ester (Example K40) by treatment with TFA in $CH_2Cl_2$ according to the general procedure M. Obtained as a light yellow solid (102 mg).

MS (EI) 362 ($M^+$); mp 240° C. (dec.).

Example 66

4-[2-(3-Imidazol-1-yl-phenyl)-4-oxo-4,5-dihydro-3H-benzo[b][1,4]diazepin-7-yl]-benzonitrile Prepared from {4'-cyano-3-[3-(3-imidazol-1-yl-phenyl)-3-oxo-propionylamino]-biphenyl-4-yl}-carbamic acid tert-butyl ester (Example K41) by treatment with TFA in $CH_2Cl_2$ according to the general procedure M. Obtained as a light yellow solid (128 mg).

MS (EI) 403 ($M^+$); mp 209–213° C. (dec.).

Example 67

8-(4-Fluoro-phenyl)-4-(3-nitro-phenyl)-1,3-dihydro-benzo[b][1,4]diazepin-2-one

Prepared from {4'-fluoro-3-[3-(3-nitro-phenyl)-3-oxo-propionylamino]-biphenyl-4-yl}-carbamic acid tert.-butyl

Example 68

8-(4-Fluoro-phenylethynyl)-4-(2-imidazol-1-yl-pyridin-4-yl)-1,3-dihydro-benzo[b][1,4]diazepin-2-one Prepared from {4-(4-fluoro-phenylethynyl)-2-[3-(2-imidazol-1-yl-pyridin-4-yl)-3-oxo-propionylamino]-phenyl}-carbamic acid tert.-butyl ester (Example K43) by treatment with TFA in CH$_2$Cl$_2$ according to the general procedure M. Obtained as a light brown solid (189 mg).

MS (ISP) 422 [(M+H)$^+$]; mp 206° C. (dec.).

Example 69

8-(4-Fluoro-phenyl)-4-(2-imidazol-1-yl-pyridin-4-yl)-1,3-dihydro-benzo[b][1,4]diazepin-2-one Prepared from {4'-fluoro-3-[3-(2-imidazol-1-yl-pyridin-4-yl)-3-oxo-propionylamino]-biphenyl-4-yl}-carbamic acid tert.-butyl ester (Example K43) by treatment with TFA in CH$_2$Cl$_2$ according to the general procedure M. Obtained as a light brown solid (209 mg).

MS (ISP) 398 [(M+H)$^+$]; mp 213° C. (dec.).

Example 70

4-(3-Amino-phenyl)-8-(4-fluoro-phenyl)-1,3-dihydro-benzo[b][1,4]diazepin-2-one

Prepared from 8-(4-fluoro-phenyl)-4-(3-nitro-phenyl)-1,3-dihydro-benzo[b][1,4]diazepin-2-one (Example 67) by catalytic hydrogenation with Raney-Ni according to the general procedure G (method a). Obtained as a light yellow solid (16 mg).

MS (ISP) 346 [(M+H)$^+$]; mp 210–217° C. (dec.).

Example 71

8-(2-Fluoro-phenyl)-4-(3-imidazol-1-yl-phenyl)-1,3-dihydro-benzo[b][1,4]diazepin-2-one Prepared from {2'-fluoro-3-[3-(3-imidazol-1-yl-phenyl)-3-oxo-propionylamino]-biphenyl-4-yl}-carbamic acid tert.-butyl ester (Example K45) by treatment with TFA in CH$_2$Cl$_2$ according to the general procedure M. Obtained as a light yellow solid (176 mg).

MS (ISP) 397 [(M+H)$^+$]; mp 179–182° C.

Example 72

N-{3-[7-(4-Fluoro-phenyl)-4-oxo-4,5-dihydro-3H-benzo[b][1,4]diazepin-2-yl]-phenyl}-acetamide Prepared from 4-(3-amino-phenyl)-8-(4-fluoro-phenyl)-1,3-dihydro-benzo[b][1,4]diazepin-2-one (Example 70) by treatment with Ac$_2$O in HOAc at 80° C. Obtained as a light yellow solid (9 mg).

MS (EI) 387 (M$^+$).

Example 73

N-{3-[7-(4-Fluoro-phenyl)-4-oxo-4,5-dihydro-3H-benzo[b][1,4]diazepin-2-yl]-phenyl}-methanesulfonamide Prepared from 4-(3-amino-phenyl)-8-(4-fluoro-phenyl)-1,3-dihydro-benzo[b][1,4]diazepin-2-one (Example 70) by treatment with methanesulfonyl chloride and Et$_3$N in THF at 23° C. Obtained as a light yellow solid (24 mg).

MS (ISP) 424 [(M+H)$^+$]; mp 232–235° C.

Example 74

8-(6-Benzyloxy-pyridin-3-yl)-4-(3-imidazol-1-yl-phenyl)-1,3-dihydro-benzo[b][1,4]diazepin-2-one Prepared from {4-(6-benzyloxy-pyridin-3-yl)-2-[3-(3-imidazol-1-yl-phenyl)-3-oxo-propionylamino]-phenyl}-carbamic acid tert.-butyl ester (Example K46) by treatment with TFA in CH$_2$Cl$_2$ according to the general procedure M. Obtained as a light yellow solid (75 mg).

MS (ISP) 486 [(M+H)$^+$]; mp 225–231° C.

Example 75

4-(3-Imidazol-1-yl-phenyl)-8-(6-oxo-1,6-dihydro-pyridin-3-yl)-1,3-dihydro-benzo[b][1,4]diazepin-2-one Prepared from 8-(6-benzyloxy-pyridin-3-yl)-4-(3-imidazol-1-yl-phenyl)-1,3-dihydro-benzo[b][1,4]diazepin-2-one (Example 74) by catalytic hydrogenation with Raney-Ni according to the general procedure G (method a). Obtained as a light yellow solid (17 mg).

MS (ISP) 396 [(M+H)$^+$].

Example 76

8-(4-Fluoro-phenyl)-4-[3-(4-methyl-imidazol-1-yl)-phenyl]-1,3-dihydro-benzo[b][1,4]diazepin-2-one Prepared from (4'-fluoro-3-{3-[3-(4-methyl-imidazol-1-yl)-phenyl]-3-oxo-propionylamino}-biphenyl-4-yl)-carbamic acid tert.-butyl ester (Example K47) by treatment with TFA in CH$_2$Cl$_2$ according to the general procedure M. Obtained as a light yellow solid (196 mg).

MS (EI) 410 (M$^+$); mp 215° C.

Example 77

8-(2-Fluoro-phenyl)-4-(2-imidazol-1-yl-pyridin-4-yl)-1,3-dihydro-benzo[b][1,4]diazepin-2-one Prepared from {2'-fluoro-3-[3-(2-imidazol-1-yl-pyridin-4-yl)-3-oxo-propionylamino]-biphenyl-4-yl}-carbamic acid tert.-butyl ester (Example K48) by treatment with TFA in CH$_2$Cl$_2$ according to the general procedure M. Obtained as a light brown solid (32 mg).

MS (EI) 397 (M$^+$).

Example 78

8-(4-Fluoro-phenylethynyl)-4-[3-(4-methyl-imidazol-1-yl)-phenyl]-1,3-dihydro-benzo[b][1,4]diazepin-2-one Prepared from (4-(4-fluoro-phenylethynyl)-2-{3-[3-(4-methyl-imidazol-1-yl)-phenyl]-3-oxo-propionylamino}-phenyl)-carbamic acid tert.-butyl ester (Example K49) by treatment with TFA in CH$_2$Cl$_2$ according to the general procedure M. Obtained as a light yellow solid (122 mg).
MS (EI) 434 (M$^+$); mp 210° C.

Example 79

8-(4-Fluoro-2-methyl-phenyl)-4-(3-imidazol-1-yl-phenyl)-1,3-dihydro-benzo[b][1,4]diazepin-2-one Prepared from {4'-fluoro-3-[3-(3-imidazol-1-yl-phenyl)-3-oxo-propionylamino]-2'-methyl-biphenyl-4-yl}-carbamic acid tert.-butyl ester (Example K50) by treatment with TFA in CH$_2$Cl$_2$ according to the general procedure M. Obtained as a beige solid (82 mg).
MS (EI) 410 (M$^+$); mp 170–172° C.

Example 80

8-(4-Fluoro-2-hydroxy-phenyl)-4-(3-imidazol-1-yl-phenyl)-1,3-dihydro-benzo[b][1,4]diazepin-2-one Prepared from {4'-fluoro-3-[3-(3-imidazol-1-yl-phenyl)-3-oxo-propionylamino]-2'-methoxymethoxy-biphenyl-4-yl}-carbamic acid tert.-butyl ester (Example K51) by treatment with TFA in CH$_2$Cl$_2$ according to the general procedure M. Obtained as a light yellow solid (13 mg).
MS (ISP) 413 [(M+H)$^+$]; mp 220° C.

Example 81

8-(2-Fluoro-phenyl)-4-[3-(2-methyl-imidazol-1-yl)-phenyl]-1,3-dihydro-benzo[b][1,4]diazepin-2-one Prepared from (2'-fluoro-3-{3-[3-(2-methyl-imidazol-1-yl)-phenyl]-3-oxo-propionylamino}-biphenyl-4-yl)-carbamic acid tert.-butyl ester (Example K52) by treatment with TFA in CH$_2$Cl$_2$ according to the general procedure M. Obtained as a yellow solid (174 mg).
MS (ISP) 411 [(M+H)$^+$]; mp 187° C.

Example 82

8-(4-Fluoro-phenyl)-4-[3-(2-methyl-imidazol-1-yl)-phenyl]-1,3-dihydro-benzo[b][1,4]diazepin-2-one Prepared from (4'-fluoro-3-{3-[3-(2-methyl-imidazol-1-yl)-phenyl]-3-oxo-propionylamino}-biphenyl-4-yl)-carbamic acid tert.-butyl ester (Example K53) by treatment with TFA in CH$_2$Cl$_2$ according to the general procedure M. Obtained as a yellow solid (178 mg).
MS (ISP) 411 [(M+H)$^+$]; mp 227° C.

Example 83

2-[7-(4-Fluoro-phenyl)-4-oxo-4,5-dihydro-1H-benzo[b][1,4]diazepin-2-yl]-thiophene-3-carbonitrile Prepared from {3-[3-(3-cyano-thiophen-2-yl)-3-oxo-propionylamino]-4'-fluoro-biphenyl-4-yl}-carbamic acid tert.-butyl ester (Example K54) by treatment with TFA in CH$_2$Cl$_2$ according to the general procedure M. Obtained as an orange solid (209 mg).
MS (EI) 361 (M$^+$); mp 239–240° C.

Example 84

2-[7-(2-Fluoro-phenyl)-4-oxo-4,5-dihydro-1H-benzo[b][1,4]diazepin-2-yl]-thiophene-3-carbonitrile Prepared from {3-[3-(3-cyano-thiophen-2-yl)-3-oxo-propionylamino]-2'-fluoro-biphenyl-4-yl}-carbamic acid tert.-butyl ester (Example K55) by treatment with TFA in CH$_2$Cl$_2$ according to the general procedure M. Obtained as a yellow solid (258 mg).
MS (EI) 361 (M$^+$); mp 238–240° C.

Example 85

8-(4-Fluoro-phenyl)-4-(3-tetrazol-1-yl-phenyl)-1,3-dihydro-benzo[b][1,4]diazepin-2-one Prepared from {4'-fluoro-3-[3-oxo-3-(3-tetrazol-1-yl-phenyl)-propionylamino]-biphenyl-4-yl}-carbamic acid tert.-butyl ester (Example K56) by treatment with TFA in CH$_2$Cl$_2$ according to the general procedure M. Obtained as a light yellow solid (54 mg).
MS (EI) 398 (M$^+$).

Example 86

3-[7-(2-Fluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-2'-fluoro-biphenyl-4-yl}-carbamic acid tert.-butyl ester (Example K57) by treatment with TFA in CH$_2$Cl$_2$ according to the general procedure M. Obtained as a light yellow solid (128 mg).
MS (EI) 355 (M$^+$).

Example 87

8-(4-Fluoro-phenylethynyl)-4-(3-tetrazol-1-yl-phenyl)-1,3-dihydro-benzo[b][1,4]diazepin-2-one Prepared from [2-amino-4-(4-fluoro-phenylethynyl)-phenyl]-carbamic acid tert.-butyl ester (Example G33) and 3-oxo-3-(3-tetrazol-1-yl-phenyl)-propionic acid ethyl ester (Example H15) according to the general procedure K. The obtained material was deprotected and cyclized by treatment with TFA in CH$_2$Cl$_2$ according to the general procedure M. Obtained as a beige powder (5.5 mg).
MS (EI) 422 (M$^+$).

Example 88

8-(2-Fluoro-phenyl)-4-(3-tetrazol-1-yl-phenyl)-1,3-dihydro-benzo[b][1,4]diazepin-2-one Prepared from {2'-fluoro-3-[3-oxo-3-(3-tetrazol-1-yl-phenyl)-propionylamino]-biphenyl-4-yl}-carbamic acid tert.-butyl ester (Example K58) by treatment with TFA in CH$_2$Cl$_2$ according to the general procedure M. Obtained as a light yellow solid (31 mg).
MS (EI) 398 (M$^+$); mp 179–180° C.

Example 89

4-[3-(2,4-Dimethyl-imidazol-1-yl)-phenyl]-8-(4-fluoro-phenyl)-1,3-dihydro-benzo[b][1,4]diazepin-2-one Prepared from (3-{3-[3-(2,4-dimethyl-imidazol-1-yl)-phenyl]-3-oxo-propionylamino}-4'-fluoro-biphenyl-4-yl)-carbamic acid tert.-butyl ester (Example K59) by treatment with TFA in CH$_2$Cl$_2$ according to the general procedure M. Obtained as a yellow solid (54 mg).
MS (EI) 424 (M$^+$); mp 188° C.

Example 90

4-[3-(2,4-Dimethyl-imidazol-1-yl)-phenyl]-8-phenylethynyl-1,3-dihydro-benzo[b][1,4]diazepin-2-one Prepared from (2-{3-[3-(2,4-dimethyl-imidazol-1-yl)-phenyl]-3-oxo-propionylamino}-4-phenylethynyl-phenyl)-carbamic acid tert.-butyl ester (Example K60) by treatment with TFA in CH$_2$Cl$_2$ according to the general procedure M. Obtained as a yellow solid (57 mg). MS (EI) 430 (M$^+$); mp 134° C. (dec.).

Example 91

4-(3-Chloro-thiophen-2-yl)-8-(4-fluoro-phenyl)-1,3-dihydro-benzo[b][1,4]diazepin-2-one Prepared from {3-[3-(3-chloro-thiophen-2-yl)-3-oxo-propionylamino]-4'-fluoro-biphenyl-4-yl}-carbamic acid tert.-butyl ester (Example K61) by treatment with TFA in CH$_2$Cl$_2$ according to the general procedure M. Obtained as a yellow solid (232 mg).
MS (EI) 370 (M$^+$); mp 255–256° C.

Example 92

3-[7-(2-Fluoro-6-methoxy-phenyl)-4-oxo-4,5-dihydro-3H-benzo[b][1,4]diazepin-2-yl]-benzonitrile Prepared from (3-amino-2'-fluoro-6'-methoxy-biphenyl-4-yl)-carbamic acid tert.-butyl ester (Example G44) and 3-(2,2-dimethyl-6-oxo-6H-[1,3]dioxin-4-yl)-benzonitrile (Example J4) according to the general procedure K. The obtained material was deprotected and cyclized by treatment with TFA in CH$_2$Cl$_2$ according to the general procedure M. Obtained as a white solid (47 mg).
MS (EI) 385 (M$^+$).

Example 93

8-(2-Fluoro-phenyl)-4-(3-nitro-phenyl)-1,3-dihydro-benzo[b][1,4]diazepin-2-one

Prepared from {2'-fluoro-3-[3-(3-nitro-phenyl)-3-oxo-propionylamino]-biphenyl-4-yl}-carbamic acid tert.-butyl ester (Example K62) by treatment with TFA in CH$_2$Cl$_2$ according to the general procedure M. Obtained as a light yellow solid (62 mg).
MS (EI) 375 (M$^+$).

Example 94

4-[7-(4-Fluoro-phenyl)-4-oxo-4,5-dihydro-3H-benzo[b][1,4]diazepin-2-yl]-pyridine-2-carbonitrile Prepared from {3-[3-(2-cyano-pyridin-4-yl)-3-oxo-propionylamino]-4'-fluoro-biphenyl-4-yl}-carbamic acid tert.-butyl ester (Example K63) by treatment with TFA in CH$_2$Cl$_2$ according to the general procedure M. Obtained as an orange solid (23 mg).
MS (EI) 356 (M$^+$).

Example 95

4-[7-(2-Fluoro-phenyl)-4-oxo-4,5-dihydro-3H-benzo[b][1,4]diazepin-2-yl]-pyridine-2-carbonitrile Prepared from {3-[3-(2-cyano-pyridin-4-yl)-3-oxo-propionylamino]-2'-fluoro-biphenyl-4-yl}-carbamic acid tert.-butyl ester (Example K64) by treatment with TFA in CH$_2$Cl$_2$ according to the general procedure M. Obtained as a green solid (40 mg).
MS (EI) 356 (M$^+$).

Example 96

3-[7-(3-Fluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-3'-fluoro-biphenyl-4-yl}-carbamic acid tert.-butyl ester (Example K65) by treatment with TFA in CH$_2$Cl$_2$ according to the general procedure M. Obtained as a yellow solid (57 mg).
MS (EI) 355 (M$^+$); mp 232–235° C.

Example 97

8-(3-Fluoro-phenyl)-4-(3-imidazol-1-yl-phenyl)-1,3-dihydro-benzo[b][1,4]diazepin-2-one Prepared from {3'-fluoro-3-[3-(3-imidazol-1-yl-phenyl)-3-oxo-propionylamino]-biphenyl-4-yl}-carbamic acid tert.-butyl ester (Example K66) by treatment with TFA in CH$_2$Cl$_2$ according to the general procedure M. Obtained as a yellow solid (69 mg).
MS (EI) 396 (M$^+$); mp 200–201° C.

Example 98

4-(4-Oxo-7-phenylethynyl-4,5-dihydro-3H-benzo[b][1,4]diazepin-2-yl)-pyridine-2-carbonitrile Prepared from {2-[3-(2-cyano-pyridin-4-yl)-3-oxo-propionylamino]-4-phenylethynyl-phenyl}-carbamic acid tert.-butyl ester (Example K67) by treatment with TFA in CH$_2$Cl$_2$ according to the general procedure M. Obtained as a yellow solid (10 mg).
MS (EI) 362 (M$^+$).

Example 99

8-(2-Fluoro-phenyl)-4-(3-[1,2,4]triazol-4-yl-phenyl)-1,3-dihydro-benzo[b][1,4]diazepin-2-one Prepared from {2'-fluoro-3-[3-oxo-3-(3-[1,2,4]triazol-4-yl-phenyl)-propionylamino]-biphenyl-4-yl}-carbamic acid tert.-butyl ester (Example K68) by treatment with TFA in CH$_2$Cl$_2$ according to the general procedure M. Obtained as a light yellow solid (79 mg).

MS (EI) 397 (M$^+$); mp 198° C.

Example 100

5-[7-(2-Fluoro-phenyl)-4-oxo-4,5-dihydro-3H-benzo[b][1,4]diazepin-2-yl]-thiophene-2-carbonitrile Prepared from {3-[3-(5-cyano-thiophen-2-yl)-3-oxo-propionylamino]-2'-fluoro-biphenyl-4-yl}-carbamic acid tert.-butyl ester (Example K69) by treatment with TFA in CH$_2$Cl$_2$ according to the general procedure M. Obtained as a yellow solid (263 mg).

MS (EI) 361 (M$^+$); mp>250° C.

Example 101

4-[3-(2,4-Dimethyl-imidazol-1-yl)-phenyl]-8-(2-fluoro-phenyl)-1,3-dihydro-benzo[b][1,4]diazepin-2-one Prepared from (3-{3-[3-(2,4-dimethyl-imidazol-1-yl)-phenyl]-3-oxo-propionylamino}-2'-fluoro-biphenyl-4-yl)-carbamic acid tert.-butyl ester (Example K70) by treatment with TFA in CH$_2$Cl$_2$ according to the general procedure M. Obtained as a yellow solid (92 mg).

MS (EI) 424 (M$^+$); mp 92° C.

Example 102

8-(2-Fluoro-phenyl)-4-[3-(2-methoxymethylsulfanyl-imidazol-1-yl)-phenyl]-1,3-dihydro-benzo[b][1,4]diazepin-2-one Prepared from (2'-fluoro-3-{3-[3-(2-methoxymethylsulfanyl-imidazol-1-yl)-phenyl]-3-oxo-propionylamino}-biphenyl-4-yl)-carbamic acid tert.-butyl ester (Example K71) by treatment with TFA in CH$_2$Cl$_2$ according to the general procedure M. Obtained as a light yellow solid (100 mg).

MS (EI) 472 (M$^+$); mp 189–190° C.

Example 103

4-Fluoro-3-[7-(2-fluoro-phenyl)-4-oxo-4,5-dihydro-3H-benzo[b][1,4]diazepin-2-yl]-benzonitrile Prepared from {3-[3-(5-cyano-2-fluoro-phenyl)-3-oxo-propionylamino]-2'-fluoro-biphenyl-4-yl}-carbamic acid tert.-butyl ester (Example K72) by treatment with TFA in CH$_2$Cl$_2$ according to the general procedure M. Obtained as a yellow solid (92 mg).

MS (EI) 373 (M$^+$); mp 239° C.

Example 104

4-[7-(2,4-Difluoro-phenyl)-4-oxo-4,5-dihydro-3H-benzo[b][1,4]diazepin-2-yl]-pyridine-2-carbonitrile Prepared from {3-[3-(2-cyano-pyridin-4-yl)-3-oxo-propionylamino]-2',4'-difluoro-biphenyl-4-yl}-carbamic acid tert.-butyl ester (Example K73) by treatment with TFA in CH$_2$Cl$_2$ according to the general procedure M. Obtained as a light yellow solid (24 mg).

MS (ISP) 375 [(M+H)$^+$]; mp 250–253° C.

Example 105

4-(7-Isopropyl-4-oxo-4,5-dihydro-3H-benzo[b][1,4]diazepin-2-yl)-pyridine-2-carbonitrile Prepared from {2-[3-(2-cyano-pyridin-4-yl)-3-oxo-propionylamino]-4-isopropyl-phenyl}-carbamic acid tert.-butyl ester (Example K74) by treatment with TFA in CH$_2$Cl$_2$ according to the general procedure M. Obtained as a yellow solid (33 mg).

MS (ISP) 305 [(M+H)$^+$]; mp 173–178° C.

Example 106

8-(2-Fluoro-phenyl)-4-[2-(4-methyl-imidazol-1-yl)-thiazol-4-yl]-1,3-dihydro-benzo[b][1,4]diazepin-2-one Prepared from (2'-fluoro-3-{3-[2-(4-methyl-imidazol-1-yl)-thiazol-4-yl]-3-oxo-propionylamino}-biphenyl-4-yl)-carbamic acid tert.-butyl ester (Example K75) by treatment with TFA in CH$_2$Cl$_2$ according to the general procedure M. Obtained as a yellow solid (75 mg).

MS (ISP) 418 [(M+H)$^+$]; mp 229° C.

Example 107

8-(4-Fluoro-phenyl)-4-[2-(4-methyl-imidazol-1-yl)-thiazol-4-yl]-1,3-dihydro-benzo[b][1,4]diazepin-2-one Prepared from (4'-fluoro-3-{3-[2-(4-methyl-imidazol-1-yl)-thiazol-4-yl]-3-oxo-propionylamino}-biphenyl-4-yl)-carbamic acid tert.-butyl ester (Example K76) by treatment with TFA in CH$_2$Cl$_2$ according to the general procedure M. Obtained as a yellow solid (101 mg).

MS (ISP) 418 [(M+H)$^+$]; mp 229° C.

Example 108

3-(4-Oxo-7-phenethyl-4,5-dihydro-3H-benzo[b][1,4]diazepin-2-yl)-benzonitrile

Prepared from 3-(4-oxo-7-phenylethynyl-4,5-dihydro-3H-benzo[b][1,4]diazepin-2-yl)-benzonitrile (Example 2) by catalytic hydrogenation with Pd/C according to the general procedure G (method a). Obtained as a light yellow solid (156 mg).

MS (EI) 365 (M$^+$); mp 212–214° C.

Example 109

3-(4-Oxo-7-styryl-4,5-dihydro-3H-benzo[b][1,4]diazepin-2-yl)-benzonitrile

Prepared from 3-(4-oxo-7-phenylethynyl-4,5-dihydro-3H-benzo[b][1,4]diazepin-2-yl)-benzonitrile (Example 2) by catalytic hydrogenation with Lindlar-catalyst in the presence of 10 eq. cyclohexene according to the general procedure G (method a). Obtained as a light yellow solid (159 mg).

MS (EI) 363 (M$^+$); mp 185–188° C.

Example 110

8-(2-Fluoro-phenyl)-4-(3-[1,2,3]triazol-1-yl-phenyl)-1,3-dihydro-benzo[b][1,4]diazepin-2-one Prepared from {2'-fluoro-3-[3-oxo-3-(3-[1,2,3]triazol-1-yl-phenyl)-propionylamino]-biphenyl-4-yl}-carbamic acid tert.-butyl ester (Example K77) by treatment with TFA in $CH_2Cl_2$ according to the general procedure M. Obtained as a light yellow solid (100 mg).

MS (EI) 397 (M$^+$); mp 209–212° C.

Example 111

3-(7-Cyclopropyl-4-oxo-4,5-dihydro-3H-benzo[b][1,4]diazepin-2-yl)-benzonitrile

Prepared from {2-[3-(3-cyano-phenyl)-3-oxo-propionylamino]-4-cyclopropyl-phenyl}-carbamic acid tert.-butyl ester (Example K78) by treatment with TFA in $CH_2Cl_2$ according to the general procedure M. Obtained as a light yellow solid (44 mg).

MS (ISP) 302 [(M+H)$^+$]; mp 204–209° C.

Example 112

4-(7-Cyclopropyl-4-oxo-4,5-dihydro-3H-benzo[b][1,4]diazepin-2-yl)-pyridine-2-carbonitrile Prepared from {2-[3-(2-cyano-pyridin-4-yl)-3-oxo-propionylamino]-4-cyclopropyl-phenyl}-carbamic acid tert.-butyl ester (Example K79) by treatment with TFA in $CH_2Cl_2$ according to the general procedure M. Obtained as a light brown solid (88 mg).

MS (ISP) 303 [(M+H)$^+$]; mp 227–230° C.

Example 113

8-Cyclopropyl-4-(3-imidazol-1-yl-phenyl)-1,3-dihydro-benzo[b][1,4]diazepin-2-one Prepared from {4-cyclopropyl-2-[3-(3-imidazol-1-yl-phenyl)-3-oxo-propionylamino]-phenyl}-carbamic acid tert.-butyl ester (Example K80) by treatment with TFA in $CH_2Cl_2$ according to the general procedure M. Obtained as a light brown solid (41 mg).

MS (ISP) 303 [(M+H)$^+$]; mp 198–200° C.

Example 114

8-(4-Fluoro-phenyl)-4-(3-[1,2,3]triazol-1-yl-phenyl)-1,3-dihydro-benzo[b][1,4]diazepin-2-one Prepared from {2'-fluoro-3-[3-oxo-3-(3-[1,2,3]triazol-1-yl-phenyl)-propionylamino]-biphenyl-4-yl}-carbamic acid tert.-butyl ester (Example K81) by treatment with TFA in $CH_2Cl_2$ according to the general procedure M. Obtained as a light yellow solid (29 mg).

MS (EI) 397 (M$^+$); mp 218–220° C.

Example 115

8-(4-Fluoro-phenylethynyl)-4-(3-[1,2,3]triazol-1-yl-phenyl)-1,3-dihydro-benzo[b][1,4]diazepin-2-one Prepared from {4-(4-fluoro-phenylethynyl)-2-[3-oxo-3-(3-[1,2,3]triazol-1-yl-phenyl)-propionylamino]-phenyl}-carbamic acid tert.-butyl ester (Example K82) by treatment with TFA in $CH_2Cl_2$ according to the general procedure M. Obtained as a light yellow solid (53 mg).

MS (EI) 421 (M$^+$); mp 246–248° C.

Example 116

8-(4-Fluoro-phenyl)-4-(2-imidazol-1-yl-thiazol-4-yl)-1,3-dihydro-benzo[b][1,4]diazepin-2-one Prepared from {4'-fluoro-3-[3-(2-imidazol-1-yl-thiazol-4-yl)-3-oxo-propionylamino]-biphenyl-4-yl}-carbamic acid tert.-butyl ester (Example K83) by treatment with TFA in $CH_2Cl_2$ according to the general procedure M. Obtained as a light brown solid (64 mg).

MS (ISP) 404 [(M+H)$^+$]; mp 214° C.

Example 117

8-(4-Fluoro-phenyl)-4-[3-(3-methyl-isoxazol-5-yl)-phenyl]-1,3-dihydro-benzo[b][1,4]diazepin-2-one Prepared from (4'-fluoro-3-{3-[3-(3-methyl-isoxazol-5-yl)-phenyl]-3-oxo-propionylamino}-biphenyl-4-yl)-carbamic acid tert.-butyl ester (Example K84) by treatment with TFA in $CH_2Cl_2$ according to the general procedure M. Obtained as a light yellow solid (33 mg).

MS (EI) 411 (M$^+$); mp>250° C.

Example 118

3-[7-(2,4-Difluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-2',4'-difluoro-biphenyl-4-yl}-carbamic acid tert.-butyl ester (Example K85) by treatment with TFA in $CH_2Cl_2$ according to the general procedure M. Obtained as a light yellow solid (37 mg).

MS (ISP) 374 [(M+H)$^+$].

Example 119

3-(7-Isopropyl-4-oxo-4,5-dihydro-3H-benzo[b][1,4]diazepin-2-yl)-benzonitrile

Prepared from {2-[3-(3-cyano-phenyl)-3-oxo-propionylamino]-4-isopropyl-phenyl}-carbamic acid tert.-butyl ester (Example K86) by treatment with TFA in $CH_2Cl_2$ according to the general procedure M. Obtained as an off-white solid (25 mg).

MS (ISP) 304 [(M+H)$^+$].

Example 120

8-(4-Fluoro-phenyl)-4-[3-(2-methylsulfanyl-imidazol-1-yl)-phenyl]-1,3-dihydro-benzo[b][1,4]diazepin-2-one Prepared from (4'-fluoro-3-{3-[3-(2-methylsulfanyl-imidazol-1-yl)-phenyl]-3-oxo-propionylamino}-biphenyl-4-yl)-carbamic acid tert.-butyl ester (Example K87) by treatment with TFA in $CH_2Cl_2$ according to the general procedure M. Obtained as a light yellow solid (104 mg).

MS (ISP) 443 [(M+H)$^+$].

Example 121

8-Isopropyl-4-[3-(2-methyl-imidazol-1-yl)-phenyl]-1,3-dihydro-benzo[b][1,4]diazepin-2-one Prepared from (4-isopropyl-2-{3-[3-(2-methyl-imidazol-1-yl)-phenyl]-3-oxo-propionylamino}-phenyl)-carbamic acid tert.-butyl ester (Example K88) by treatment with TFA in $CH_2Cl_2$ according to the general procedure M. Obtained as a light brown solid (94 mg).
MS (ISP) 359 [(M+H)$^+$].

Example 122

8-(2,4-Difluoro-phenyl)-4-[3-(2-methyl-imidazol-1-yl)-phenyl]-1,3-dihydro-benzo[b][1,4]diazepin-2-one Prepared from (2',4'-difluoro-3-{3-[3-(2-methyl-imidazol-1-yl)-phenyl]-3-oxo-propionylamino}-biphenyl-4-yl)-carbamic acid tert.-butyl ester (Example K89) by treatment with TFA in $CH_2Cl_2$ according to the general procedure M. Obtained as a light brown solid (71 mg).
MS (ISP) 429 [(M+H)$^+$].

Example 123

8-(2,4-Difluoro-phenyl)-4-(3-[1,2,3]triazol-1-yl-phenyl)-1,3-dihydro-benzo[b][1,4]diazepin-2-one Prepared from {2',4'-difluoro-3-[3-oxo-3-(3-[1,2,3]triazol-1-yl-phenyl)-propionylamino]-biphenyl-4-yl}-carbamic acid tert.-butyl ester (Example K90) by treatment with TFA in $CH_2Cl_2$ according to the general procedure M. Obtained as a light brown solid (78 mg).
MS (ISP) 416 [(M+H)$^+$].

Example 124

8-(2-Fluoro-phenyl)-4-(2-imidazol-1-yl-thiazol-4-yl)-1,3-dihydro-benzo[b][1,4]diazepin-2-one Prepared from {2'-fluoro-3-[3-(2-imidazol-1-yl-thiazol-4-yl)-3-oxo-propionylamino]-biphenyl-4-yl}-carbamic acid tert.-butyl ester (Example K91) by treatment with TFA in $CH_2Cl_2$ according to the general procedure M. Obtained as a light yellow solid (46 mg).
MS (ISP) 404 [(M+H)$^+$]; mp 194–197° C.

Example 125

3-[7-(2,5-Difluoro-phenyl)-4-oxo-4,5-dihydro-3H-benzo[b][1,4]diazepin-2-yl]-benzonitrile Prepared from {3-[3-(3-cyano-phenyl)-3-oxo-propionylamino]-2',5'-difluoro-biphenyl-4-yl}-carbamic acid tert.-butyl ester (Example K92) by treatment with TFA in $CH_2Cl_2$ according to the general procedure M. Obtained as a light yellow solid (49 mg).
MS (EI) 373 (M$^+$); mp 247° C.

Example 126

8-(2,5-Difluoro-phenyl)-4-(3-[1,2,3]triazol-1-yl-phenyl)-1,3-dihydro-benzo[b][1,4]diazepin-2-one Prepared from {2',5'-difluoro-3-[3-oxo-3-(3-[1,2,3]triazol-1-yl-phenyl)-propionylamino]-biphenyl-4-yl}-carbamic acid tert.-butyl ester (Example K93) by treatment with TFA in $CH_2Cl_2$ according to the general procedure M. Obtained as a light yellow solid (67 mg).
MS (EI) 415 (M$^+$); mp 231° C.

Example 127

8-(2-Fluoro-phenyl)-4-[3-(3-methyl-isoxazol-5-yl)-phenyl]-1,3-dihydro-benzo[b][1,4]diazepin-2-one Prepared from (2'-fluoro-3-{3-[3-(3-methyl-isoxazol-5-yl)-phenyl]-3-oxo-propionylamino}-biphenyl-4-yl)-carbamic acid tert.-butyl ester (Example K94) by treatment with TFA in $CH_2Cl_2$ according to the general procedure M. Obtained as a light yellow solid (100 mg).
MS (EI) 411 (M$^+$); mp 222–224° C.

Example 128

7-Methyl-4-[3-(1-methyl-1H-imidazol-2-yl)-phenyl]-8-phenylethynyl-1,3-dihydro-benzo[b][1,4]diazepin-2-one Prepared from (2-amino-4-phenylethynyl-phenyl)-carbamic acid tert.-butyl ester (Example G2) (620 mg, 2.0 mmol) and 3-[3-(1-methyl-1H-imidazol-2-yl)-phenyl]-3-oxo-propionic acid tert.-butyl ester (Example H21) (1.26 g, 4.2 mmol) according to the general procedure K. The obtained material was deprotected and cyclized by treatment with TFA in $CH_2Cl_2$ according to the general procedure M. Obtained as a light yellow solid (81 mg).
MS (ISP) 417.2 [(M+H)$^+$]; mp 202–205° C.

Example 129

8-(2,3-Difluoro-phenyl)-4-(3-[1,2,3]triazol-1-yl-phenyl)-1,3-dihydro-benzo[b][1,4]diazepin-2-one Prepared from {2',3'-difluoro-3-[3-oxo-3-(3-[1,2,3]triazol-1-yl-phenyl)-propionylamino]-biphenyl-4-yl}-carbamic acid tert.-butyl ester (Example K95) (118 mg, 0.22 mmol) by treatment with TFA in $CH_2Cl_2$ according to the general procedure M. Obtained as a yellow solid (74 mg). mp 230° C.

Example 130

3-[7-(2,4-Difluoro-phenylethynyl)-4-oxo-4,5-dihydro-3H-benzo[b][1,4]diazepin-2-yl]-benzonitrile Prepared from [2-[3-(3-cyano-phenyl)-3-oxo-propionylamino]-4-(2,4-difluoro-phenylethynyl)-phenyl]-carbamic acid tert.-butyl ester (Example K96) by treatment with TFA in $CH_2Cl_2$ according to the general procedure M. Obtained as a light yellow solid (87 mg).
MS (EI) 397 (M$^+$); mp 240–246° C.

Example 131

3-[7-(2-Fluoro-phenylethynyl)-4-oxo-4,5-dihydro-3H-benzo[b][1,4]diazepin-2-yl]-benzonitrile Prepared from [2-[3-(3-cyano-phenyl)-3-oxo-propionylamino]-4-(2-fluoro-phenylethynyl)-phenyl]-carbamic acid tert.-butyl ester (Example K97) by treatment with TFA in $CH_2Cl_2$ according to the general procedure M. Obtained as a yellow solid (82 mg).
MS (EI) 379 (M$^+$); mp 213–214° C.

Example 132

8-Phenylethynyl-4-(3-trimethylsilanylethynyl-phenyl)-1,3-dihydro-benzo[b][1,4]diazepin-2-one Prepared from 4-(3-iodophenyl)-8-phenylethynyl-1,3-dihydro-benzo[b][1,4]diazepin-2-one (Example 11) (231 mg, 0.5 mmol) and trimethylsilylacetylene (0.4 mL, 1.0 mmol) according to the general procedure F. Obtained as a light brown solid (102 mg).
MS (EI) 432 (M$^+$); mp 169–171° C. (dec.).

Example 133

4-(3-Ethynyl-phenyl)-8-phenylethynyl-1,3-dihydro-benzo[b][1,4]diazepin-2-one

Prepared from 8-phenylethynyl-4-(3-trimethylsilanylethynyl-phenyl)-1,3-dihydro-benzo[b][1,4]diazepin-2-one (Example 132) (63 mg, 0.146 mmol) by treatment with 1N NaOH (3 drops) in MeOH (3 mL) and THF (0.5 mL) at 23° C. for 2 h. Obtained as a brown solid (31 mg).
MS (ISP) 361 [(M+H)$^+$]; mp>250° C. (dec.).

Example 134

3-[7-(3-Hydroxy-3-methyl-but-1-ynyl)-4-oxo-4,5-dihydro-3H-benzo[b][1,4]diazepin-2-yl]-benzonitrile Prepared from 4-(3-iodophenyl)-8-phenylethynyl-1,3-dihydro-benzo[b][1,4]diazepin-2-one (Example 11) (194 mg, 0.5 mmol) and 2-methyl-3-butyn-2-ol (105 mg, 1.25 mmol) according to the general procedure F. Obtained as a yellow solid (147 mg).
MS (EI) 343 (M$^+$); mp 243° C.

Example 135

3-[7-(1-Hydroxy-cyclohexylethynyl)-4-oxo-4,5-dihydro-3H-benzo[b][1,4]diazepin-2-yl]-benzonitrile Prepared from 4-(3-iodophenyl)-8-phenylethynyl-1,3-dihydro-benzo[b][1,4]diazepin-2-one (Example 11) (308 mg, 0.80 mmol) and 1-ethynyl-1-cyclohexanol (248 mg, 2.00 mmol) according to the general procedure F. Obtained as a beige solid (262 mg).
MS (ISP) 384 [(M+H)$^+$]; mp 196° C.

Example 136

3-(7-Cyclohex-1-enylethynyl-4-oxo-4,5-dihydro-3H-benzo[b][1,4]diazepin-2-yl)-benzonitrile Prepared from 3-[7-(1-hydroxy-cyclohexylethynyl)-4-oxo-4,5-dihydro-3H-benzo[b][1,4]diazepin-2-yl]-benzonitrile (Example 135) (50 mg, 0.13 mmol) by treatment with TFA in CH$_2$Cl$_2$ according to the general procedure M. Obtained as a light yellow solid (22 mg).
MS (EI) 365 (M$^+$); mp 228° C.

Example 137

3-[7-(3-Methyl-but-3-en-1-ynyl)-4-oxo-4,5-dihydro-3H-benzo[b][1,4]diazepin-2-yl]-benzonitrile Prepared from 3-[7-(3-hydroxy-3-methyl-but-1-ynyl)-4-oxo-4,5-dihydro-3H-benzo[b][1,4]diazepin-2-yl]-benzonitrile (Example 134) (50 mg, 0.15 mmol) by treatment with TFA in CH$_2$Cl$_2$ according to the general procedure M. Obtained as a sand solid (33 mg).
MS (ISP) 326 [(M+H)$^+$]; mp 231° C.

Example 138

3-[7-(3,6-Dihydro-2H-pyran-4-ylethynyl)-4-oxo-4,5-dihydro-3H-benzo[b][1,4]diazepin-2-yl]-benzonitrile Prepared from 3-[7-(4-hydroxy-tetrahydro-pyran-4-ylethynyl)-4-oxo-4,5-dihydro-3H-benzo[b][1,4]diazepin-2-yl]-benzonitrile [prepared from 4-(3-iodophenyl)-8-phenylethynyl-1,3-dihydro-benzo[b][1,4]diazepin-2-one (Example 11) (387 mg, 1.0 mmol) and 4-ethynyl-tetrahydro-pyran-4-ol [CAS-No. 57385-16-7] (315 mg, 2.5 mmol) according to the general procedure F. Obtained as a yellow solid (296 mg)] (50 mg, 0.13 mmol) by treatment with TFA in CH$_2$Cl$_2$ according to the general procedure M. Obtained as a light yellow solid (16 mg).
MS (EI) 367 (M$^+$); mp 238° C.

Example 139

4-[2-(3-Cyano-phenyl)-4-oxo-4,5-dihydro-3H-benzo[b][1,4]diazepin-7-ylethynyl]-3,6-dihydro-2H-pyridine-1-carboxylic acid tert.-butyl ester Prepared from 4-(3-iodophenyl)-8-phenylethynyl-1,3-dihydro-benzo[b][1,4]diazepin-2-one (Example 11) (1.16 g, 3.0 mmol) and 4-ethynyl-3,6-dihydro-2H-pyridine-1-carboxylic acid tert.-butyl ester [CAS-No. 177984-28-0] (0.93 g, 4.5 mmol) according to the general procedure F. Obtained as a yellow solid (620 mg).
MS (ISP) 467 [(M+H)$^+$]; mp 239° C.

Example 140

3-[4-Oxo-7-(1,2,3,6-tetrahydro-pyridin-4-ylethynyl)-4,5-dihydro-3H-benzo[b][1,4]diazepin-2-yl]-benzonitrile Prepared from 4-[2-(3-cyano-phenyl)-4-oxo-4,5-dihydro-3H-benzo[b][1,4]diazepin-7-ylethynyl]-3,6-dihydro-2H-pyridine-1-carboxylic acid tert.-butyl ester (Example 139) (573 mg, 1.13 mmol) by treatment with TFA in CH$_2$Cl$_2$ according to the general procedure M. Obtained as an off-white solid (434 mg).
MS (ISP) 367 [(M+H)$^+$]; mp 184° C.

Example 141

3-[7-(1-Acetyl-1,2,3,6-tetrahydro-pyridin-4-ylethynyl)-4-oxo-4,5-dihydro-3H-benzo[b][1,4]diazepin-2-yl]-benzonitrile Prepared from 3-[4-oxo-7-(1,2,3,6-tetrahydro-pyridin-4-ylethynyl)-4,5-dihydro-3H-benzo[b][1,4]diazepin-2-yl]-benzonitrile (Example 140) (55 mg, 0.15 mmol) by treatment with Ac$_2$O (0.017 mL, 0.165 mmol) in THF (3 mL) at 23° C. for 1 h. Obtained as a sand solid (59 mg).
MS (ISP) 409 [(M+H)$^+$]; mp 203° C.

Example 142

3-[7-(1-Methanesulfonyl-1,2,3,6-tetrahydro-pyridin-4-ylethynyl)-4-oxo-4,5-dihydro-3H-benzo[b][1,4]diazepin-2-yl]-benzonitrile Prepared from 3-[4-oxo-7-(1,2,3,6-tetrahydro-pyridin-4-ylethynyl)-4,5-dihydro-3H-benzo[b][1,4]diazepin-2-yl]-benzonitrile (Example 140) (55 mg, 0.15 mmol) by treatment with methanesulfonyl chloride (0.012 mL, 0.15 mmol) and Et$_3$N (0.021 mL, 0.15 mmol) in THF (3 mL) at 23° C. for 23 h. Obtained as a yellow solid (38 mg).

MS (EI) 444 (M$^+$); mp 235° C.

Example 143

3-{7-[1-(2,2-Dimethyl-propionyl)-1,2,3,6-tetrahydro-pyridin-4-ylethynyl]-4-oxo-4,5-dihydro-3H-benzo[b][1,4]diazepin-2-yl}-benzonitrile Prepared from 3-[4-oxo-7-(1,2,3,6-tetrahydro-pyridin-4-ylethynyl)-4,5-dihydro-3H-benzo[b][1,4]diazepin-2-yl]-benzonitrile (Example 140) (55 mg, 0.15 mmol) by treatment with pivaloyl chloride (0.02 mL, 0.165 mmol) and Et$_3$N (0.021 mL, 0.15 mmol) in THF (3 mL) at 23° C. for 19 h. Obtained as a sand solid (26 mg).

MS (ISP) 451 [(M+H)$^+$]; mp 219° C.

Example 144

3-[4-Oxo-7-(3-oxo-cyclohex-1-enylethynyl)-4,5-dihydro-3H-benzo[b][1,4]diazepin-2-yl]-benzonitrile Prepared from 4-(3-iodophenyl)-8-phenylethynyl-1,3-dihydro-benzo[b][1,4]diazepin-2-one (Example 11) (500 mg, 1.29 mmol) and 3-ethynyl-cyclohex-2-enone [CAS-No. 124267-26-1] (310 mg, 2.58 mmol) according to the general procedure F. Obtained as a yellow solid (346 mg).

MS (EI) 379 (M$^+$); mp 110° C.

Example 145

3-[7-(4-Fluoro-phenylethynyl)-4-oxo-4,5-dihydro-3H-benzo[b][1,4]diazepin-2-yl]-benzonitrile Prepared from [2-[3-(3-cyano-phenyl)-3-oxo-propionylamino]-4-(4-fluoro-phenylethynyl)-phenyl]-carbamic acid tert.-butyl ester (Example K98) (307 mg, 0.62 mmol) by treatment with TFA in CH$_2$Cl$_2$ according to the general procedure M. Obtained as a eggshell solid (146 mg).

MS (EI) 379 (M$^+$); mp 245–246° C.

The following examples relate to the palladium-catalyzed carbonylation of the 4-(3-iodophenyl)-8-phenylethynyl-1,3-dihydro-benzo[b][1,4]diazepin-2-one in the presence of secondary amines leads directly to the corresponding amides as shown in synthetic scheme H.

General Procedure N

Preparation of 4-[3-(Amino-4-carbonyl)-phenyl]-8-phenylethynyl-1,3-dihydro-benzo[b][1,4]diazepin-2-ones by Pd-catalyzed carbonylative amination of 4-(3-iodophenyl)-8-phenylethynyl-1,3-dihydro-benzo[b][1,4]diazepin-2-one A solution of 4-(3-iodophenyl)-8-phenylethynyl-1,3-dihydro-benzo[b][1,4]diazepin-2-one (Example 11) (1.0 mmol), the secondary amine (5.0 mmol), PPh$_3$ (6 mol %) or dppp (3 mol %), Pd(OAc)$_2$ (3 mol %) and Et$_3$N (2.0 mmol) in DMF (4 mL) was stirred at 23° C. under CO-atmosphere until tlc indicated complete consumption of the iodide. After dilution with EtOAc, washing with sat. NaHCO$_3$-sol. and brine, the organic phase was dried over Na$_2$SO$_4$. Removal of the solvent left a brown oil, which was purified by silica gel column chromatography with hexane/EtOAc to give the title compound.

Example 146

4-[3-(Morpholine-4-carbonyl)-phenyl]-8-phenylethynyl-1,3-dihydro-benzo[b][1,4]diazepin-2-one Prepared from 4-(3-iodophenyl)-8-phenylethynyl-1,3-dihydro-benzo[b][1,4]diazepin-2-one (Example 11) (471 mg, 1.02 mmol) and morpholine (0.44 mL, 5.09 mmol) according to the general procedure N. Obtained as a light yellow solid (324 mg).

MS (ISP) 450 [(M+H)$^+$]; mp 142–145° C. (dec.).

Example 147

4-[3-(4-Methyl-piperazine-1-carbonyl)-phenyl]-8-phenylethynyl-1,3-dihydro-benzo[b][1,4]diazepin-2-one Prepared from 4-(3-iodophenyl)-8-phenylethynyl-1,3-dihydro-benzo[b][1,4]diazepin-2-one (Example 11) (231 mg, 0.5 mmol) and N-methylpiperazine (0.28 mL, 2.5 mmol) according to the general procedure N. Obtained as a light yellow solid (65 mg).

MS (ISP) 463 [(M+H)$^+$]; mp 168–172° C. (dec.).

Example 148

3-(4-Oxo-7-phenylethynyl-4,5-dihydro-3H-benzo[b][1,4]diazepin-2-yl)-benzamide

Prepared from 4-(3-iodophenyl)-8-phenylethynyl-1,3-dihydro-benzo[b][1,4]diazepin-2-one (Example 11) (231 mg, 0.5 mmol) and hexamethyldisilazane (0.52 mL, 2.5 mmol) according to the general procedure N. Obtained as a yellow solid (104 mg).

MS (EI) 379 (M$^+$); mp>250° C. (dec.).

Example 149

3-[7-(4-Fluoro-phenyl)-4-oxo-4,5-dihydro-3H-benzo[b][1,4]diazepin-2-yl]-thiobenzamide Preparation of 4-oxo-4,5-dihydro-3H-benzo[b][1,4]diazepin-2-yl]-thiobenzamides (according to Pen-Yuan Lin et al. *Synthesis* 1992, 1219]: To a solution of hexamethyldisilthiane (1.45 g, 8.0 mmol) in 1,3-dimethyl-2-imidazolidinone (8 mL) was added at 23° C. sodium methoxide (0.31 g, 6.8 mmol). The mixture was stirred for 5 min. and the blue solution formed was then added to a solution of 3-[7-(4-fluoro-phenyl)-4-oxo-4,5-dihydro-3H-benzo[b][1,4]diazepin-2-yl]-benzonitrile (Example 57) (1.42 g, 4 mmol) in 1,3-dimethyl-2-imidazolidinone (12 mL). The mixture was stirred for 3 h at 23° C. and then poured into water (100 mL). Stirring was continued for 0.5 h and the precipitate was isolated by filtration and triturated with ethyl acetate (50 mL) to give the title compound as light yellow solid (1.38 g).

MS (ISN) 387.9 [(M−H)$^-$]; mp 267–270° C. (dec.).

Example 150

3-[7-(2-Fluoro-phenyl)-4-oxo-4,5-dihydro-3H-benzo[b][1,4]diazepin-2-yl]-thiobenzamide 3-[7-(2-Fluoro-phenyl)-4-oxo-4,5-dihydro-3H-benzo[b][1,4]diazepin-2-yl]-benzonitrile (Example 86) (0.53 g) was subjected in an analogous manner to the procedure described in Example 149 to give, after trituration of the crude product with ethyl acetate, the title compound as light yellow solid (0.46 g).

MS (ISN) 387.9 [(M−H)$^-$]; mp 232–234° C. (dec.).

Example 151

4-[7-(4-Fluoro-phenyl)-4-oxo-4,5-dihydro-3H-benzo[b][1,4]diazepin-2-yl]-pyridine-2-carbothioic acid amide (Example 94) (0.36 g) was subjected in an analogous manner the procedure described in Example 149 to give, after trituration of the crude product with acetone, the title compound as light yellow solid (0.33 g).

MS (ISN) 388.9 [(M−H)$^-$]; mp 280–283° C. (dec.).

Example 152

8-(4-Fluoro-phenyl)-4-[3-(4-methyl-thiazol-2-yl)-phenyl]-1,3-dihydro-benzo[b][1,4]diazepin-2-one To a suspension of 3-[7-(4-fluoro-phenyl)-4-oxo-4,5-dihydro-3H-benzo[b][1,4]diazepin-2-yl]-thiobenzamide (Example 149) (97 mg, (0.25 mmol) in ethanol (5 mL) was added chloroacetone (0.1 mL, 1.25 mmol) and the mixture was heated at reflux. After 1 h and after 5 h of heating, more chloroacetone (2 times 0.1 mL, 1.25 mmol) was added. After 20 h the mixture was cooled to 0° C. and stirred for 0.5 h, and the title compound was isolated by filtration as light yellow solid (61 mg).

MS (ISP) 428.4 [(M+H)$^+$]; mp 259–261° C. (dec.).

Example 153

2-{3-[7-(4-Fluoro-phenyl)-4-oxo-4,5-dihydro-3H-benzo[b][1,4]diazepin-2-yl]-phenyl}-thiazole-4-carboxylic acid ethyl ester A mixture of 3-[7-(4-fluoro-phenyl)-4-oxo-4,5-dihydro-3H-benzo[b][1,4]diazepin-2-yl]-thiobenzamide (Example 149) (39 mg, 0.1 mmol) and ethyl bromopyruvate (29 mg, 0.15 mmol) in ethanol (0.5 mL) was heated at reflux for 7 h. The solution was cooled to 0° C., stirred for 0.5 h, and the title compound was isolated by filtration as light yellow solid (29 mg).

MS (ISN) 484.2 [(M−H)$^-$]; mp 236–238° C. (dec.).

Example 154

2-{3-[7-(2-Fluoro-phenyl)-4-oxo-4,5-dihydro-3H-benzo[b][1,4]diazepin-2-yl]-phenyl}-thiazole-4-carboxylic acid ethyl ester 3-[7-(2-Fluoro-phenyl)-4-oxo-4,5-dihydro-3H-benzo[b][1,4]diazepin-2-yl]-thiobenzamide (Example 150) (0.24 g) was subjected in an analogous manner to the procedure described in Example 153. The reaction mixture was evaporated in vacuum and the residue was triturated with ethyl acetate to give the title compound as light yellow solid (0.29 g).

MS (ISP) 503.4 [(M+NH$_4$)$^+$]; mp 172–175° C.

Example 155

2-{4-[7-(4-Fluoro-phenyl)-4-oxo-4,5-dihydro-3H-benzo[b][1,4]diazepin-2-yl]-pyridin-2-yl}-thiazole-4-carboxylic acid ethyl ester -[7-(4-Fluoro-phenyl)-4-oxo-4,5-dihydro-3H-benzo[b][1,4]diazepin-2-yl]-pyridine-2-carbothioic acid amide (Example 151) (160 mg) was subjected in an analogous manner to the procedure described in Example 153. The cooled reaction solution was diluted with ethyl acetate, washed with NaHCO$_3$-sol. and with brine, dried over Na$_2$SO$_4$ and evaporated in vacuum. The crude product was chromatographed on silica gel using ethyl acetate/hexane (2:1) as eluent, and the purified product was triturated with dichloromethane/diethyl ether to give the title compound as light yellow solid (40 mg).

MS (ISN) 485.1 [(M−H)$^-$]; mp 238–240° C. (dec.).

Example 156

8-(4-Fluoro-phenyl)-4-[3-(4-hydroxymethyl-thiazol-2-yl)-phenyl]-1,3-dihydro-benzo[b][1,4]diazepin-2-one To a solution of 2-{3-[7-(4-fluoro-phenyl)-4-oxo-4,5-dihydro-3H-benzo[b][1,4]diazepin-2-yl]-phenyl}-thiazole-4-carboxylic acid ethyl ester (Example 153) (110 mg, 0.23 mmol) in THF (7 mL) was added a 3.5 M solution of sodium dihydrido-bis(2-methoxyethoxy)aluminate in toluene (0.66 mL, 2.3 mmol). The raction mixture was stirred at 23° C. for 15 min. and then poured into ice-cold 10% aq. acetic acid. The mixture was extracted with ethyl acetate and the organic layer was washed successively with H$_2$O, sat. Na$_2$CO$_3$-sol. and brine, dried over Na$_2$SO$_4$ and evaporated in vacuum. The residue was triturated with ethyl acetate to give the title compound as light yellow solid (48 mg).

MS (ISN) 442.1 [(M−H)$^-$]; mp 235–239° C. (dec.).

Example 157

8-(2-Fluoro-phenyl)-4-[3-(4-hydroxymethyl-thiazol-2-yl)-phenyl]-1,3-dihydro-benzo[b][1,4]diazepin-2-one 2-{3-[7-(2-Fluoro-phenyl)-4-oxo-4,5-dihydro-3H-benzo[b][1,4]diazepin-2-yl]-phenyl}-thiazole-4-carboxylic acid ethyl ester (Example 154) (97 mg) was subjected in an analogous manner to the procedure described in Example 156 to give the title compound as light yellow solid (30 mg).

MS (ISN) 442.1 [(M−H)$^-$]; mp 238–244° C. (dec.).

Example 158

8-(4-Fluoro-phenyl)-4-[2-(4-hydroxymethyl-thiazol-2-yl)-pyridin-4-yl]-1,3-dihydro-benzo[b][1,4]diazepin-2-one 2-{4-[7-(4-Fluoro-phenyl)-4-oxo-4,5-dihydro-3H-benzo[b][1,4]diazepin-2-yl]-pyridin-2-yl}-thiazole-4-carboxylic acid ethyl ester (Example 155) (84 mg) was subjected in an analogous manner to the procedure described in Example 156. The crude product was chromatographed on silica gel using ethyl acetate/hexane (2:1) and ethyl acetate as eluent, and the purified product was crystallized from ethyl acetate/hexane to give the title compound as light yellow solid (16 mg).

MS (ISP) 445.2 [(M+H)$^+$]; mp 225–229° C.

Example 159

2-{3-[7-(4-Fluoro-phenyl)-4-oxo-4,5-dihydro-3H-benzo[b][1,4]diazepin-2-yl]-phenyl}-thiazole-4-carboxylic acid To a solution of 2-{3-[7-(4-fluoro-phenyl)-4-oxo-4,5-dihydro-3H-benzo[b][1,4]diazepin-2-yl]-phenyl}-thiazole-4-carboxylic acid ethyl ester (Example 153) (49 mg, 0.1 mmol) in a mixture of MeOH (1 mL) and DMSO (1.5 mL) was added 2N KOH (1 mL, 2 mmol). The mixture was stirred at 23° C. for 0.5 h and then partitioned between ethyl acetate and H$_2$O. The pH of the aqueous phase was set to 3 by the addition of 3N HCl and then stirred in the ice-bath for 0.5 h. The precipitate was collected by filtration, triturated with EtOH/Et$_2$O (1/1) and dried, to give the title compound as light yellow solid (25 mg).

MS (ISN) 456.4 [(M−H)$^-$]; mp 286–290° C. (dec.).

Example 160

2-{3-[7-(2-Fluoro-phenyl)-4-oxo-4,5-dihydro-3H-benzo[b][1,4]diazepin-2-yl]-phenyl}-thiazole-4-carboxylic acid 2-{3-[7-(2-Fluoro-phenyl)-4-oxo-4,5-dihydro-3H-benzo[b][1,4]diazepin-2-yl]-phenyl}-thiazole-4-carboxylic acid ethyl ester (Example 154) (97 mg) was subjected in an analogous manner to the procedure described in Example 159 to give the title compound as light yellow solid (60 mg).

MS (ISN) 456.2 [(M−H)$^-$]; mp 261–263° C. (dec.).

Example 161

2-{3-[7-(4-Fluoro-phenyl)-4-oxo-4,5-dihydro-3H-benzo[b][1,4]diazepin-2-yl]-phenyl}-thiazole-4-carboxylic acid (2-hydroxy-ethyl)-amide A solution of 2-{3-[7-(4-fluoro-phenyl)-4-oxo-4,5-dihydro-3H-benzo[b][1,4]diazepin-2-yl]-phenyl}-thiazole-4-carboxylic acid ethyl ester (Example 153) (49 mg, 0.1 mmol) in 2-amino-ethanol was heated to 40° C. for 40 min. The cooled solution was partitioned between ethyl acetate and H$_2$O and the organic layer was dried over Na$_2$SO$_4$ and evaporated in vacuum. The residue was triturated with ethyl acetate to give to give the title compound as light yellow solid (21 mg).

MS (ISP) 518.3 [(M+NH$_4$)$^+$]; mp 238–245° C. (dec.).

Example 162

2-{3-[7-(4-Fluoro-phenyl)-4-oxo-4,5-dihydro-3H-benzo[b][1,4]diazepin-2-yl]-phenyl}-4-methyl-thiazole-5-carboxylic acid (2-hydroxy-ethyl)-amide A mixture 3-[7-(4-fluoro-phenyl)-4-oxo-4,5-dihydro-3H-benzo[b][1,4]diazepin-2-yl]-thiobenzamide (Example 149) (78 mg, 0.2 mmol) and ethyl 4-chloro-3-oxo-butanoate (164 mg, 1.0 mmol) in ethanol (4 mL) was heated at reflux for 24 h. The solution was cooled to 0° C. and stirred for 0.5 h. The crystals were isolated by filtration and subsequently suspended in 2-amino-ethanol (4 mL). The mixture was stirred at 70° C. for 4 h, cooled to 23° C., and partitioned between ethyl acetate and H$_2$O. The organic layer was dried over Na$_2$SO$_4$ and evaporated in vacuum and the residue was triturated with ethyl acetate to give the title compound as light yellow solid (37 mg).

MS (ISP) 515.3 [(M+H)$^+$]; mp 248–251° C. (dec.).

Example 163

3-[7-(4-Fluoro-phenyl)-4-oxo-4,5-dihydro-3H-benzo[b][1,4]diazepin-2-yl]-benzoic acid To a suspension of 3-[7-(4-fluoro-phenyl)-4-oxo-4,5-dihydro-3H-benzo[b][1,4]diazepin-2-yl]-benzonitrile (Example 57) (355 mg, 1 mmol) in EtOH (2 mL) was added 2N KOH (5 mL). The mixture was heated at reflux for 3 h, then cooled to 23° C. and partitioned between ethyl acetate and H$_2$O. The pH of the aqueous phase was set to 3 by the addition of 3N HCl, a precipitate being formed. The mixture was stirred in the ice-bath for nn 0.5 h. The crystalline solid was collected by filtration, triturated with ethyl acetate and dried, to give the title compound as light yellow solid (218 mg).

MS (ISN) 373.3 [(M−H)$^-$]; mp 290–296° C. (dec.).*

Example 164

4-[7-(4-Fluoro-phenyl)-4-oxo-4,5-dihydro-3H-benzo[b][1,4]diazepin-2-yl]-pyridine-2-carboxylic acid 4-[7-(4-Fluoro-phenyl)-4-oxo-4,5-dihydro-3H-benzo[b][1,4]diazepin-2-yl]-pyridine-2-carbonitrile (Example 94) (356 mg) was subjected in an analogous manner to the procedure described in Example 163. The reaction mixture was partitioned between ethyl acetate and H$_2$O, and the pH of the aqueous phase was set to 3 by the addition of 3N HCl, a precipitate being formed. The mixture was extracted with ethyl acetate and the organic layer was washed with brine, dried over Na$_2$SO$_4$, and evaporated in vacuum. The residue was triturated with EtOH to give the title compound as yellow solid (190 mg).

MS (ISN) 374.2 [(M−H)$^-$]; mp 211–213° C. (dec.).

Example 165

8-(4-Fluoro-phenyl)-4-[3-(5-methyl-[1,3,4]oxadiazol-2-yl)-phenyl]-1,3-dihydro-benzo[b][1,4]diazepin-2-one A mixture of 3-[7-(4-fluoro-phenyl)-4-oxo-4,5-dihydro-3H-benzo[b][1,4]diazepin-2-yl]-benzoic acid hydrazide (Starting material 8a-2) (58 mg, 0.15 mmol) and ethyl acetimidate hydrochloride (74 mg, 0.6 mmol) in pyridine (0.6 mL) was heated to 100° C. for 2 h. The mixture was cooled to 23° C., diluted with H$_2$O (30 mL) and stirred for 20 min. The precipitate was collected by filtration, and the crude product was purified by chromatography on silica gel using ethyl acetate/hexane (2:1) as eluent. The purified product was crystallized from Et$_2$O/hexane to give the title compound as light yellow solid (28 mg).

MS (ISP) 430.3 [(M+NH$_4$)$^+$]; mp 254–256° C. (dec.).

Starting Material 8a-1

3-[7-(3-Fluoromethyl-phenyl)-8-methyl-4-oxo-4,5-dihydro-3H-benzo[b][1,4]diazepin-2-yl]-benzoic acid allyl ester To a solution of 3-[7-(4-fluoro-phenyl)-4-oxo-4,5-dihydro-3H-benzo[b][1,4]diazepin-2-yl]-benzoic acid (Example 163) (749 mg, 2 mmol) and 1,1,3,3,-tetramethylguanidine (230 mg, 2 mmol) in DMSO (24 mL) was added allyl bromide (242 mg, 2 mmol) and the mixture was stirred at 23° C. for 2.5 h. H$_2$O (100 mL) was added and stirring was continued for 20 min. The precipitate was collected by filtration and triturated with ethyl acetate/Et2O (1:1) to give the title compound as light yellow solid (705 mg).
MS (ISP) 415.2 [(M+H)$^+$]; mp 226–228° C.

Starting Material 8a-2

3-[7-(4-Fluoro-phenyl)-4-oxo-4,5-dihydro-3H-benzo[b][1,4]diazepin-2-yl]-benzoic acid hydrazide To a suspension of 3-[7-(3-fluoromethyl-phenyl)-8-methyl-4-oxo-4,5-dihydro-3H-benzo[b][1,4]diazepin-2-yl]-benzoic acid allyl ester (Starting material 8a-1) (207 mg, 0.5 mmol) in MeOH (3.5 mL) was added hydrazine hydrate (0.25 mL, 5 mmol). The mixture was stirred at 60° C. for 15 h, then cooled to 23° C. and diluted with H$_2$O (35 mL). The precipitate was collected by filtration and dried, and the crude product was purified by chromatography on silica gel using ethyl acetate/hexane (1:1) as eluent. The purified product was crystallized from Et$_2$O/hexane to give the title compound as light yellow solid (64 mg).
MS (ISN) 387.0 [(M−H)$^-$]; mp 256–258° C. (dec.).

Example 166

4-[3-(4,5-Dimethyl-4H-[1,2,4]triazol-3-yl)-phenyl]-8-(4-fluoro-phenyl)-1,3-dihydro-benzo[b][1,4]diazepin-2-one A mixture of 3-[7-(4-fluoro-phenyl)-4-oxo-4,5-dihydro-3H-benzo[b][1,4]diazepin-2-yl]-benzoic acid hydrazide (Starting material 8a-2)(234 mg, 0.6 mmol) and ethyl acetimidate hydrochloride (185 mg, 1.5 mmol) in EtOH (12 mL) was heated at reflux for 0.5 h. The mixture was cooled and partitioned between ethyl acetate and H2O. The organic layer was dried over Na2SO4 and evaporated in vacuum to give an amorphous residue (261 mg). A sample of this material (92 mg) was dissolved in a 33% solution (3 mL) of methylamine in EtOH. After being stirred for 0.5 h at 23° C., the reaction mixture was evaporated in vacuum and the residue was heated in 1,4-dioxane (5 mL) to 100° C. for 2 h. The solvent was evaporated in vacuum and the crude product was chromatographed on silica gel using ethyl acetate and ethyl acetate/methanol (4:1) as eluent. The purified product was triturated with ethyl acetate to give the title compound as light yellow solid (26 mg).
MS (ISP) 426.4 (M+H)$^+$; mp 238–240° C. (dec.).

Example 167

3-[7-(4-Fluoro-phenyl)-4-oxo-4,5-dihydro-3H-benzo[b][1,4]diazepin-2-yl]-N-hydroxy-benzamidine To a stirred suspension of 3-[7-(4-fluoro-phenyl)-4-oxo-4,5-dihydro-3H-benzo[b][1,4]diazepin-2-yl]-benzonitrile (Example 57) (355 mg, 1 mmol) in EtOH (60 mL) was added at 23° C. over 6 h 50% aqueous hydroxylamine solution (3.48 mL, 60 mmol) in 6 portions. The mixture was cooled in the ice-bath, diluted with H$_2$O (100 mL) and stirred for 1 h. The precipitate was collected by filtration, washed with water and Et$_2$O, and triturated with ethyl acetate to give the title compound as light yellow solid (336 mg).
MS (ISP) 389.2 [(M+H)$^+$]; mp 257–259° C. (dec.).

Example 168

8-(4-Fluoro-phenyl)-4-{3-[5-(3-hydroxy-propyl)-[1,2,4]oxadiazol-3-yl]-phenyl}-1,3-dihydro-benzo[b][1,4]diazepin-2-one To a stirred suspension of 3-[7-(4-fluoro-phenyl)-4-oxo-4,5-dihydro-3H-benzo[b][1,4]diazepin-2-yl]-N-hydroxy-benzamidine (Example 167) (78 mg, 0.2 mmol) in EtOH (3 mL) was added at 23° C. sodium hydride (55% dispersion in oil, 32 mg, 0.8 mmol) and the mixture was stirred at 23° C. for 5 min. Butyrolactone (103 mg, 1.2 mmol) was added and the mixture was heated to 70° C. for 3 h. The reaction mixture was cooled to 23° C. and partitioned between ethyl acetate and H$_2$O. The organic layer was dried over Na$_2$SO$_4$, evaporated in vacuum, and the residue was crystallized from dichloromethane to give the title compound as light yellow solid (60 mg).
MS (ISP) 457.3 [(M+H)$^+$]; mp 220–222° C.

Example 169

8-(4-Fluoro-phenyl)-4-[3-(3-methyl-[1,2,4]oxadiazol-5-yl)-phenyl]-1,3-dihydro-benzo[b][1,4]diazepin-2-one To a solution of 3-[7-(4-fluoro-phenyl)-4-oxo-4,5-dihydro-3H-benzo[b][1,4]diazepin-2-yl]-benzoic acid (Example 163) (262 mg, 0.7 mmol) and 1-hydroxybenzotriazole (130 mg, 0.84 mmol) in CH$_3$CN/DMF (7 mL/10 mL), cooled to 0° C., was added EDC (161 mg, 0.84 mmol) and the mixture was stirred at 0° C. for 1 h. N-hydroxy-acetamidine (62 mg, 0.84 mmol) was added and stirring was continued for 4 h at 23° C. The reaction mixture was partitioned between ethyl acetate and H$_2$O and the organic layer was dried over Na$_2$SO$_4$ and evaporated in vacuum. The residue was heated in toluene (30 mL) for 20 h at reflux. The mixture was cooled, evaporated in vacuum and the residue was chromatographed on silica gel using ethyl acetate/hexane (2:1) as eluent. The purified product was triturated with ethyl acetate to give the title compound as light yellow solid (49 mg). MS (ISN) 411.2 [(M−H)$^-$]; mp 266–268° C.

Example 170

8-(4-Fluoro-phenyl)-4-(2-hydroxy-phenyl)-1,3-dihydro-benzo[b][1,4]diazepin-2-one A mixture of 4'-fluoro-biphenyl-3,4-diamine (prepared from (3-amino-4'-fluoro-biphenyl-4-yl)-carbamic acid tert.-butyl ester (Example G39) by treatment with TFA) (121 mg, 0.6 mmol) and 4-hydroxycoumarin (97 mmol, 0.6 mmol) in xylene (8 mL) was heated to 130° C. for 6 h. A yellow precipitate started to form after ca. 1 h. The mixture was cooled to 23° C., diluted with ethyl acetate (8 mL) and hexane (8 mL) and stirring was continued for 15 min. The precipitate was collected by filtration and triturated with ethyl acetate/hexane (1:1) to give the title compound as a mixture with the isomeric 7-(4-fluoro-phenyl)-4-(2-hydroxy-phenyl)-1,3-dihydro-benzo[b][1,4]diazepin-2-one as yellow solid (117 mg).

MS (ISP) 347.3 [(M+H)+].

Example 171

4-(3-Chloro-2,4-dihydroxy-phenyl)-8-(4-fluoro-phenyl)-1,3-dihydro-benzo[b][1,4]diazepin-2-one By subjecting 4'-fluoro-biphenyl-3,4-diamine (prepared from (3-amino-4'-fluoro-biphenyl-4-yl)-carbamic acid tert.-butyl ester (Example G39) by treatment with TFA) (121 mg, 0.6 mmol) and 8-chloro-4,8-dihydroxycoumarin (128 mmol, 0.6 mmol) in an analogous manner to the procedure described in Example 170, the title compound was obtained as a mixture with the isomeric 4-(3-chloro-2,4-dihydroxy-phenyl)-7-(4-fluoro-phenyl)-1,3-dihydro-benzo[b][1,4]diazepin-2-one as light yellow solid (103 mg).

MS (ISN) 395.1 [(M−H)−].

Example I

Tablets of the following composition are produced in a conventional manner:

| mg/Tablet | |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

| mg/Tablet | |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

| mg/Capsule | |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

The invention claimed is:
1. A compound of the formula:

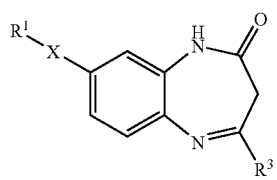

wherein
X is a single bond,
$R^1$ is selected from the group consisting of
  hydrogen,
  halogen,
  nitro,
  unsubstituted lower alkyl or lower alkyl substituted by halogen,
  alkoxycarbonyl,
  unsubstituted lower cycloalkyl or cycloalkyl substituted with oxygen,
    unsubstituted benzoyl or benzoyl substituted with a substituent selected from the group consisting of lower alkyl, lower alkyl substituted by halogen and halogen,
  unsubstituted phenyl,
  phenyl substituted by a substituent selected from the group consisting of hydroxy, lower alkyl, lower alkyl substituted by halogen, lower cycloalkyl, lower alkoxy, lower alkoxy substituted by halogen and cyano,
  styrenyl,
  phenylethyl,
  napthyl,
  biphenyl,
  benzofuranyl,
  an unsubstituted 5- or 6-membered heterocyclic ring,
  a 5- or 6-membered heterocyclic ring substituted by a substituent selected from the group consisting of oxo, benzoyl, methanesulfonyl, benzenesulfonyl and acetyl; and
$R^3$ is selected from the group consisting of
  unsubstituted pyridine, unsubstituted thienyl and unsubstituted thiazolyl, or
  substituted pyridine, substituted thienyl and substituted thiazolyl, said substituted pyridine, said substituted thiophenyl or said substituted thiazoyl being substituted by a substituent selected from the group consisting of
halogen,
cyano,
nitro,
azido,
hydroxy,
carboxy,
morpholine-4-carbonyl,
carbamoyl,
thiocarbamoyl, N-hydroxycarbamoyl,
trimethylsilyl-ethynyl,
lower alkyl, lower alkynyl, lower alkoxy, halo-lower alkyl, 4-lower alkyl-piperazine-1-carbonyl, lower alkylaminocarbonyl, or
lower alkyl, lower alkynyl, lower alkoxy, halo-lower alkyl, 4-lower alkyl-piperazine-1-carbonyl, lower alkylaminocarbonyl substituted by a substituent selected from the group consisting of amino, lower alkylamino, acylamino, oxo, hydroxy; lower alkoxy, lower alkylthio, unsubstituted carboxy, esterified and amidated carboxy,
an unsubstituted 5-membered aromatic heterocycle,
a 5-membered aromatic heterocycle substituted by a substituent selected from the group consisting of
amino,
lower alkylamino,
acylamino,
oxo,
hydroxy,
lower alkoxy,
lower alkylthio,
carboxy,
carboxy esterified with lower alkyl,
carboxy amidated with lower alkylamino which is eventually substituted by hydroxy, lower alkyl,
lower alkyl substituted by a substituent selected from the group consisting of halogen, hydroxy, amino, lower alkylamino, acylamino, amidino and amidino substituted by a substituent selected from the group consisting of
lower alkyl,
—C(NRR')═NR" wherein R, R' and R" are hydrogen or lower alkyl,
hydroxy,
lower alkoxy,
lower alkylthio,
acyloxy,
lower alkylsulfinyl,
lower alkylsulfonyl,
lower alkoxy-lower alkylsulfanyl,
lower alkylsulfanyl,
cycloalkylsulfinyl,
cycloalkylsulfonyl,
hydroxyimino,
lower alkoxyimino,
lower alkoximino which is esterified or amidated,
lower alkenyl,
oxo,
cyano,
carbamoyloxy,
sulfamoyl and
sulfamoyl substituted by lower alkyl; and
with the proviso that when X is a single bond and $R^3$ is pyridinyl, $R^1$ is not hydrogen or methyl,
or a pharmaceutically acceptable acid addition salt thereof.

2. The compound of formula I according to claim 1, wherein $R^3$ is selected from the group consisting of unsubstituted thienyl, thienyl substituted with halogen or cyano, unsubstituted pyridinyl and pyridinyl substituted with halogen or cyano.

3. The compound of formula I according to claim 2, selected from the group consisting of
2-[7-(4-Fluoro-phenyl)-4-oxo-4,5-dihydro-1H-benzo[b][1,4]diazepin-2-yl]-thiophene-3-carbonitrile, and
4-[7-(2,4-Difluoro-phenyl)-4-oxo-4,5-dihydro-3H-benzo[b][1,4]diazepin-2-yl]-pyridine-2-carbonitrile.

4. A pharmaceutical composition comprising a compound of formula 1

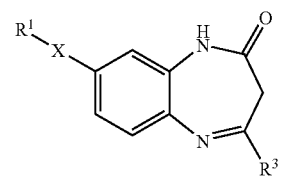

wherein
X is a single bond,
$R^1$ is selected from the group consisting of
hydrogen,
halogen,
nitro,
unsubstituted lower alkyl or lower alkyl substituted by halogen,
alkoxycarbonyl,
unsubstituted lower cycloalkyl or cycloalkyl substituted with oxygen,
unsubstituted benzoyl or benzoyl substituted with a substituent selected from the group consisting of lower alkyl, lower alkyl substituted by halogen and halogen,
unsubstituted phenyl,
phenyl substituted by a substituent selected from the group consisting of hydroxy, lower alkyl, lower alkyl substituted by halogen, lower cycloalkyl, lower alkoxy, lower alkoxy substituted by halogen and cyano,
styrenyl,
phenylethyl,
napthyl,
biphenyl,
benzofuranyl,
an unsubstituted 5- or 6-membered heterocyclic ring,
a 5- or 6-membered heterocyclic ring substituted by a substituent selected from the group consisting of oxo, benzoyl, methanesulfonyl, benzenesulfonyl and acetyl; and
$R^3$ is selected from the group consisting of
unsubstituted pyridine, unsubstituted thienyl and unsubstituted thiazolyl, or
substituted pyridine, substituted thienyl and substituted thiazolyl, said substituted pyridine, said substituted thienyl or said substituted thiazoyl being substituted by a substitutent selected from the group consisting of
halogen,
cyano,
nitro,
azido, hydroxy,
carboxy,
morpholine-4-carbonyl,
carbamoyl,
thiocarbamoyl, N-hydroxycarbamoyl,
trimethylsilyl-ethynyl,
lower alkyl, lower alkynyl, lower alkoxy, halo-lower alkyl, 4-lower alkyl-piperazine-1-carbonyl, lower alkylaminocarbonyl, or
lower alkyl, lower alkynyl, lower alkoxy, halo-lower alkyl, 4-lower alkyl-piperazine-1-carbonyl, lower alkylaminocarbonyl substituted by a substitutent selected from the group consisting of amino, lower alkylamino, acylamino, oxo, hydroxy; lower alkoxy, lower alkylthio, unsubstituted carboxy, esterified and amidated carboxy,
an unsubstituted 5-membered aromatic heterocycle,
a 5-membered aromatic heterocycle substituted by a substituent selected from the group consisting of
amino,
lower alkylamino,
acylamino,
oxo,
hydroxy,
lower alkoxy,
lower alkylthio,
carboxy,
carboxy esterified with lower alkyl,
carboxy amidated with lower alkylamino which is eventually substituted by hydroxy,
lower alkyl,
  lower alkyl substituted by a substituent selected from the group consisting of halogen, hydroxy, amino, lower alkylamino, acylamino, amidino and amidino substituted by a substituent selected from the group consisting of
  lower alkyl,
  —C(NRR')═NR" wherein R, R' and R" are hydrogen or lower alkyl, hydroxy,
  lower alkoxy,
  lower alkylthio,
  acyloxy,
  lower alkylsulfinyl,
  lower alkylsulfonyl,
  lower alkoxy-lower alkylsulfanyl,
  lower alkylsulfanyl,
  cycloalkylsulfinyl,
  cycloalkylsulfonyl,
  hydroxyimino,
  lower alkoxyimino,
  lower alkoximino which is esterified or amidated,
  lower alkenyl,
  oxo,
  cyano,
  carbamoyloxy,
  sulfamoyl and
  sulfamoyl substituted by lower alkyl; and
with the proviso that when X is a single bond and $R^3$ is pyridinyl, $R^1$ is not hydrogen or methyl, and a pharmaceutically acceptable excipient.

5. A process for preparing a compound of formula 1

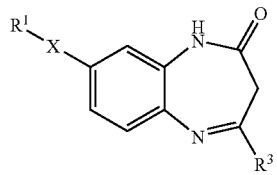

wherein
X is a single bond,
$R^1$ is selected from the group consisting of
  hydrogen,
  halogen,
  nitro,
  unsubstituted lower alkyl or lower alkyl substituted by halogen, alkoxycarbonyl,
  unsubstituted lower cycloalkyl or cycloalkyl substituted with oxygen,
    unsubstituted benzoyl or benzoyl substituted with a substituent selected from the group consisting of lower alkyl, lower alkyl substituted by halogen and halogen,
  unsubstituted phenyl,
  phenyl substituted by a substituent selected from the group consisting of hydroxy, lower alkyl, lower alkyl substituted by halogen, lower cycloalkyl, lower alkoxy, lower alkoxy substituted by halogen and cyano,
  styrenyl,
  phenylethyl,
  napthyl,
  biphenyl,
  benzofuranyl,
  an unsubstituted 5- or 6-membered heterocyclic ring,
  a 5- or 6-membered heterocyclic ring substituted by a substituent selected from the group consisting of oxo, benzoyl, methanesulfonyl, benzenesulfonyl and acetyl; and
$R^3$ is selected from the group consisting of
  unsubstituted pyridine, unsubstituted thienyl and unsubstituted thiazolyl, or
  substituted pyridine, substituted thienyl and substituted thiazolyl, said substituted pyridine, said substituted thienyl or said substituted thiazoyl being substituted by a substitutent selected from the group consisting of
  halogen,
  cyano,
  nitro,
  azido,
  hydroxy,
  carboxy,
  morpholine-4-carbonyl,
  carbamoyl,
  thiocarbamoyl, N-hydroxycarbamoyl,
  trimethylsilyl-ethynyl,
  lower alkyl, lower alkynyl, lower alkoxy, halo-lower alkyl, 4-lower alkyl-piperazine-1-carbonyl, lower alkylaminocarbonyl, or
  lower alkyl, lower alkynyl, lower alkoxy, halo-lower alkyl, 4-lower alkyl-piperazine-1-carbonyl, lower alkylaminocarbonyl substituted by a substitutent selected from the group consisting of amino, lower alkylamino, acylamino, oxo, hydroxy; lower alkoxy, lower alkylthio, unsubstituted carboxy, esterified and amidated carboxy,
an unsubstituted 5-membered aromatic heterocycle,
a 5-membered aromatic heterocycle substituted by a substituent selected from the group consisting of
amino,
lower alkylamino,
acylamino,
oxo,
hydroxy,
lower alkoxy,
lower alkylthio,
carboxy,
carboxy esterified with lower alkyl,
carboxy amidated with lower alkylamino which is eventually substituted by hydroxy, lower alkyl,
lower alkyl substituted by a substituent selected from the group consisting of halogen, hydroxy, amino, lower alkylamino, acylamino, amidino and amidino substituted by a substituent selected from the group consisting of
lower alkyl,
—C(NRR')=NR" wherein R, R' and R" are hydrogen or lower alkyl, hydroxy,
lower alkoxy,
lower alkylthio,
acyloxy,
lower alkylsulfinyl,
lower alkylsulfonyl,
lower alkoxy-lower alkylsulfanyl,
lower alkylsulfanyl,
cycloalkylsulfinyl,
cycloalkylsulfonyl,
hydroxyimino,
lower alkoxyimino,
lower alkoximino which is esterified or amidated,
lower alkenyl,
oxo,
cyano,
carbamoyloxy,
sulfamoyl and
sulfamoyl substituted by lower alkyl; and with the proviso that when X is a single bond and $R^3$ is pyridinyl, $R^1$ is not hydrogen or methyl, comprising reacting a compound of formula III:

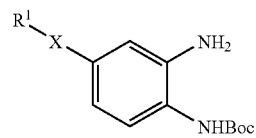

with a compound of formula IV or IVa:

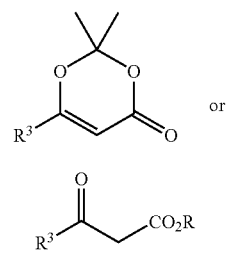

wherein R is ethyl or butyl, thereby yielding the compound of formula II

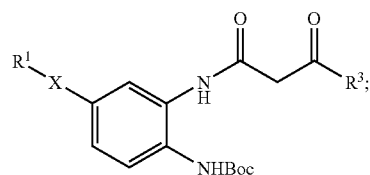

deprotecting of the amino group; and cyclizing, thereby forming a compound of formula I of claim 1.

* * * * *